US010202404B2

(12) United States Patent
Yoshinaga et al.

(10) Patent No.: US 10,202,404 B2
(45) Date of Patent: Feb. 12, 2019

(54) POLYCYCLIC PYRIDONE DERIVATIVE HAVING INTEGRASE INHIBITORY ACTIVITY

(71) Applicant: Shionogi & Co., Ltd., Osaka (JP)

(72) Inventors: Tomokazu Yoshinaga, Osaka (JP); Kouhei Nodu, Osaka (JP)

(73) Assignee: SHIONOGI & CO., LTD., Osaka (JP)

(*) Notice: Subject to any disclaimer, the term of this patent is extended or adjusted under 35 U.S.C. 154(b) by 0 days.

(21) Appl. No.: 15/988,388

(22) Filed: May 24, 2018

(65) Prior Publication Data

US 2018/0265525 A1    Sep. 20, 2018

Related U.S. Application Data

(62) Division of application No. 15/502,884, filed as application No. PCT/JP2015/073487 on Aug. 21, 2015, now Pat. No. 10,011,613.

(30) Foreign Application Priority Data

Aug. 22, 2014 (JP) ................. 2014-169776

(51) Int. Cl.
*C07D 513/04* (2006.01)
*C07D 513/14* (2006.01)
*A61K 31/4985* (2006.01)
*A61K 31/53* (2006.01)
*C07D 471/04* (2006.01)
*C07D 471/14* (2006.01)
*C07D 471/22* (2006.01)
*C07D 498/14* (2006.01)
*C07D 498/22* (2006.01)

(52) U.S. Cl.
CPC ........ *C07D 513/14* (2013.01); *A61K 31/4985* (2013.01); *A61K 31/53* (2013.01); *C07D 471/04* (2013.01); *C07D 471/14* (2013.01); *C07D 471/22* (2013.01); *C07D 498/14* (2013.01); *C07D 498/22* (2013.01)

(58) Field of Classification Search
CPC .................... C07D 513/14; A61K 31/4985
USPC ........................................................ 544/95
See application file for complete search history.

(56) References Cited

U.S. PATENT DOCUMENTS 9,200,009 B2    12/2015  Akiyama
2012/0108564 A1  5/2012  Miyazaki et al.
2012/0184734 A1  7/2012  Akiyama et al.
2013/0096109 A1  4/2013  Hattori et al.
2014/0256937 A1  9/2014  Akiyama
2015/0065485 A1  3/2015  Akiyama et al.

FOREIGN PATENT DOCUMENTS

| EP | 1 422 218 | 5/2004 |
|----|-----------|--------|
| EP | 1 541 558 | 6/2005 |
| EP | 1 544 199 | 6/2005 |
| EP | 1 950 212 | 7/2008 |
| EP | 2 042 502 | 4/2009 |
| EP | 2 045 242 | 4/2009 |
| EP | 2 181 985 | 5/2010 |
| EP | 2 266 958 | 12/2010 |
| EP | 2 620 436 | 7/2013 |
| EP | 2 940 019 | 11/2015 |
| EP | 3 042 894 | 7/2016 |
| JP | 2-96506 | 4/1990 |
| JP | 2-108668 | 4/1990 |
| JP | 2-108683 | 4/1990 |
| JP | 2004-244320 | 9/2004 |
| JP | 2013/054862 | 4/2013 |
| WO | 03/035076 | 5/2003 |
| WO | 2004/004657 | 1/2004 |
| WO | 2006/116764 | 11/2006 |
| WO | 2014/099586 | 6/2014 |
| WO | 2014/100323 | 6/2014 |
| WO | 2014/172188 | 10/2014 |
| WO | 2014/183532 | 11/2014 |
| WO | 2014/200880 | 12/2014 |
| WO | 2015/006731 | 1/2015 |
| WO | 2015/006733 | 1/2015 |
| WO | 2015/039348 | 3/2015 |
| WO | 2015/048363 | 4/2015 |
| WO | 2015/089847 | 6/2015 |
| WO | 2015/095258 | 6/2015 |

OTHER PUBLICATIONS

International Search Report dated Nov. 24, 2015 in International (PCT) Application No. PCT/JP2015/073487.
International Preliminary Report on Patentability and Written Opinion of the International Searching Authority dated Feb. 28, 2017 in corresponding International (PCT) Application No. PCT/JP2015/073487.

*Primary Examiner* — Kahsay Habte
(74) *Attorney, Agent, or Firm* — Wenderoth, Lind & Ponack, L.L.P.

(57) ABSTRACT

The present invention relates to a novel compound having an antiviral effect, more specifically, a pyridone derivative having HIV integrase inhibitory activity, and a medicament containing the same, in particular, an anti-HIV agent. The compound of the present invention has integrase inhibitory activity and/or cell proliferation inhibitory activity against viruses, in particular, HIV and drug-resistant strains thereof. Thus, the compound is useful in preventing or treating various diseases, viral infections (for example, AIDS), and the like in which integrase participates.

26 Claims, No Drawings

POLYCYCLIC PYRIDONE DERIVATIVE HAVING INTEGRASE INHIBITORY ACTIVITY

TECHNICAL FIELD

The present invention relates to novel compounds having antiviral activity, more particularly, polycyclic pyridone derivatives having HIV integrase inhibitory activity; and a medicament containing the same, particularly an anti-HIV agent.

BACKGROUND ART

Among viruses, human immunodeficiency virus (hereafter, referred to as HIV), a kind of retrovirus, is known to cause acquired immunodeficiency syndrome (hereafter, referred to as AIDS). The therapeutic agent for AIDS is mainly selected from a group of reverse transcriptase inhibitors (e.g., AZT, 3TC, etc.) and protease inhibitors (e.g., Indinavir, etc.), but they are proved to be accompanied by the following problems: side effects such as nephropathy, the emergence of resistant viruses, and the like. Thus, the development of anti-HIV agents having the other mechanisms of action therefrom has been desired.

On the other hand, currently, a multiple combination therapy is reported to be efficient in treatment for AIDS because of the frequent emergence of the resistant mutant virus. Two kinds of reverse transcriptase inhibitors and protease inhibitors are clinically used as an anti-HIV agent; however agents having the same mechanism of action often exhibit cross-resistance or only an additional activity. Therefore, development of anti-HIV agents having the other mechanism of action is desired.

Under the circumstances above, an integrase inhibitor has been focused on as an anti-HIV agent having a novel mechanism of action (Patent Documents 1 and 2). As an anti-HIV agent having such a mechanism of action, known are carbamoyl-substituted hydroxypyrimidinone derivative (Patent Document 3) and carbamoyl-substituted hydroxypyrrolidione derivative (Patent Document 4). Further, a patent application concerning carbamoyl-substituted hydroxypyridone derivative has been filed (Patent Document 5, Example 8).

Further, other known carbamoylpyridone derivatives include 5-alkoxypyridine-3-carboxamide derivatives and γ-pyrone-3-carboxamide derivatives, which are a plant growth inhibitor or herbicide (Patent Documents 6-8).

Furthermore, other HIV integrase inhibitors include nitrogen-containing condensed cyclic compounds (Patent Document 9).

Moreover, other HIV integrase inhibitors are known, and in such compounds, the terminal of an amide side chain is aryl (Patent Documents 10 and 11). In addition, a bicyclic HIV integrase inhibitor is known (Patent Document 12).

Further, the present applicant filed a patent application of an anti-influenza agent comprising a nitrogen-containing condensed cyclic compound as an active ingredient (Patent Document 13).

In addition, the present applicant filed a patent application of an HIV integrase inhibitor comprising a nitrogen-containing condensed cyclic compound as an active ingredient (Patent Document 14 and 15).

Moreover, HIV integrase inhibitors comprising a nitrogen-containing condensed cyclic compound having a spiro cycle or a bridge as an active ingredient were filed (Patent Documents 16 to 27).

PRIOR ART REFERENCES

Patent Document

[Patent Document 1] International Publication No. 03/016275 pamphlet
[Patent Document 2] International Publication No. 2004/024693 pamphlet
[Patent Document 3] International Publication No. 03/035076 pamphlet
[Patent Document 4] International Publication No. 2004/004657 pamphlet
[Patent Document 5] Japanese Laid-Open Publication No. 2004-244320
[Patent Document 6] Japanese Laid-Open Publication No. H2-108668
[Patent Document 7] Japanese Laid-Open Publication No. H2-108683
[Patent Document 8] Japanese Laid-Open Publication No. H2-96506
[Patent Document 9] International Publication No. 2005/016927 pamphlet
[Patent Document 10] International Publication No. 2006/116764 pamphlet
[Patent Document 11] International Publication No. 2007/049675 pamphlet
[Patent Document 12] International Publication No. 2011/105590 pamphlet
[Patent Document 13] International Publication No. 2010/147068 pamphlet
[Patent Document 14] International Publication No. 2011/129095 pamphlet
[Patent Document 15] International Publication No. 2013/054862 pamphlet
[Patent Document 16] International Publication No. 2014/099586 pamphlet
[Patent Document 17] International Publication No. 2014/100323 pamphlet
[Patent Document 18] International Publication No. 2014/104279 pamphlet
[Patent Document 19] International Publication No. 2014/172188 pamphlet
[Patent Document 20] International Publication No. 2014/183532 pamphlet
[Patent Document 21] International Publication No. 2014/200880 pamphlet
[Patent Document 22] International Publication No. 2015/039348 pamphlet
[Patent Document 23] International Publication No. 2015/048363 pamphlet
[Patent Document 24] International Publication No. 2015/089847 pamphlet
[Patent Document 25] International Publication No. 2015/095258 pamphlet
[Patent Document 26] International Publication No. 2015/006731 pamphlet
[Patent Document 27] International Publication No. 2015/006733 pamphlet

SUMMARY OF THE INVENTION

Problems to be Solved by the Invention

Under such the circumstances, the development of a novel integrase inhibitor has been desired.

Means to Solve the Problems

The present inventors intensively studied to find that a novel pyridone derivative has potent HIV integrase inhibitory activity. Moreover, the present inventors have discovered that a compound of the present invention and a medicament containing the same are useful as an antiviral agent (e.g., antiretroviral agent, anti-HIV agent, anti-HTLV-1 (Human T cell leukemia virus type 1) agent, anti-FIV (Feline immunodeficiency virus) agent, anti-SIV (Simian immunodeficiency virus) agent), especially an anti-HIV agent, an anti-AIDS agent, a therapeutic for associated diseases, or the like, to accomplish the present invention shown below.

[1] A compound represented by the following formula (I-1) or (I-2), or its pharmaceutically acceptable salt:

[Chemical Formula 1]

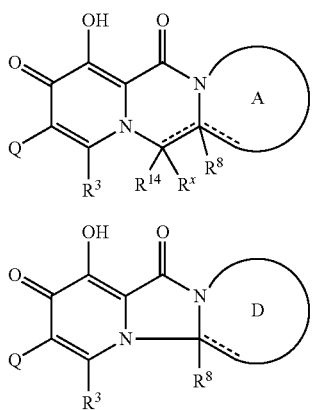

wherein Q is a substituted or unsubstituted carbocyclyl or substituted or unsubstituted heterocyclyl;

A ring is a substituted or unsubstituted heterocycle;

D ring is a substituted or unsubstituted heterocycle;

$R^3$ is a hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy, or substituted or unsubstituted amino;

$R^8$ is a hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy or substituted or unsubstituted amino;

$R^{14}$ and $R^x$ are each independently, hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$, —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl or substituted or unsubstituted aminocarbonyl;

$R^5$ is a hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, hydroxy, substituted or unsubstituted amino, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue or lower alkyl substituted with substituted or unsubstituted phosphoric acid residue (wherein a heteroatom group selected from the group consisting of CO, O, S, SO, $SO_2$, $NR^a$ ($R^a$ is a hydrogen or lower alkyl), —N= and =N— may intervene in the lower alkyl);

or $R^{14}$ and $R^x$ may be taken together with neighboring atoms to form substituted or unsubstituted spiro ring;

the broken line represents the presence or absence of a bond;

when the broken line adjacent to the carbon atom connected with $R^x$ represents the presence of a bond, $R^x$ is absence;

when the broken line adjacent to the carbon atom connected with $R^8$ represents the presence of a bond, $R^8$ is absence;

both the broken lines adjacent to the carbon atom connected with $R^8$ cannot represent the presence of a bond at the same time; and provided that the following compounds are excluded:

[Chemical Formula 2]

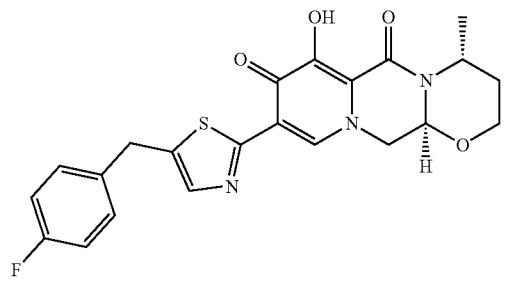

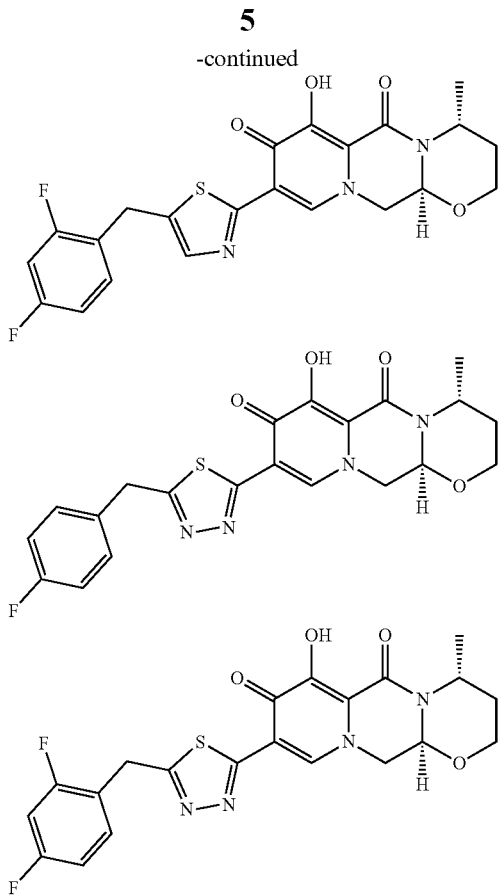

[2] The compound represented by the following formula (I-1) or its pharmaceutically acceptable salt according to the above item [1]:

[Chemical Formula 3]

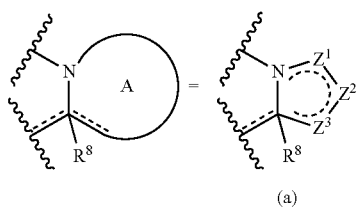
(I-1)

wherein each symbol is defined as the same above item [1].

[3] The compound or its pharmaceutically acceptable salt according to the above item [2], wherein A ring is represented by any one of the following rings:

[Chemical Formula 4]

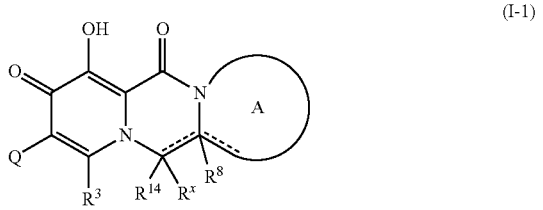

(a)        (b)        (c)

wherein $Z^1$, $Z^2$, $Z^3$, $Z^4$ and $Z^5$ are each independently $CR^1R^2$, $CR^1$, O, S, SO, $SO_2$, N or $NR^{19}$;

or $Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ may be taken together to form substituted or unsubstituted (C2-C4) bridge;

$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryl oxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [1]), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted aryl carbonyl, substituted or unsubstituted aryl lower alkylcarbonyl, substituted or unsubstituted aryl oxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

or $R^1$ and $R^2$ may be taken together to form oxo, thioxo or substituted or unsubstituted spiro ring;

$R^{19}$ is a hydrogen, substituted or unsubstituted lower alkyl, substituted or unsubstituted lower alkenyl, substituted or unsubstituted lower alkylcarbonyl or substituted or unsubstituted lower alkylsulfonyl;

the broken line represents the presence or absence of a bond; and $R^8$ is defined as the same above item [1].

[4] The compound or its pharmaceutically acceptable salt according to the above item [2], wherein A ring is represented by any one of the following rings:

[Chemical Formula 5]

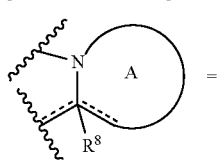
=

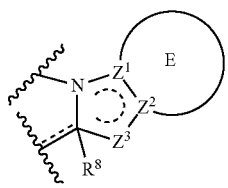
(a)

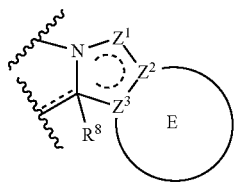
(b)

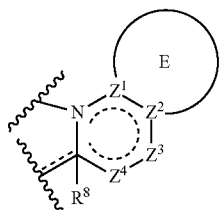
(c)

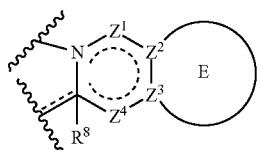
(d)

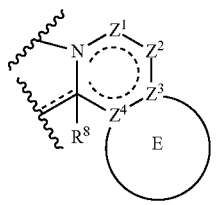
(e)

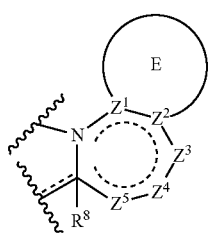
(f)

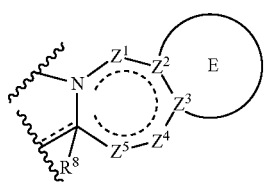
(g)

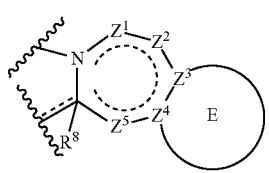
(h)

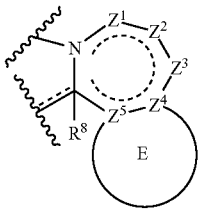
(i)

wherein E ring is substituted or unsubstituted carbocycle or substituted or unsubstituted heterocycle;

$Z^1, Z^2, Z^3, Z^4$ and $Z^5$ are each independently $CR^1R^2$, $CR^1$, C, O, S, SO, $SO_2$, N or $NR^{19}$ (when $Z^1, Z^2, Z^3, Z^4$ or $Z^5$ is/are constituent atom(s) of E ring, $Z^1, Z^2, Z^3, Z^4$ and $Z^5$ are each independently $CR^1$, C or N);

or $Z^1$ and $Z^3$, $Z^1$ and $Z^4$, $Z^1$ and $Z^5$, $Z^2$ and $Z^4$, $Z^2$ and Z, or $Z^3$ and $Z^5$ may be taken together to form substituted or unsubstituted (C2-C4) bridge;

$R^1$ and $R^2$ are each independently hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [1]), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

or $R^1$ and $R^2$ may be taken together to form oxo, thioxo or substituted or unsubstituted spiro ring;

$R^{19}$ is a hydrogen, substituted or unsubstituted lower alkyl, substituted or unsubstituted lower alkenyl, substituted or unsubstituted lower alkylcarbonyl or substituted or unsubstituted lower alkylsulfonyl;

$R^8$ is defined as the same above item [1]; and the broken line represents the presence or absence of a bond;

[5] The compound or its pharmaceutically acceptable salt according to the above item [4], wherein E ring is substituted or unsubstituted 4- to 7-membered carbocycle or substituted or unsubstituted 4- to 7-membered heterocycle.

[6] The compound represented by the following formula (I-1-1) or (I-2-1), or its pharmaceutically acceptable salt according to the above item [2]:

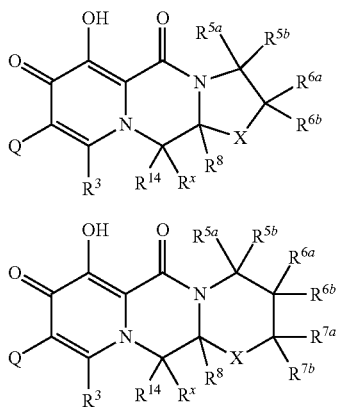

wherein X is $CR^{9a}R^{9b}$, $NR^{10}$, O or S;

$R^{5a}$, $R^{5b}$, $R^{6a}$, $R^{6b}$, $R^{7a}$, $R^{7b}$, $R^8$, $R^{9a}$, $R^{9b}$ and $R^{10}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^6$ is defined as the same above item [1]), —N═ and ═N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

$R^{5a}$ and $R^{5b}$, $R^{6a}$ and $R^{6b}$, $R^{7a}$ and $R^{7b}$, and/or $R^{9a}$ and $R^{9b}$ may be taken together to form oxo, thioxo or substituted or unsubstituted spiro ring;

or $R^{5b}$ and $R^{6b}$, $R^{6b}$ and $R^{7b}$, and/or $R^{7b}$ and $R^{9b}$ may be taken together with neighboring atoms to form substituted or unsubstituted carbocycle or substituted or unsubstituted heterocycle and/or $R^{5b}$ and $R^{7b}$, $R^{5b}$ and $R^8$, $R^{5b}$ and $R^{9b}$, $R^{6b}$ and $R^8$, $R^{6b}$ and $R^{9b}$, or $R^{7b}$ and $R^8$ may be taken together to form substituted or unsubstituted (C2-C4) bridge;

or $R^{5b}$ and $R^{10}$ may be taken together with neighboring atoms to form substituted or unsubstituted heterocycle or $R^{6b}$ and $R^{10}$, or $R^{7b}$ and $R^{10}$ may be taken together to form substituted or unsubstituted (C2-C4) bridge;

$R^x$ is a hydrogen; and the other symbols are defined as the same above item [1].

[7] The compound or its pharmaceutically acceptable salt according to the above item [6], wherein X is $CR^{9a}R^{9b}$, O or S.

[8] The compound or its pharmaceutically acceptable salt according to the above item [6] or [7], wherein $R^{5a}$ is hydrogen, halogen, hydroxy, substituted or unsubstituted lower alkyl or substituted or unsubstituted lower alkoxy.

[9] The compound or its pharmaceutically acceptable salt according to any one of the above items [6] to [8], wherein $R^{5b}$ is hydrogen.

[10] The compound or its pharmaceutically acceptable salt according to any one of the above items [6] to [9], wherein $R^{6a}$ is a hydrogen, halogen, hydroxy, substituted or unsubstituted lower alkyl or substituted or unsubstituted lower alkoxy.

[11] The compound or its pharmaceutically acceptable salt according to any one of the above items [6] to [10], wherein $R^{6b}$ is hydrogen.

[12] The compound or its pharmaceutically acceptable salt according to any one of the above items [6] to [11], wherein $R^{7a}$ is a hydrogen, halogen, hydroxy, substituted or unsubstituted lower alkyl or substituted or unsubstituted lower alkoxy.

[13] The compound or its pharmaceutically acceptable salt according to any one of the above items [6] to [12], wherein $R^{7b}$ is hydrogen.

[14] The compound or its pharmaceutically acceptable salt according to any one of the above items [6] to [13], wherein $R^8$ is hydrogen.

[15] The compound or its pharmaceutically acceptable salt according to any one of the above items [6] to [14], wherein $R^{9a}$ is a hydrogen, halogen, hydroxy, substituted or unsubstituted lower alkyl or substituted or unsubstituted lower alkoxy.

[16] The compound or its pharmaceutically acceptable salt according to any one of the above items [6] to [15], wherein $R^{9b}$ is hydrogen.

[17] The compound represented by any one of the following formula, or its pharmaceutically acceptable salt according to the above item [1]:

[Chemical Formula 7]

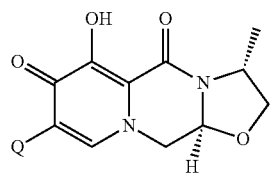

(I-1-2)

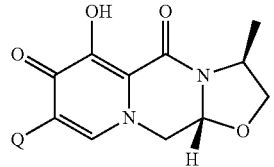

(I-1-3)

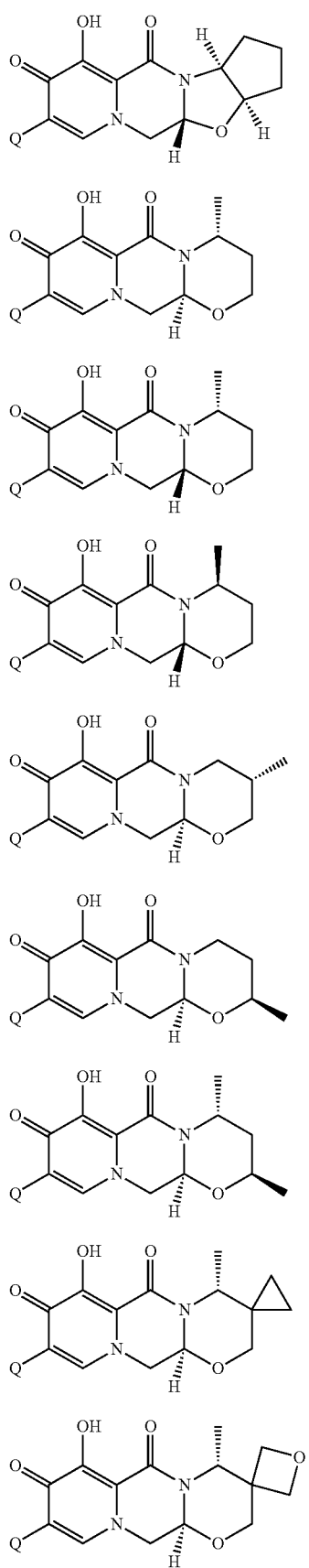
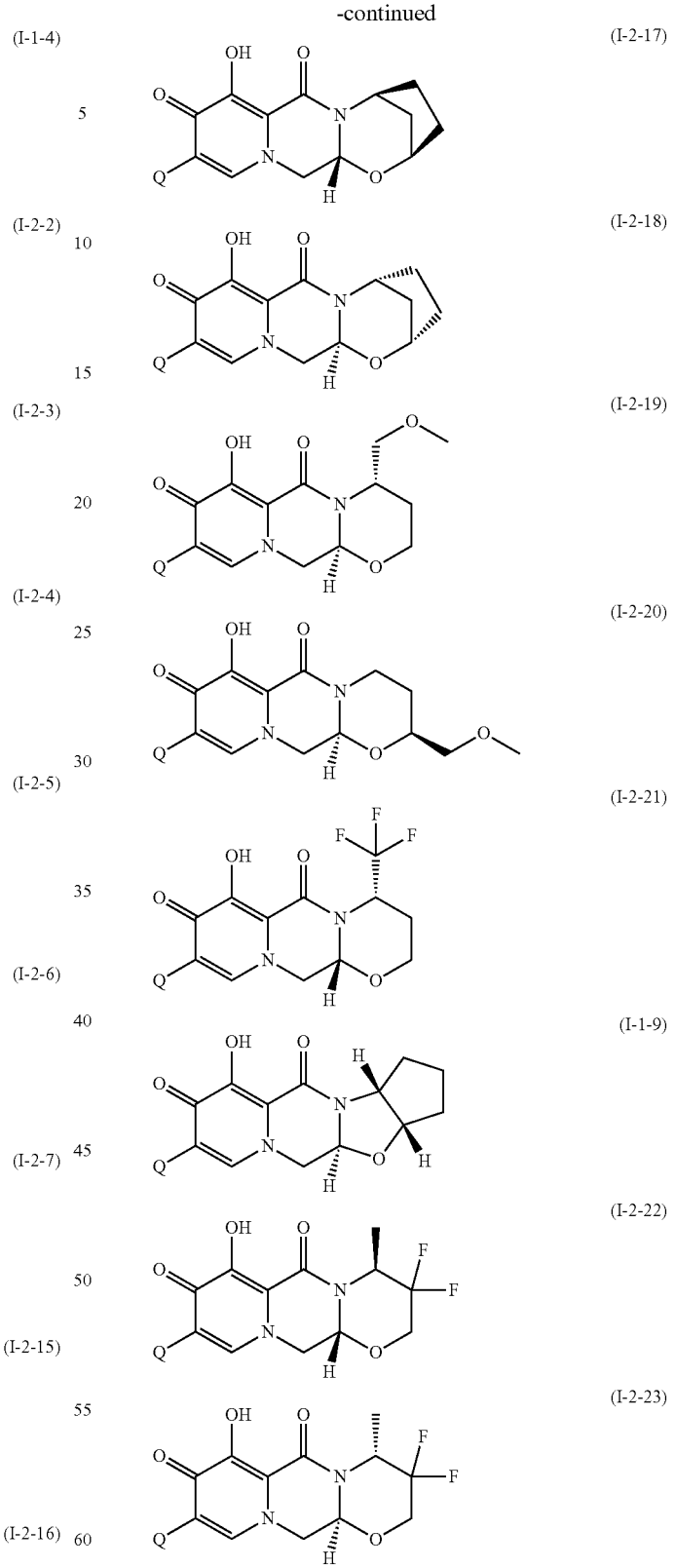
wherein each Q is defined as the same above item [1].
[18] The compound represented by any one of the following formula, or its pharmaceutically acceptable salt according to the above item [1]:

[Chemical Formula 8]
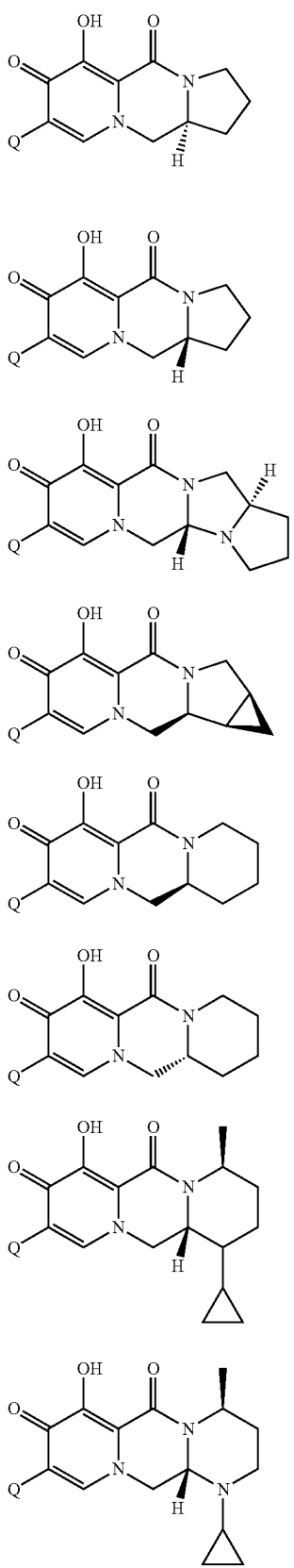
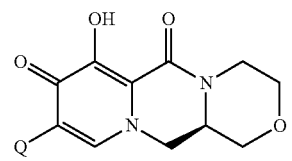
(I-2-12)
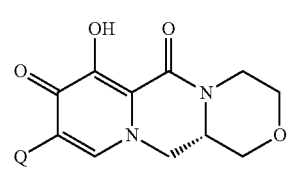
(I-2-13)
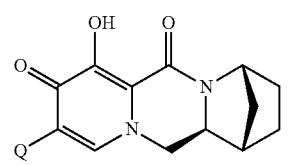
(I-2-14)
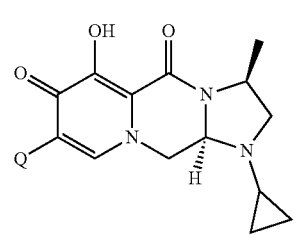
(I-1-10)
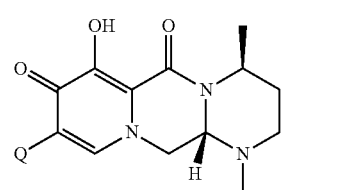
(I-2-24)
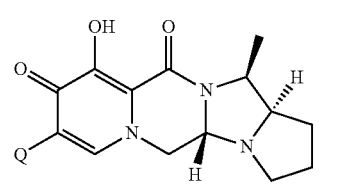
(I-1-11)
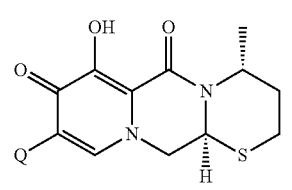
(I-2-25)
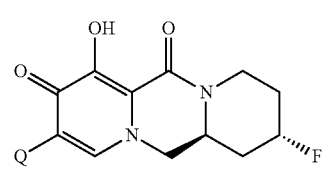
(I-2-26)

-continued (I-2-27)

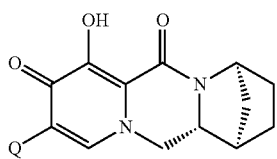

wherein each Q is defined the same above item [1].

[19] The compound represented by the following formula (I-2) or its pharmaceutically acceptable salt according to the above item [1]:

[Chemical Formula 9]

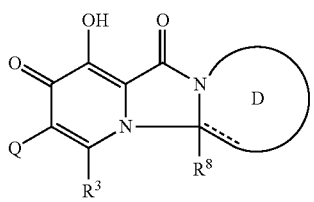

(I-2)

wherein each symbol is defined as the same above item [1].

[20] A compound represented by the following formula (I-3), or its pharmaceutically acceptable salt:

[Chemical Formula 10]

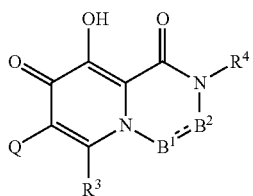

(I-3)

wherein Q is substituted or unsubstituted carbocyclyl or substituted or unsubstituted heterocyclyl;

the broken line represents the presence or absence of a bond;

when either one of $B^1$ and $B^2$ is $CR^{20}R^{21}$ and the other is $NR^{22}$, the broken line represents the absence of a bond; and $R^{20}$ and $R^{22}$ may be taken together with the neighboring atoms to form substituted or unsubstituted heterocycle;

when $B^2$ is $NR^{22}$, $R^4$ and $R^{22}$ may be taken together with the neighboring atoms to form substituted or unsubstituted heterocycle;

when $B^2$ is $CR^{20}R^{21}$, $R^4$ and $R^{21}$ may be taken together with the neighboring atoms to form substituted or unsubstituted heterocycle; or when either one of $B^1$ and $B^2$ is $CR^{23}$ and the other is N, the broken line represents the presence of a bond; when $B^2$ is $CR^{23}$, $R^4$ and $R^{23}$ may be taken together with the neighboring atoms to form substituted or unsubstituted heterocycle;

$R^{20}$, $R^{21}$, $R^{22}$ and $R^{23}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is independently selected from the same substituent group as $R^4$), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

$R^3$ is hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy or substituted or unsubstituted amino;

$R^4$ is hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, hydroxy, substituted or unsubstituted amino, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue or lower alkyl substituted with substituted or unsubstituted phosphoric acid residue (wherein a heteroatom group selected from the group consisting of CO, O, S, SO, $SO_2$, $NR^a$ ($R^a$ is hydrogen or lower alkyl), —N= and =N— may intervene in the lower alkyl); and provided that the compounds wherein $B^1$ is $NR^{22}$, the broken line represents the absence of a bond, and $R^4$ is unsubstituted ethyl or unsubstituted isopropyl are excluded.

[21] The compound represented by the following formula (I-3-1), or its pharmaceutically acceptable salt according to the above item [20]:

[Chemical Formula 11]

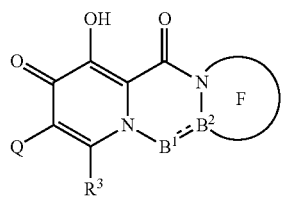

(I-3-1)

wherein F ring is substituted or unsubstituted heterocycle;
$B^1$ is $CR^{20}R^{21}$, N or $NR^{22}$;
when $B^1$ is $CR^{20}R^{21}$, the broken line represents the absence of a bond, and $B^2$ is N;
when $B^1$ is N, the broken line represents the presence of a bond, and $B^2$ is C;
when $B^1$ is $NR^{22}$, the broken line represents the absence of a bond, and $B^2$ is $CR^{20}$; and
the other symbols are defined as the same above item [20].

[22] The compound or its pharmaceutically acceptable salt according to the above item [20], wherein F ring is represented by any one of the following rings:

[Chemical Formula 12]

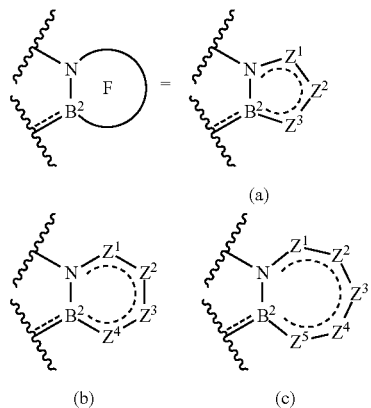

wherein $Z^1$, $Z^2$, $Z^3$, $Z^4$ and $Z^1$ are each independently $CR^1R^2$, $CR^1$, O, S, SO, $SO_2$, N or $NR^{19}$;
or $Z^1$ and $Z^3$, $Z^1$ and $Z^4$, $Z^1$ and $Z^5$, $Z^2$ and $Z^4$, $Z^2$ and $Z^6$, or $Z^3$ and $Z^5$ may be taken together to form substituted or unsubstituted (C2-C4) bridge;
$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [20]), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;
or $R^1$ and $R^2$ may be taken together to form oxo, thioxo or substituted or unsubstituted spiro ring;
$R^{19}$ is hydrogen, substituted or unsubstituted lower alkyl, lower alkenyl, substituted or unsubstituted lower alkylcarbonyl or substituted or unsubstituted lower alkylsulfonyl;
the broken line represents the presence or absence of a bond; and
the other symbols are defined as the same above item [20].

[23] The compound or its pharmaceutically acceptable salt according to the above item [21], wherein F ring is represented by any one of the following rings:

[Chemical Formula 13]

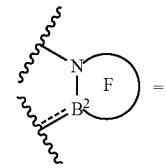

(a)

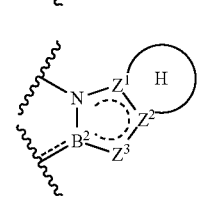

(b)

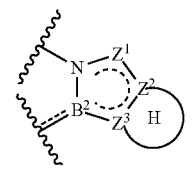

(c)

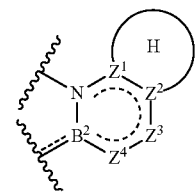

(d)

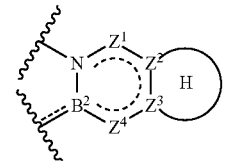

-continued (e)
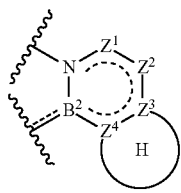

(f)
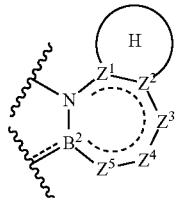

(g)
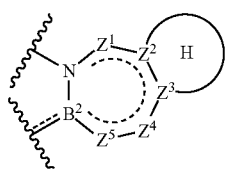

(h)
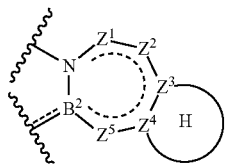

(i)
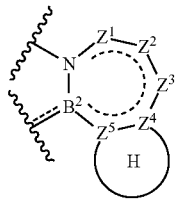

wherein 11 ring is substituted or unsubstituted carbocycle or substituted or unsubstituted heterocycle;

$Z^1$, $Z^2$, $Z^3$, $Z^4$ and $Z^5$ are each independently $CR^1R^2$, $CR^1$, C, O, S, SO, $SO_2$, N or $NR^{19}$ (when $Z^1$, $Z^2$, $Z^3$, $Z^4$ or $Z^5$ is/are constituent atom(s) of H ring, $Z^1$, $Z^2$, $Z^3$, $Z^4$ and $Z^5$ are each independently $CR^1$, C or N);

or $Z^1$ and $Z^3$, $Z^1$ and $Z^4$, $Z^1$ and $Z^5$, $Z^2$ and $Z^4$, $Z^2$ and Z, or $Z^3$ and $Z^5$ may be taken together to form substituted or unsubstituted (C2-C4) bridge;

$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [20]), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

or $R^1$ and $R^2$ may be taken together to form oxo, thioxo or substituted or unsubstituted spiro ring;

$R^{19}$ is hydrogen, substituted or unsubstituted lower alkyl, lower alkenyl, substituted or unsubstituted lower alkylcarbonyl or substituted or unsubstituted lower alkylsulfonyl;

the broken line represents the presence or absence of a bond; and the other symbols are defined as the same above item [20].

[24] The compound or its pharmaceutically acceptable salt according to the above item [23], wherein H ring is substituted or unsubstituted 4- to 7-membered carbocycle or substituted or unsubstituted 4- to 7-membered heterocycle.

[25] The compound represented by the following formula (I-3-2), or its pharmaceutically acceptable salt according to the above item [20]:

[Chemical Formula 14]

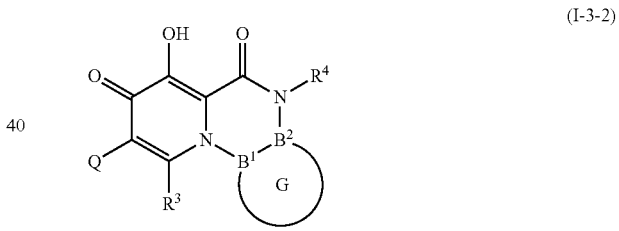

(I-3-2)

wherein G ring is substituted or unsubstituted carbocycle or substituted or unsubstituted heterocycle;

$B^1$ is ($CR^{21}$ or N;

when $B^1$ is $CR^{21}$, $B^2$ is N; when $B^1$ is N, $B^2$ is $CR^{21}$; and the other symbols are defined as the same above item [20].

[26] The compound or its pharmaceutically acceptable salt according to the above item [25], wherein G ring is represented by any one of the following rings:

[Chemical Formula 15]

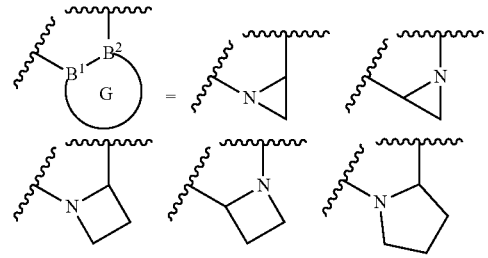

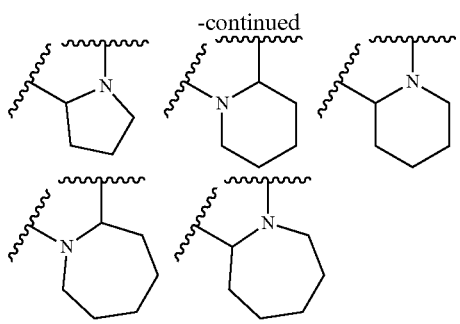

[27] The compound or its pharmaceutically acceptable salt according to any one of the above items [20] to [26], wherein $B^2$ is N or $NR^{22}$ (wherein $R^{22}$ is defined as the same above item [20]; proviso when the broken line represents the presence of a bond or when $B^2$ is constituent atom of F ring or G ring, $B^2$ is N).

[28] The compound represented by the following formula (I-3-3) or (I-3-4), or its pharmaceutically acceptable salt according to any one of the above items [20] to [27]:

[Chemical Formula 16]

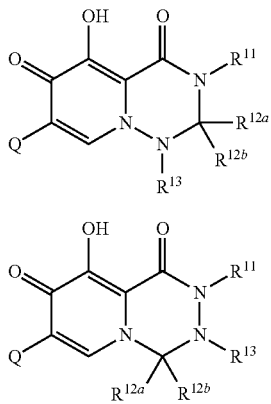

wherein $R^{11}$, $R^{12a}$, $R^{12b}$ and $R^{13}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [20]), —N═ and ═N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

or $R^{12a}$ and $R^{12b}$ may be taken together to form oxo, thioxo;

when the compound is represented by formula (I-3-4), $R^{12a}$ and $R^{12b}$ may be taken together to form substituted or unsubstituted spiro ring; and Q is defined as the same above item [20].

[29] The compound represented by the following formula (I-3-5) or (I-3-6), or its pharmaceutically acceptable salt according to any one of the above items [20] to [22]:

[Chemical Formula 17]

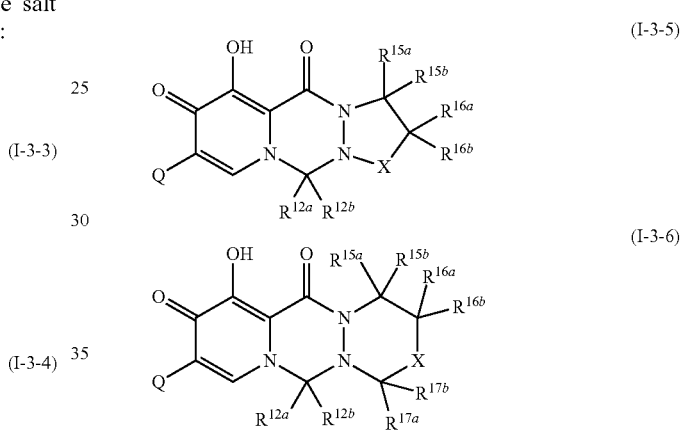

wherein X is $CR^{18a}R^{18b}$, $NR^{24}$, O or S;

$R^{15a}$, $R^{15b}$, $R^{16a}$, $R^{16b}$, $R^{17a}$, $R^{17b}$, $R^{18a}$, $R^{18b}$ and $R^{24}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is defined as the same above item [20]), —N═ and ═N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido;

or $R^{15a}$ and $R^{15b}$, $R^{16a}$ and $R^{16b}$, $R^{17a}$ and $R^{17b}$, or $R^{18a}$ and $R^{18b}$ may be taken together to form oxo, thioxo or substituted or unsubstituted spiro ring;

or $R^{15b}$ and $R^{16b}$, $R^{16b}$ and $R^{18b}$, and/or $R^{17b}$ and $R^{18b}$ may be taken together to form substituted or unsubstituted carbocycle or substituted or unsubstituted heterocycle; or $R^{15b}$ and $R^{17b}$, $R^{15b}$ and $R^{18b}$, or $R^{16b}$ and $R^{17b}$ may be taken together to form substituted or unsubstituted (C2-C4) bridge;

or $R^{16b}$ and $R^{24}$, or $R^{17b}$ and $R^{24}$ may be taken together to form substituted or unsubstituted heterocycle; or $R^{15b}$ and $R^{24}$ may be taken together to form substituted or unsubstituted (C2-C4) bridge; and the other symbols are defined as the same above item [20].

[30] The compound or its pharmaceutically acceptable salt according to the above item [29], wherein $R^{15a}$ is hydrogen or substituted or unsubstituted lower alkyl.

[31] The compound or its pharmaceutically acceptable salt according to the above item [29] or [30], wherein $R^{15b}$ is hydrogen.

[32] The compound or its pharmaceutically acceptable salt according to any one of the above items [29] to [31], wherein $R^{16a}$ is hydrogen or substituted or unsubstituted lower alkyl.

[33] The compound or its pharmaceutically acceptable salt according to any one of the above items [29] to [32], wherein $R^{16b}$ is hydrogen.

[34] The compound or its pharmaceutically acceptable salt according to any one of the above items [29] to [33], wherein $R^{17}$ is hydrogen or substituted or unsubstituted lower alkyl.

[35] The compound or its pharmaceutically acceptable salt according to any one of the above items [29] to [34], wherein $R^{17b}$ is hydrogen.

[36] The compound or its pharmaceutically acceptable salt according to any one of the above items [29] to [35], wherein $R^{18a}$ is hydrogen or substituted or unsubstituted lower alkyl.

[37] The compound or its pharmaceutically acceptable salt according to any one of the above items [29] to [36], wherein $R^{18b}$ is hydrogen.

[38] The compound or its pharmaceutically acceptable salt according to any one of the above items [29] to [37], wherein $R^{24}$ is hydrogen or substituted or unsubstituted lower alkyl.

[39] The compound represented by any one of the following formula, or its pharmaceutically acceptable salt according to the above item [20]:

[Chemical Formula 18]

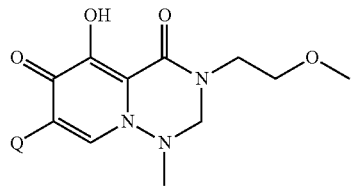

(I-3-7)

-continued

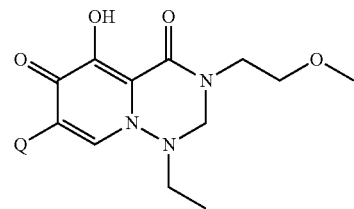

(I-3-8)

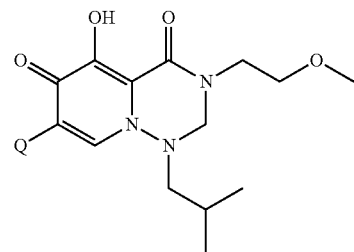

(I-3-9)

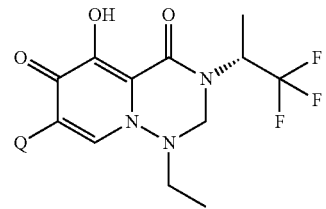

(I-3-10)

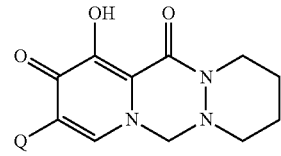

(I-3-11)

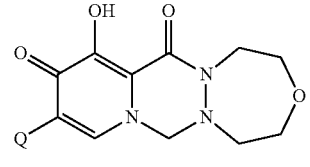

(I-3-12)

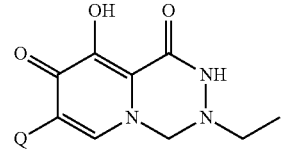

(I-3-13)

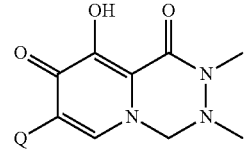

(I-3-14)

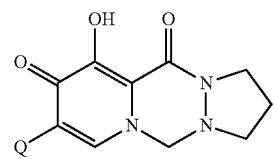

(I-3-15)

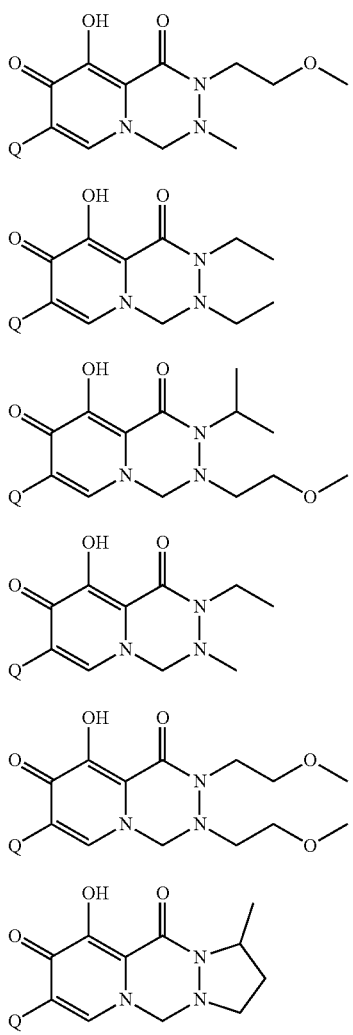

(I-3-16)
(I-3-17)
(I-3-18)
(I-3-19)
(I-3-20)
(I-3-21)

wherein each Q is defined as the same above item [20].

[40] The compound or its pharmaceutically acceptable salt according to any one of the above items [1] to [39], wherein Q is substituted or unsubstituted heterocyclyl.

[41] The compound or its pharmaceutically acceptable salt according to any one of the above items [1] to [40], wherein Q is substituted or unsubstituted 5- to 7-membered monocyclic heterocyclyl.

[42] The compound or its pharmaceutically acceptable salt according to any one of the above items [1] to [41], wherein Q is represented by any one of the following formula:

[Chemical Formula 19]

(1) 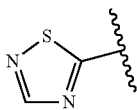

(2) 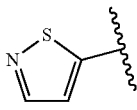

(3) 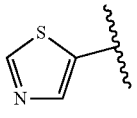

(4) 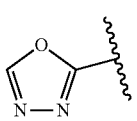

(5) 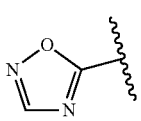

(6) 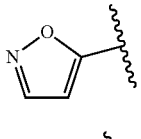

(7) 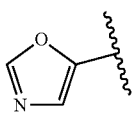

(8) 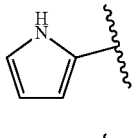

(9) 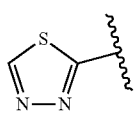

(10) 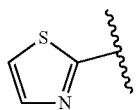

(11) 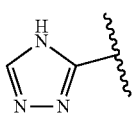

(12) 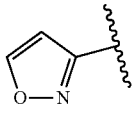

(13)

(14)

(15)

-continued

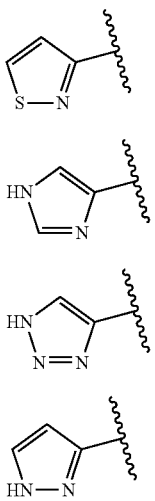

(16)

(17)

(18)

(19)

[43] The compound or its pharmaceutically acceptable salt according to any one of the above items [1] to [42], wherein Q is carbocyclyl or heterocyclyl substituted with the same or different, 1 to 4 substituent(s) selected from Substituent group A.
Substituent group A: lower alkyl, lower alkoxy, halogen, halogenated lower alkyl, halogenated lower alkoxy, and the group of formula (B):

[Chemical Formula 20]

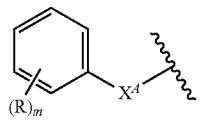

(B)

wherein $X^A$ is a group selected from the following group:
$X^{A1}$: a single bond;
$X^{A2}$: a group selected from C(=O) and C(=S);
$X^{A3}$: a heteroatom group selected from, S, SO, $SO_2$, and $N(R^{1'})$ wherein $R^{1'}$ is hydrogen or lower alkyl;
$X^{A4}$: a group formed by linking the same or different, two or more groups selected from $X^{A2}$ and $X^{A3}$;
$X^{A5}$: a group selected from —N=N—, —C($R^{1'}$)=N—, or —N=C($R^{1'}$)— wherein $R^{1'}$ is hydrogen or lower alkyl;
$X^{A6}$: substituted or unsubstituted lower alkylene or substituted or unsubstituted lower alkenylene;
$X^{A7}$: $X^{A6}$ intervened by one or any two or more groups selected from $X^{A2}$, $X^{A3}$, $X^{A4}$, and $X^{A5}$;
$X^{A8}$: a group $CR^{1'}R^{2'}$ wherein $R^{1'}$ and $R^{2'}$ are taken together with neighboring atoms to form carbocycle or heterocycle; and
$X^{A9}$: a spacer consisting of any combination of $X^{A1}$ to $X^{A8}$;
R is a group independently selected from the following group:
(1) lower alkyl,
(2) lower alkoxy,
(3) halogen,
(4) halogenated lower alkyl,
(5) halogenated lower alkoxy, and
(6) lower cycloalkyl.
m is an integer of 0 to 5.

[44] The compound or its pharmaceutically acceptable salt according to any one of the above items [1] to [43], wherein Q is represented by the following formula (1) or (2):

[Chemical Formula 21]

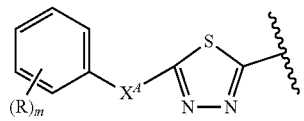

(1)

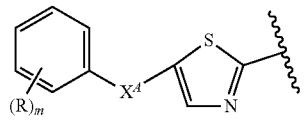

(2)

wherein each symbol is defined as the same above item [43].
[45] The compound or its pharmaceutically acceptable salt according to the above item [43] or [44], wherein $X^A$ is lower alkylene; R is independently lower alkoxy, halogen or halogenated lower alkyl; and m is 1 or 2.
[46] The compound or its pharmaceutically acceptable salt according to any one of the above items [1] to [45], wherein Q is substituted or unsubstituted carbocyclyl or substituted or unsubstituted heterocyclyl
provided that the following compounds are excluded:

[Chemical Formula 22]

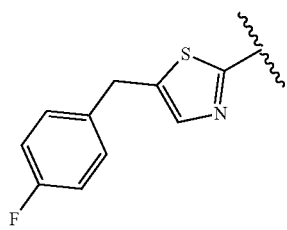

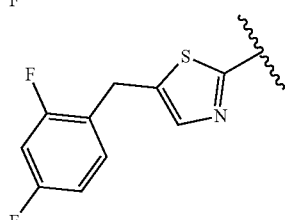

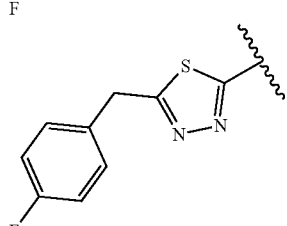

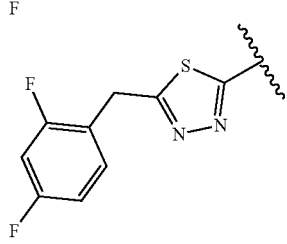

[47] The compound or its pharmaceutically acceptable salt according to any one of the above items [1] to [46], wherein Q is represented by any one of the following groups:
[Chemical Formula 23]
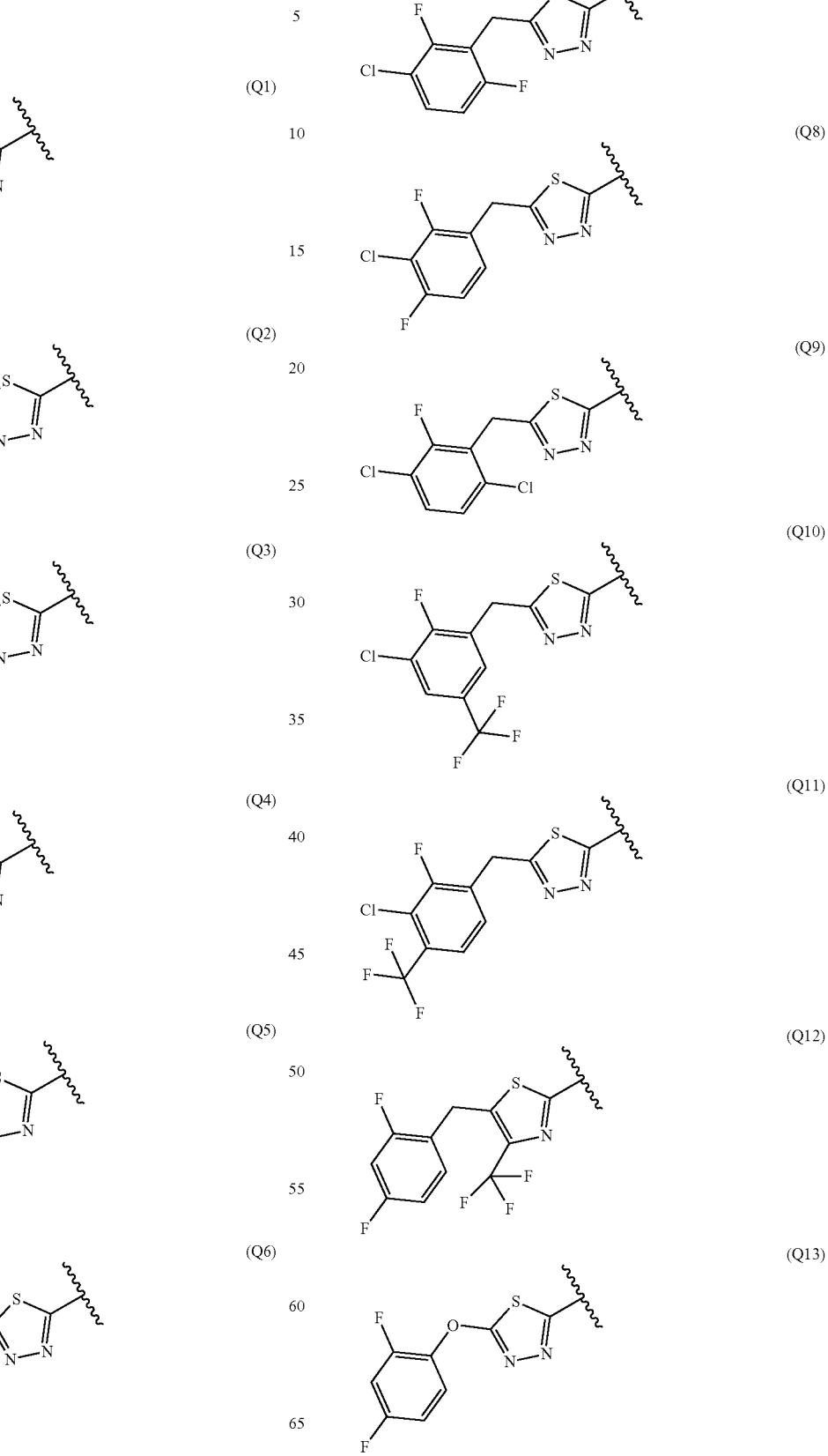

(Q14) 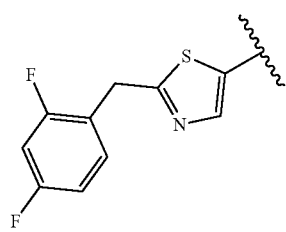
(Q15) 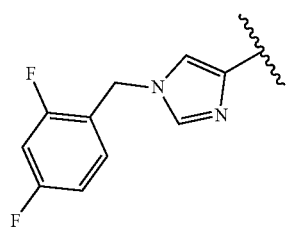
(Q16) 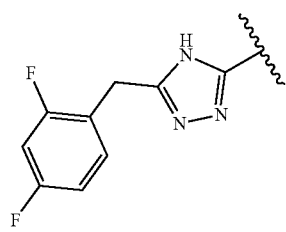
(Q17) 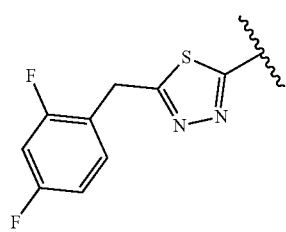
(Q18) 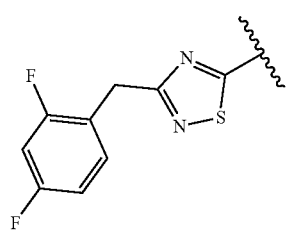
(Q19) 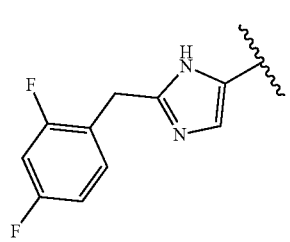
(Q20) 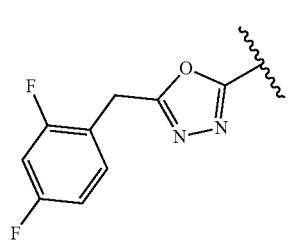
(Q21) 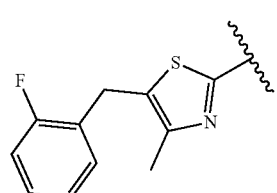
(Q22) 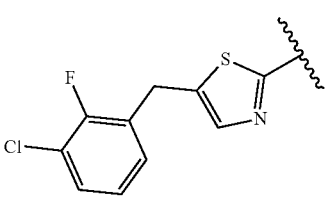
(Q23) 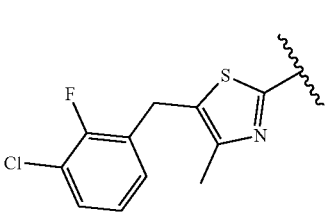
(Q24) 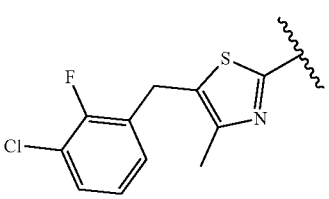
(Q25) 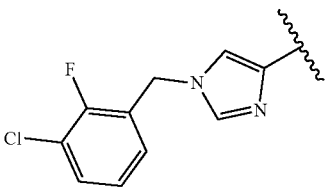
(Q26) 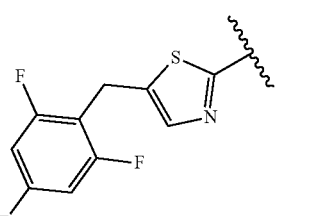
(Q27) 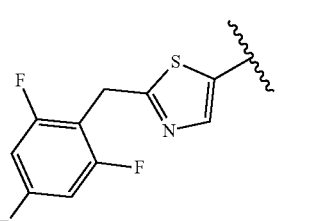

-continued

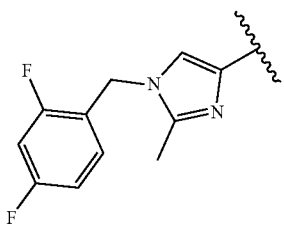

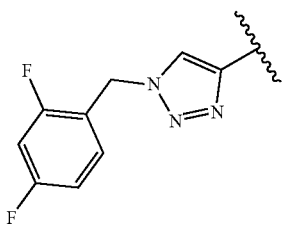

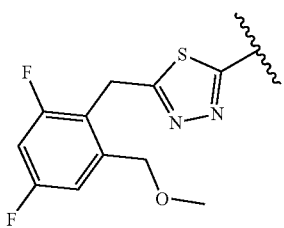

[48] The compound represented by any one of the following formula (I-1'), (I-2') or (I-3'), or its pharmaceutically acceptable salt:

[Chemical Formula 24]

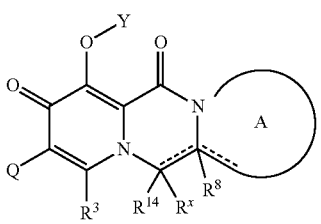
(I-1')

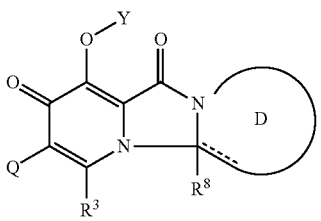
(I-2')

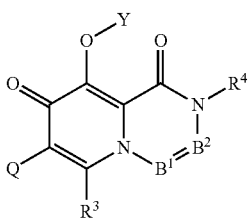
(I-3')

wherein Y is represented by any one of the following group:

[Chemical Formula 25]

(Q28)

(Q29)

(Q30)

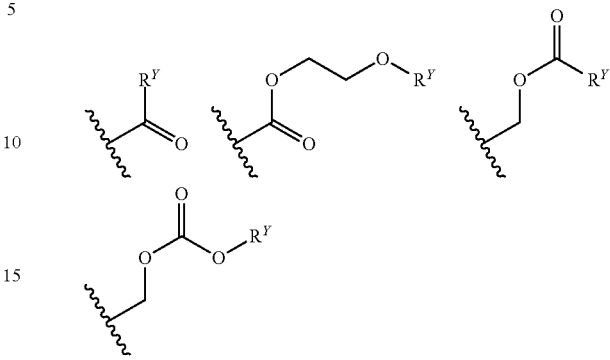

wherein $R^Y$ is substituted or unsubstituted alkyl; and the other symbols are defined as the same above item [1].

[49] A pharmaceutical composition comprising the compound according to any of the above items [1] to [48], or a pharmaceutically acceptable salt thereof.

[50] The pharmaceutical composition according to the above item [49], which has anti-HIV activity.

[51] The pharmaceutical composition according to the above [49], which has an HIV integrase inhibitory activity.

[52] A method for treating or preventing AIDS by administering the compound of any one of the above items [1] to [48] to human or animals, or a pharmaceutically acceptable salt thereof.

[53] The compound of any one of the above items [1] to [48], or a pharmaceutically acceptable salt thereof for medical treatment.

[54] Use of the compound of any one of the above items [1] to [48], or its pharmaceutically acceptable salt for the manufacture of a therapeutic or preventive agent for AIDS.

[55] The compound or its pharmaceutically acceptable salt according to the above item [1], provided that the compounds having combination of S-T-U are excluded wherein S is represented by any group of the following:

[Chemical Formula 26]

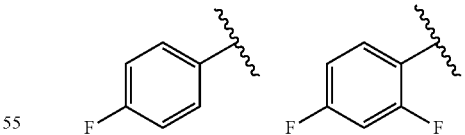

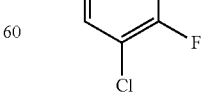

T is represented by any group of the following:

wherein the left bond is combined to S, and the right bond is combined to U;

[Chemical Formula 27]

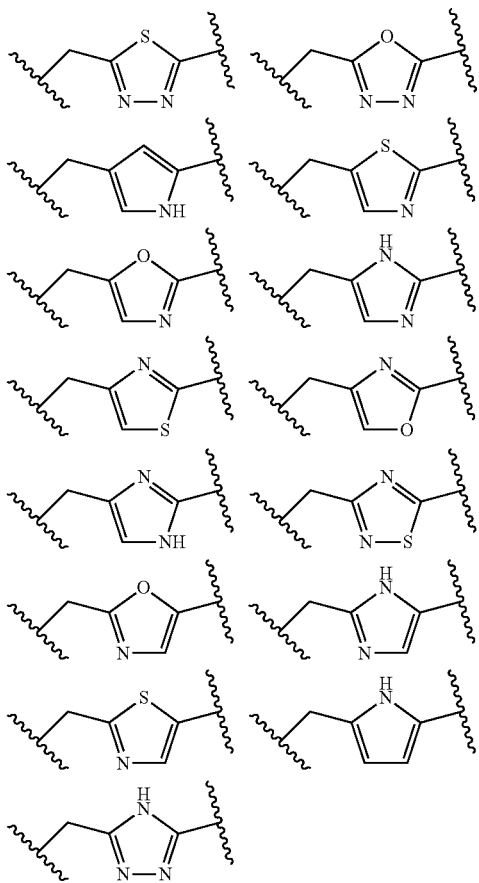

U is represented by any group of the following:

[Chemical Formula 28]

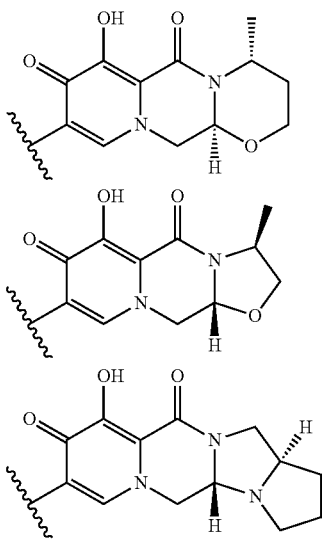

[56] The compound or its pharmaceutically acceptable salt according to any one of the above item [20] or [26], wherein $B^1$ and $B^2$ are each independently $CR^{20}R^{21}$ or $CR^{23}$.

The present invention further provides a method of preventing or treating HIV that is characterized by administering an effective amount of the above-described compound to a human.

The present invention further provides the above-described compound for using as an anti-IIIV agent.

Effect of the Invention

The present compound has integrase inhibitory activity and/or cell proliferation inhibitory activity against viruses, in particular, HIV and drug-resistant strains thereof. Thus, the compound is useful in preventing or treating various diseases, viral infections (e.g., AIDS), and the like in which integrase participates. More preferably, the present compound is also excellent in resistance profile that it is difficult for the compound to cause a new HIV-resistant virus, and the like. Further preferably, the present compound has a preventive or therapeutic effect on IIIV drug-resistant virus. Further more preferably, the present compound is useful as a pharmaceutical agent that is excellent in solubility, peroral absorbability, metabolic stability, bioavailability or the like, and for which there is little concern about cytotoxicity and a side effect (e.g., mutagenicity, the QT interval prolongation of the electrocardiogram).

MODE FOR CARRYING OUT THE INVENTION

The terms used herein are explained below. Each term, alone or in combination with another term, means as follows.

"Lower alkylene" means a linear or branched $C_{1-6}$ lower alkylene such as methylene, ethylene, trimethylene, propylene, tetramethylene, ethylethylene, pentamethylene, hexamethylene, or the like. Preferred is a $C_{1-4}$ linear lower alkylene such as methylene, ethylene, trimethylene, or tetramethylene. More preferred is methylene or ethylene.

"Lower alkenylene" means a linear or branched $C_{2-6}$ lower alkenylene group, which consists of the above "Lower alkylene" having one or more double bonds, such as vinylene, propylene, or butenylene. Preferred is a $C_{2-3}$ linear lower alkenylene such as vinylene or propylene.

"Alkyl" means a linear or branched $C_{1-10}$ alkyl group such as methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl, and the like. Preferred is a $C_{1-6}$ lower alkyl and more preferred is a $C_{1-4}$ lower alkyl, such as methyl, ethyl, n-propyl, isopropyl, n-butyl, isobutyl, sec-butyl, tert-butyl, n-pentyl, isopentyl, neopentyl, tert-pentyl, n-hexyl, and isohexyl.

When lower alkyl is intervened by —N= or =N—, the lower alkyl may have a double bond to form, for example, —CH$_2$—N=CH$_2$, —CH=N—CH$_3$, or the like.

"Alkenyl" means a linear or branched $C_{2-8}$ alkenyl, which consists of the above "alkyl" having one or more double bonds, such as vinyl, 1-propenyl, 2-propenyl, 1-butenyl, 2-butenyl, 3-butenyl, 1,3-butadienyl, 3-methyl-2-butenyl, and the like. Preferred is $C_{2-6}$ lower alkenyl, and more preferred is $C_{2-4}$ lower alkenyl.

"Lower alkenyloxy" means an oxy attached to the above "lower alkenyl", such as vinyloxy, 1-propenyloxy, 2-propenyloxy, 1-butenyloxy, 2-butenyloxy, 3-butenyloxy, 1,3-butadienyloxy, 3-methyl-2-butenyloxy, and the like.

"Alkynyl" means a linear or branched $C_{2-8}$ alkenyl, which consists of the above "alkyl" having one or more triple bonds, such as ethynyl, propargyl, and the like. Preferred is $C_{2-6}$ lower alkynyl, and more preferred is $C_{2-4}$ lower alkynyl.

"Carbocyclic group" means a saturated or unsaturated $C_{3-10}$ carbocyclic group, and includes cycloalkyl, cycloalkenyl, and aryl.

"Cycloalkyl" means a $C_{3-10}$ cyclic saturated hydrocarbon group, such as cyclopropyl, cyclobutyl, cyclopentyl, cyclohexyl, cyclopentyl, cyclooctyl, and the like. Preferred is $C_{3-6}$ cycloalkyl.

"Cycloalkyl lower alkyl" means a lower alkyl substituted with the above cycloalkyl, such as cyclopropylmethyl, cyclopropylethyl, cyclobutylmethyl, cyclopentylmethyl, cyclohexylmethyl, cyclohexylethyl, and the like. Preferred is $C_{3-6}$ cycloalkyl lower alkyl.

"Aryl" means a monocyclic aromatic hydrocarbon group (phenyl) and a polycyclic aromatic hydrocarbon (e.g., 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and the like). Preferred is phenyl or naphthyl (e.g., 1-napthyl, 2-naphthyl).

"Aralkyl" or "aryl lower alkyl" means the above "lower alkyl" substituted with one to three of the above "aryl", such as benzyl, diphenylmethyl, triphenylmethyl, phenethyl, 1-napthylmethyl, 2-naphthylmethyl, and the like. Preferred is benzyl.

"Aryloxy" means an oxy attached to the above "aryl", such as 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, 9-phenanthryloxy, and the like. Preferred is phenyloxy or naphthyloxy (e.g., 1-napthyloxy, 2-naphthyloxy).

"Heterocyclic group" means "heteroring" or "heteroaryl".

"Heteroring" means a non-aromatic heterocyclic group (preferably 5- to 7-membered ring) which has at least one of nitrogen, oxygen, phosphorus and/or sulfur atoms in the ring and may be bonded at any substitutable position such as 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperadinyl, 2-piperadinyl, 2-morpholinyl, 3-morpholinyl, morpholino, tetrahydropyranyl, and the like. The "non-aromatic heterocyclic group" is a saturated or unsaturated ring.

"Heteroaryl" means a monocyclic aromatic heterocyclic group or a condensed aromatic heterocyclic group.

Monocyclic aromatic heterocyclic group means a group derived from a 5- to 8-membered aromatic ring optionally containing one to four of oxygen, sulfur, phosphorus and/or nitrogen atoms in the ring wherein the group may be bonded at any substitutable position.

Condensed aromatic heterocyclic group means a group wherein a 5- to 8-membered aromatic ring optionally containing one to four of oxygen, sulfur, phosphorus and/or nitrogen atoms in the ring is condensed with one to four of 5- to 8-membered aromatic carbocycle(s) or the other 5- to 8-membered aromatic heterocycle(s), and wherein the group may be bonded at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzoimidazolyl, 2-benzoimidazolyl, 4-benzoimidazolyl, 5-benzoimidazolyl), dibenzofuryl, benzoxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), purinyl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl), or the like.

"Heterocycle" and "heterocyclic ring" mean a ring from which the above heterocyclic group can be derived.

"Spiro cycle" means a ring constituted two rings sharing a carbon atom. Two rings may be each independently carbocycle or heterocycle.

"Heterocyclic lower alkyl" and "heterocyclyl lower alkyl" mean lower alkyl substituted with the above "heterocyclic group".

"Heterocyclyloxy" means an oxy attached to the above "heterocyclic group".

"Lower alkoxy" or "alkoxy" mean an oxy attached to the above "lower alkyl" or "alkoxy", such as methoxy, ethoxy, n-propoxy, isopropoxy, n-butoxy, isobutoxy, tert-butoxy, and the like.

"Lower alkylcarbonyl", "cycloalkylcarbonyl", "cycloalkyl lower alkylcarbonyl", "lower alkoxycarbonyl", "arylcarbonyl", "aryl lower alkylcarbonyl", "aryloxycarbonyl", "heterocyclylcarbonyl", "heterocyclyl lower alkylcarbonyl", and "heterocyclyloxycarbonyl" means a carbonyl attached to the above "lower alkyl", "cycloalkyl", "cycloalkyl lower alkyl", "lower alkoxy", "aryl", "aryl lower alkyl", "aryloxy", "heterocyclic group", and "heterocyclyl lower alkyl", respectively.

"Lower alkylsulfonyl" means the alkyl part of a lower alkylsulfonyl is the above "lower alkyl", such as methylsulfonyl, and the like.

When a substituent(s) is/are present on "substituted or unsubstituted lower alkyl", "substituted or unsubstituted cycloalkyl", "substituted or unsubstituted cycloalkyl lower alkyl", "substituted or unsubstituted lower alkenyl", "substituted or unsubstituted lower alkynyl", "substituted or unsubstituted lower alkoxy", "substituted or unsubstituted aryl", "substituted or unsubstituted aryl lower alkyl", "substituted or unsubstituted aryloxy", "substituted or unsubstituted heterocycle", "substituted or unsubstituted heterocyclic group", "substituted or unsubstituted heterocyclyl lower alkyl", "substituted or unsubstituted heterocyclyloxy", "substituted or unsubstituted lower alkenyloxy", "substituted or unsubstituted lower alkylcarbonyl", "substituted or unsubstituted cycloalkylcarbonyl", "substituted or unsubstituted cycloalkyl lower alkylcarbonyl", "substituted or unsubstituted lower alkoxycarbonyl", "substituted or unsubstituted arylcarbonyl", "substituted or unsubstituted aryl lower alkylcarbonyl", "substituted or unsubstituted aryloxycarbonyl", "substituted or unsubstituted heterocyclylcarbonyl", "substituted or unsubstituted heterocyclyl lower alkylcarbonyl", "substituted or unsubstituted heterocyclyloxycarbonyl", "substituted or unsubstituted lower alkylene", "substituted or unsubstituted lower alkenylene", "substituted or unsubstituted phosphoric acid residue", "substituted or unsubstituted carbocycle", "substituted or unsubstituted lower alkylsulfonyl", "substituted or unsubstituted spiroring", "substituted or unsubstituted (C2-C4)bridge" or the like, each may be substituted with the same or different, 1 to 4 group(s) selected from Substituent group B and Substituent group A (described below) at any position.

Examples of Substituent group B include hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy), lower alkenyloxy (e.g., vinyloxy, allyloxy), lower alkoxycarbonyl (e.g., methoxycarbonyl, ethoxycarbonyl, tert-butoxycarbonyl), nitro, nitroso, substituted or unsubstituted amino (e.g., alkylamino (e.g., methylamino, ethylamino, dimethylamino), acylamino (e.g., acetylamino, benzoylamino), aralkylamino (e.g., benzylamino, tritylamino), hydroxyamino)), azido, aryl (e.g., phenyl), aralkyl (e.g., benzyl), cyano, isocyano, isocyanato, thiocyanato, isothiocyanato, mercapto, alkylthio (e.g., methylthio), alkylsulfonyl (e.g., methanesulfonyl, ethanesulfonyl), substituted or unsubstituted alkylsulfonylamino (e.g., methanesulfonyl amino, ethanesulfonylamino, N-methylsulfonyl-N'-methylamino), substituted or unsubstituted carbamoyl (e.g., alkylcarbamoyl (e.g., methylcarbamoyl, ethylcarbamoyl, dimethylcarbamoyl)), sulfamoyl, acyl (e.g., formyl, acetyl), formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, phosphoric acid residue, phosphoric-acid-residue-substituted lower alkyl (which may be having a heteroatom group(s)), aryl substituted with a phosphoric acid residue, aralkyl substituted with a phosphoric acid residue, hydroxy lower alkyl and the like, more preferably hydroxy, carboxy, halogen (F, Cl, Br, I), halo lower alkyl (e.g., $CF_3$, $CH_2CF_3$, $CH_2CCl_3$), halo lower alkoxy (e.g., $OCF_3$, $OCH_2CF_3$, $OCH_2CCl_3$), lower alkyl (e.g., methyl, ethyl, isopropyl, tert-butyl), lower alkoxy (e.g., methoxy, ethoxy, propoxy, butoxy), substituted or unsubstituted amino (e.g., alkylamino (e.g., methylamino, ethylamino, dimethylamino), oxo, phosphoric acid residue, and the like.

Examples of a substituent(s) of "substituted or unsubstituted amino", "substituted or unsubstituted carbamoyl", "substituted or unsubstituted aminocarbonyl", "substituted or unsubstituted ureido" or "substituted or unsubstituted thioureido" include mono- or di-lower alkyl, lower alkylcarbonyl, or lower alkylsulfonyl, substituted or unsubstituted lower alkyl (e.g., methyl, ethyl, isopropyl, benzyl, carbamoylalkyl (e.g., carbamoylmethyl), mono- or di-lower alkylcarbamoyl lower alkyl (e.g., dimethylcarbamoylethyl), hydroxy lower alkyl, heterocyclyl lower alkyl (e.g., morpholinoethyl, tetrahydropyranylethyl), alkoxycarbonyl lower alkyl (e.g., ethoxycarbonylmethyl, ethoxycarbonylethyl), mono- or di-lower alkylamino lower alkyl (e.g., dimethylaminoethyl)), lower alkoxy lower alkyl (e.g., methoxyethyl, ethoxymethyl, ethoxyethyl, isopropoxyethyl, and the like), acyl (e.g., formyl, substituted or unsubstituted lower alkylcarbonyl (e.g., acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl), lower alkoxy lower alkylcarbonyl (e.g., methoxyethylcarbonyl), lower alkylcarbamoyl lower alkylcarbonyl (e.g., methylcarbamoylethylcarbonyl), alkoxycarbonylacetyl), substituted or unsubstituted arylcarbonyl (e.g., benzoyl, toluoyl), substituted or unsubstituted aralkyl (e.g., benzyl, 4-fluorobenzyl), hydroxy, substituted or unsubstituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl substituted or unsubstituted with lower alkyl or halogen (e.g., benzenesulfonyl, toluenesulfonyl, 4-fluorobenzenesulfonyl), cycloalkyl (e.g., cyclopropyl), aryl substituted or unsubstituted with lower alkyl (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), substituted or unsubstituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), substituted or unsubstituted amino (e.g., mono- or di-alkylamino (e.g., dimethylamino), formylamino), and the like.

As to an amino group of "substituted or unsubstituted amino", "substituted or unsubstituted aminocarbonyl", or "substituted or unsubstituted carbamoyl", two substituents on the amino group together with the adjacent nitrogen atom may form a nitrogen-containing heterocycle which may contains sulfur and/or oxygen atoms in the ring (preferably 5- to 7-membered ring, also preferably saturated ring) and the ring is substituted or unsubstituted with oxo or hydroxy. A 5- or 6-membered ring and the like such as piperazinyl, piperidino, morpholino, pyrrolidino, 2-oxopiperidino, 2-oxopyrrolidino, 4-hydroxymorpholino and the like are preferred.

"Phosphoric acid residue" means a group represented by the formula: $—PO(OH)_2$. "Substituted or unsubstituted phosphoric acid residue" means a phosphoric acid residue in which the OH part and/or hydrogen of the OH may be substituted.

More Preferred Embodiments

Q is a carbocyclic group that is optionally substituted and optionally condensed or a heterocyclic group that is optionally substituted and optionally condensed.

Q is preferably a substituted or unsubstituted heterocyclic group.

Q is more preferably a 5- to 7-membered monocyclic heterocyclic group that is optionally substituted and contains one to four heteroatoms that are one or the same or different, two or more heteroatoms selected from O, S, and N atoms. Q is, further preferably, a monocyclic aromatic heterocyclic group containing one to three of the heteroatoms, particularly preferably, a 5-membered ring, and most preferably, a 5-membered monocyclic aromatic heterocyclic group containing one S atom and one or two N atoms. Preferred Q is, specifically, a ring shown below:

[Chemical Formula 29]

(1) 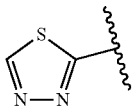

(2) 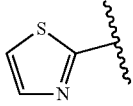

(3) 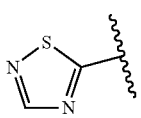

(4) 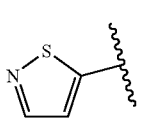

(5) 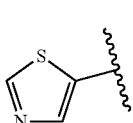

(6) 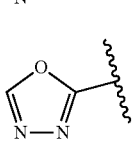

(7) 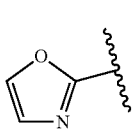

(8) 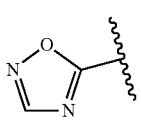

(9) 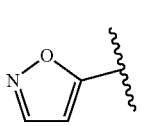

(10) 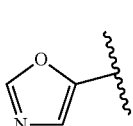

(11) 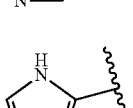

(12) 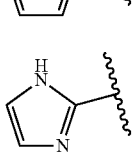

-continued

(13) 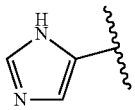

(14) 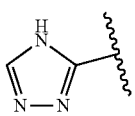

(15) 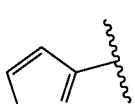

(16) 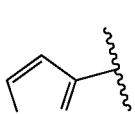

(17) 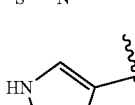

(18) 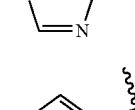

(19) 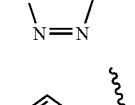

Q is, more preferably, a ring of the above-described (1), (2), (3), (5), (6), (7), (10), (11), (12), (13), (14), (15), (16), or (17) particularly preferably a ring of the above-described (1), (2), (3), (5), or (17) and most preferably a ring of the above-described (1), (2), or (17).

Examples of a condensed ring of the above-described monocyclic heterocyclic group include a benzene ring and other monocyclic heterocycle (preferably 5- to 7-membered).

Q is more preferably a carbocyclyl or heterocyclyl substituted with the same or different, one to four, further preferably one or two, substituent(s) selected from Substituent group A.

Substituent group A: lower alkyl (e.g., methyl, ethyl), lower alkoxy (e.g., methoxy, ethoxy), halogen (e.g., F, Br), halogenated lower alkyl (e.g., —CH$_2$F, —CHF$_2$, —CF$_3$, —CH$_2$CH$_2$F, —CH$_2$CHF$_2$, —CH$_2$CF$_3$), halogenated lower alkoxy (e.g., —OCH$_2$F, —OCHF$_2$, —OCF$_3$, —OCH$_2$CH$_2$F, —OCH$_2$CHF$_2$, —OCH$_2$CF$_3$), and a group represented by the formula:

[Chemical Formula 30]

(B) 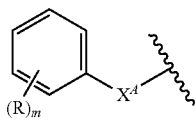

in the above formula,
$X^A$ is a group selected from the following group:
$X^{A1}$: a single bond;
$X^{A2}$: a group selected from C(=O) and C(=S);
$X^{A3}$: a heteroatom group selected from O, S, SO, SO$_2$, and N(R$^{1'}$) wherein R$^{1'}$ is hydrogen or lower alkyl;
$X^{A4}$: a group formed by linking the same or different, two or more groups selected from $X^{A2}$ and $X^{A3}$ (e.g., —CONH—, —CONHNH—, —CONHNHCO—, —CONHO—, —CONHNHSONH—, —CONHNMe-, —NHCONH—, —NHCOO—);
$X^{A5}$: a group selected from —N=N—, —C(R$^{1'}$)=N—, or —N=C(R$^{1'}$)— wherein R$^{1'}$ is hydrogen or lower alkyl;
$X^{A6}$: substituted or unsubstituted lower alkylene or substituted or unsubstituted lower alkenylene (example of substituent: methyl, phenyl);
$X^{A7}$: $X^{A6}$ intervened by one or any two or more groups selected from $X^{A2}$, $X^{A3}$, $X^{A4}$, and $X^{A5}$ (e.g., —CONHCH$_2$—, —CONMeCH$_2$—, —CONHCH$_2$CH$_2$O—, —CONHCH$_2$CH$_2$—SO$_2$—, CONHCH$_2$CH$_2$CH$_2$—);
$X^{A8}$: a group CR$^{1'}$R$^{2'}$ wherein R$^{1'}$ and R$^{2'}$ are taken together with neighboring atoms to form carbocycle (e.g., cyclopropyl, cyclobutyl, cyclopentyl, cyclohexyl) or heterocycle (e.g., oxetane, oxolane); and
$X^{A9}$: a spacer consisting of any combination of $X^{A1}$ to $X^{A7}$.

In $X^A$, "intervene" may be any of cases where one or any two or more groups selected from $X^{A2}$, $X^{A3}$, $X^{A4}$, and $X^{A5}$ 1) are present between carbon atoms constituting lower alkylene or lower alkenylene, 2) are present at an end of lower alkylene or lower alkenylene, and where 1) and 2) coexist.

$X^A$ is a spacer consisting of, preferably, one to five atoms linked, and more preferably, one to three atoms linked. $X^A$ is more preferably lower alkylene, and further preferably C1-C3 alkylene.

R is a group independently selected from the following group:
(1) lower alkyl,
(2) lower alkoxy,
(3) halogen,
(4) halogenated lower alkyl,
(5) halogenated lower alkoxy, and
(6) lower cycloalkyl.

R is preferably, independently lower alkoxy, halogen, or halogenated lower alkyl, and more preferably halogen.

m is an integer of 0 to 5, preferably, 1 or 2.

Q is more preferably substituted with a group shown in the above-described (B).

Q is, more preferably, a ring of the above-described (Q1) to (Q30). Particularly preferable Q is (Q1), (Q2), (Q15), (Q21), (Q23), (Q24) or (Q25).

[Chemical Formula 31]

(Q1)

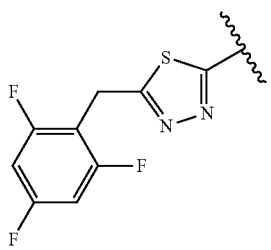

(Q2)

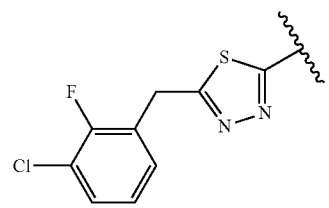

(Q3)

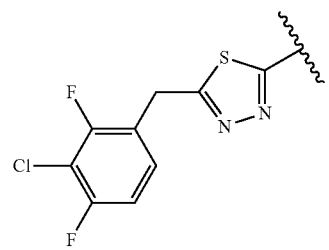

(Q4)

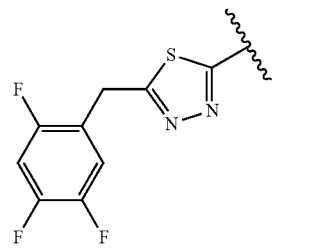

(Q5)

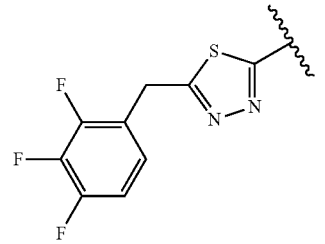

(Q6)

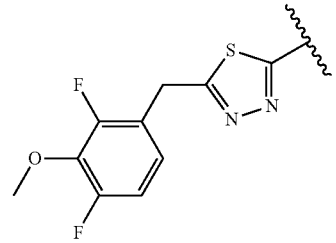

(Q7)

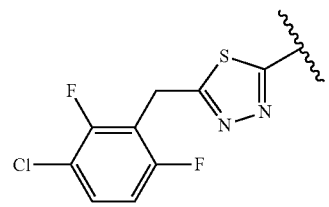

(Q8)
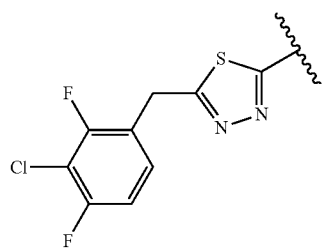
(Q9)
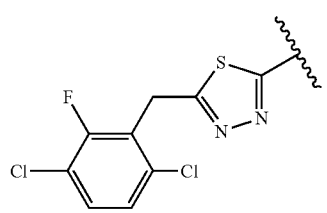
(Q10)
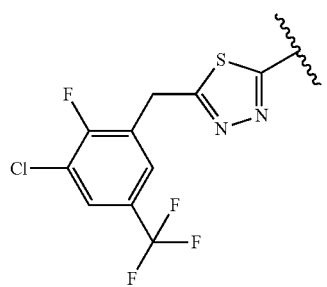
(Q11)
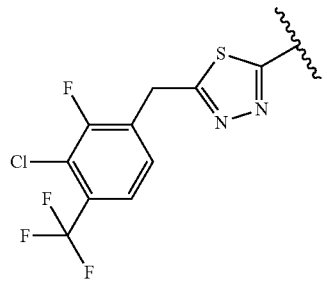
(Q12)
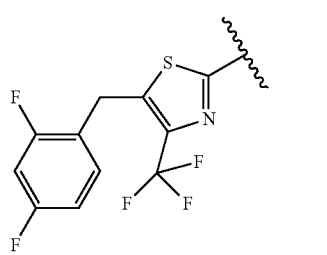
(Q13)
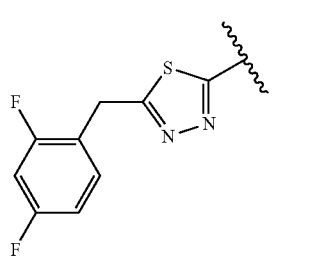
(Q14)
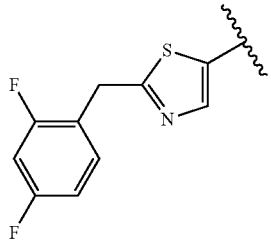
(Q15)
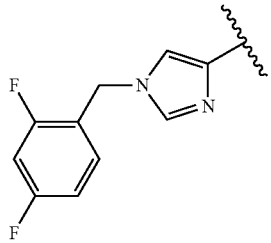
(Q16)
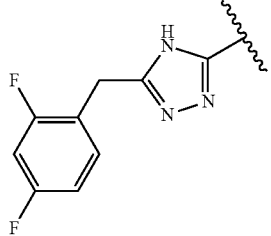
(Q17)
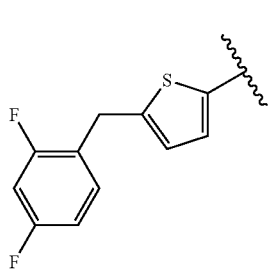
(Q18)
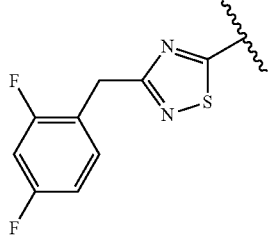
(Q19)
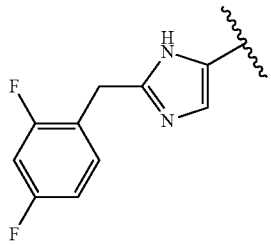

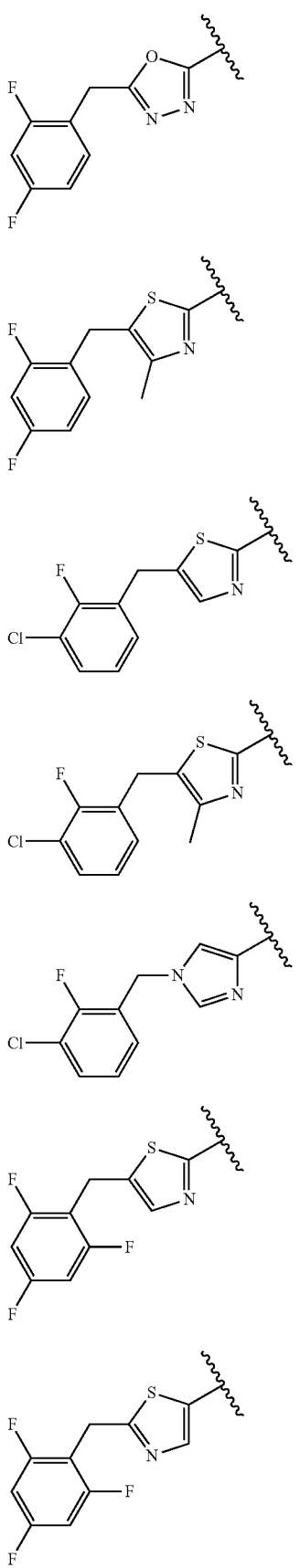
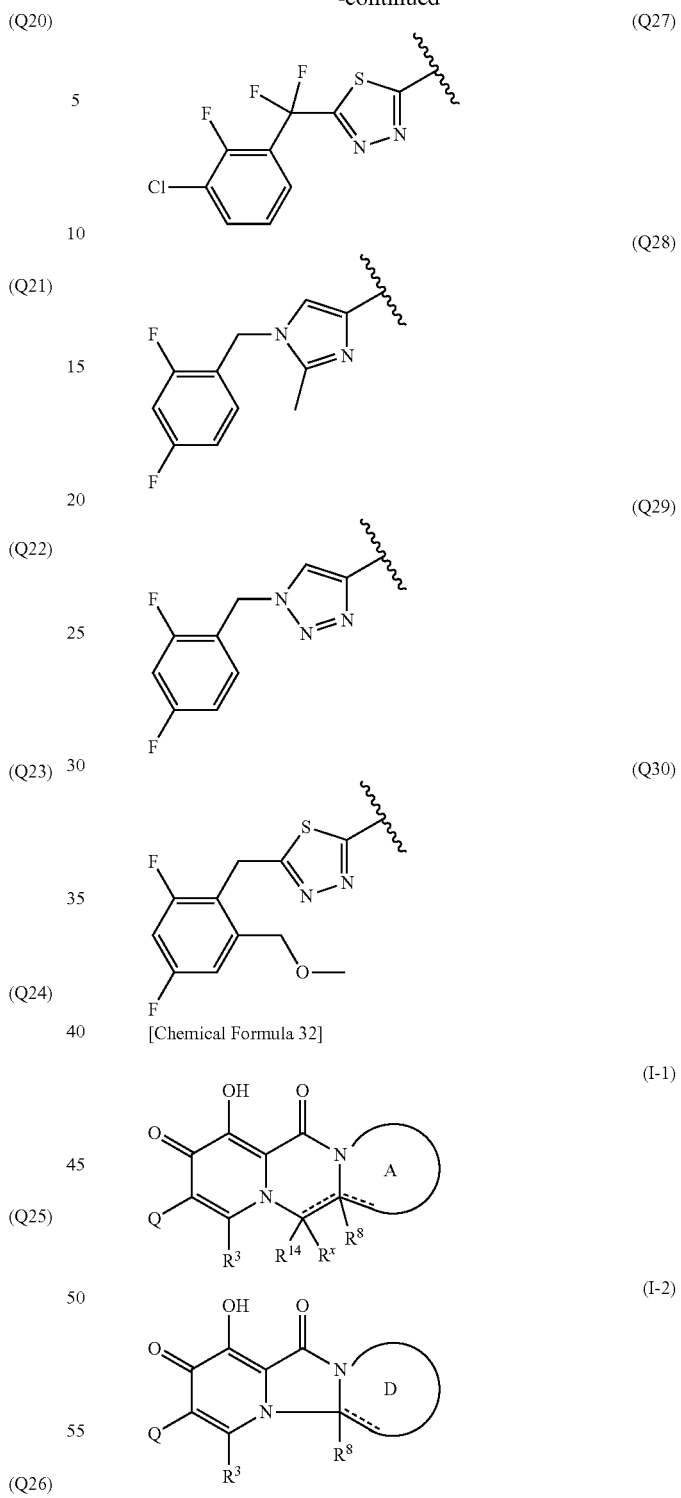

R³ may be a variety of substituents as far as they do not adversely affect on the pharmacological activity of the present compound. Examples thereof include, for example, hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy or substituted or unsubstituted amino, and the like. Examples of a substituent(s) in the "substituted or unsubstituted" on $R^3$ include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like. More preferred are halogen, hydroxy, amino, lower alkylamino, lower alkyl, lower alkoxy, and the like.

$R^3$ is more preferably, hydrogen, halogen, hydroxy, lower alkyl, lower alkenyl, lower alkoxy, lower alkenyloxy or amino, further preferably, hydrogen or lower alkyl (e.g., methyl), and particularly preferably, hydrogen.

The broken line represents the presence or absence of a bond.

When the broken line adjacent to the carbon atom connected with $R^x$ represents the presence of a bond, $R^x$ is absence.

When the broken line adjacent to the carbon atom connected with $R^8$ represents the presence of a bond, $R^8$ is absence.

Both the broken lines adjacent to the carbon atom connected with $R^8$ cannot represent the presence of a bond at the same time.

The A ring is a substituted or unsubstituted heterocycle containing at least one N atom. The substituent on the A ring may be selected from the Substituent group S2, and preferably, the substituent on the A ring is lower alkyl. The heterocycle is preferably a 5- to 7-membered ring containing one to three, preferably two or three, O, S and/or N atoms, and more preferably is selected from the foregoing heterocycles. The A ring is preferably a ring of (a), (b) or (c), more preferably a ring of (a) or (b), and particularly preferably a ring of (b).

[Chemical Formula 33]

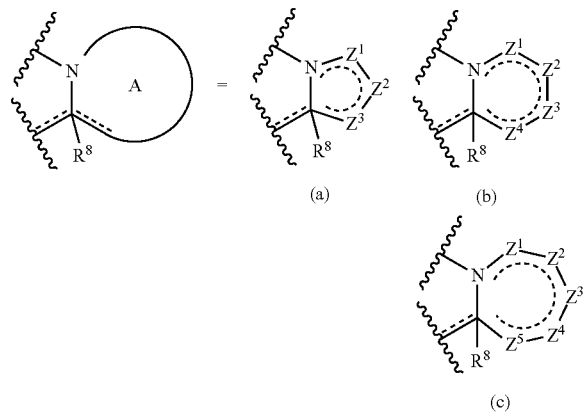

$Z^1$ is preferably, $CR^1R^2$, O, S or $NR^{19}$, and more preferably is $CR^1R^2$.

$Z^2$ is preferably, $CR^1R^2$, O, S or $NR^{19}$, and more preferably is $CR^1R^2$.

$Z^3$ is preferably, $CR^1R^2$, O, S or $NR^{19}$, and more preferably is $CR^1R^2$ or O.

$Z^4$ is preferably, $CR^1R^2$, O, S or $NR^{19}$, and more preferably is $CR^1R^2$, O or $NR^{19}$, and particularly preferably is $CR^1R^2$ or O.

$Z^5$ is preferably, $CR^1R^2$, O, S or $NR^{19}$, and more preferably is $CR^1R^2$ or O.

$Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ may be taken together to form substituted or unsubstituted (C2-C4) bridge (example of substituent: lower alkyl, hydroxy, halogen).

$R^1$ and $R^2$ may be a variety of substituents as far as they do not adversely affect on the pharmacological activity of the present compound. Examples thereof include, for example, each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue or lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N═ and ═N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido, preferably, hydrogen, halogen, hydroxy, substituted or unsubstituted lower alkyl, substituted or unsubstituted cycloalkyl, and the like.

Examples of a substituent(s) in the "substituted or unsubstituted" on $R^1$ and $R^2$ include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like. $R^1$ and $R^2$ are, more preferably, each independently, hydrogen, halogen, hydroxy, lower alkyl, lower alkenyl, lower alkoxy, lower alkenyloxy or substituted or unsubstituted amino, further preferably, each independently, hydrogen or lower alkyl (e.g., methyl), particularly preferably, hydrogen.

$R^1$ and $R^2$ may be taken together to form oxo, thioxo or substituted or unsubstituted spiro ring (example of substituent: lower alkyl, halogen, halogenated lower alkyl, hydroxy, amino), preferably, oxo or unsubstituted spiro ring.

$R^{19}$ is preferably, 1) hydrogen, 2) substituted or unsubstituted lower alkyl (example of substituent: amino substituted or unsubstituted with mono- or di-lower alkyl, cycloalkyl, hydroxy, an substituted or unsubstituted heterocyclic group (wherein the heterocycle is preferably a 5- to 7-membered ring; example: furyl, thienyl, thiazolyl, pyridyl, morpholino, imidazole; example of substituent: lower alkyl, halogen), substituted or unsubstituted heterocyclylcarbonyl (wherein the heterocycle is preferably a 5- to 7-membered ring; example: morpholinocarbonyl), substituted or unsubstituted phenyl (substituent: lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, mono- or di-lower alkyl-substituted carbamoyl, lower alkylsulfonylamino, lower alkoxy, carbonyl, halogen, thiol, lower alkylthio), 3) lower alkenyl, 4)acyl (e.g., lower alkylcarbonyl), or 5) lower alkylsulfonyl. $R^{19}$ may be selected from the Substituent group S2 described below.

Further, A ring may have E ring as the following. In this case, $Z^1$, $Z^2$, $Z^3$, $Z^4$ and $Z^5$ constituting E ring are each independently, $CR^1$, C or N.

[Chemical Formula 34]

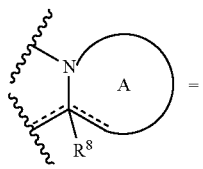
(a)

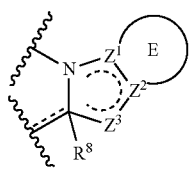
(b)

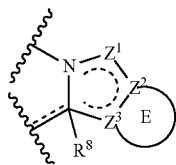
(c)

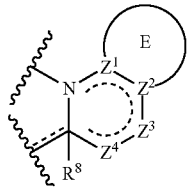
(d)

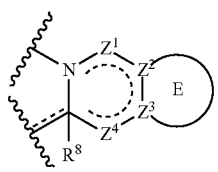
(e)

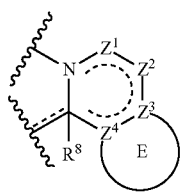

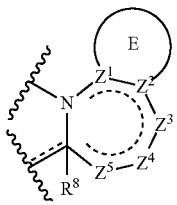
(f)

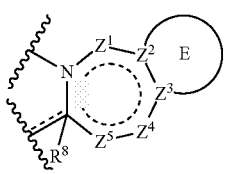
(g)

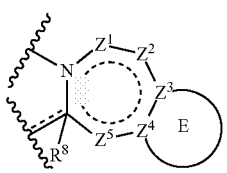
(h)

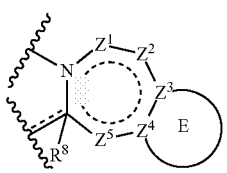
(i)

A ring is more preferably, the ring of (a) or (b), particularly preferably, the ring of (b).

E ring is preferably, substituted or unsubstituted 4- to 7-membered carbocycle (example of substituent: lower alkyl, halogen, hydroxy, halogenated lower alkyl) or substituted or unsubstituted 4- to 7-membered heterocycle (example of substituent: lower alkyl, halogen, hydroxy, halogenated lower alkyl), more preferably, 5- to 6-membered unsubstituted carbocycle or 5- to 6-membered unsubstituted heterocycle, particularly preferably, 5-membered unsubstituted carbocycle or 5-membered unsubstituted heterocycle.

Substituent group S2: hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted phosphoric acid residue, aryl substituted with substituted or unsubstituted phosphoric acid residue, aralkyl substituted with substituted or unsubstituted phosphoric acid residue, hydroxy substituted with substituted or unsubstituted phosphoric acid residue, amino substituted with substituted or unsubstituted phosphoric acid residue, or lower alkyl substituted with substituted or unsubstituted phosphoric acid residue (A heteroatom group selected from the group consisting of CO, O, S, SO, $SO_2$, $NR^5$ ($R^5$ is selected independently from the same substituents group as $R^4$.), —N= and =N— may intervene in the lower alkyl.).

The compound of formula (I-1) is preferably compound represented by the following formula (I-1-1) or (I-2-1), particularly preferably compound represented by formula (I-2-1).

[Chemical Formula 35]

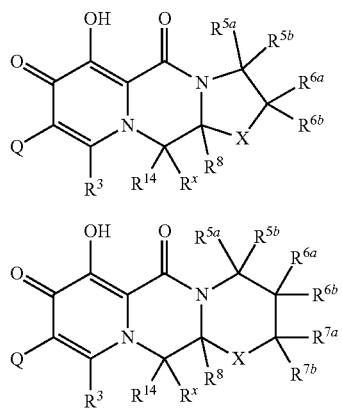

X is $CR^{9a}R^{9b}$, $NR^{10}$, O or S, preferably, $CR^{9a}R^{9b}$, $NR^{10}$ or O, particularly preferably, $CR^{9a}R^{9b}$ or O.

$R^{5a}$, $R^{5b}$, $R^{6a}$, $R^{6b}$, $R^{7a}$, $R^{7b}$, $R^8$, $R^{9a}$, $R^{9b}$ and $R^{10}$ may be a variety of substituents as far as they do not adversely affect on the pharmacological activity of the present compound. Examples thereof include, for example, each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N= and =N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido, preferably, hydrogen, halogen, hydroxy, substituted or unsubstituted lower alkyl, substituted or unsubstituted cycloalkyl, and the like. A substituent(s) in the "substituted or unsubstituted" on $R^{5a}$, $R^{5b}$, $R^{6a}$, $R^{6b}$, $R^{7a}$, $R^{7b}$, $R^8$, $R^{9a}$, $R^{9b}$ and $R^{10}$ are halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

$R^{5a}$, $R^{5b}$, $R^{6a}$, $R^{6b}$, $R^{7a}$, $R^{7b}$, $R^8$, $R^{9a}$, $R^{9b}$ and $R^{10}$ are more preferably, each independently, hydrogen, halogen, hydroxy, lower alkyl, lower alkenyl, lower alkoxy, lower alkenyloxy or substituted or unsubstituted amino, further preferably, each independently, hydrogen or lower alkyl (e.g., methyl).

$R^{5a}$ and $R^{5b}$, $R^{6a}$ and $R^{6b}$, $R^{7a}$ and $R^{7b}$, and/or $R^{9a}$ and $R^{9b}$ may be taken together to form oxo, thioxo or substituted or unsubstituted spiro ring (example of substituent: halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy), preferably, oxo or 3- to 5-membered unsubstituted spiro ring.

$R^{5b}$ and $R^{6b}$, $R^{6b}$ and $R^{7b}$ and/or $R^{7b}$ and $R^{9b}$ may be taken together with neighboring atoms to form substituted or unsubstituted carbocycle or substituted or unsubstituted heterocycle, and/or $R^{5b}$ and $R^{7b}$, $R^{5b}$ and $R^8$, $R^{5b}$ and $R^{9b}$, $R^{6b}$ and $R^8$, $R^{6b}$ and $R^{9b}$ or $R^{7b}$ and $R^8$ may be taken together to form substituted or unsubstituted (C2-C4) bridge, $R^{5b}$ and $R^{10}$ may be taken together with neighboring atoms to form substituted or unsubstituted heterocycle, or $R^{6b}$ and $R^{10}$, or $R^{7b}$ and $R^{10}$ may be taken together to form substituted or unsubstituted (C2-C4) bridge.

Example of substituent of "substituted or unsubstituted carbocycle", "substituted or unsubstituted heterocycle" or "substituted or unsubstituted (C2-C4) bridge" is halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

$R^x$ is hydrogen or substituted or unsubstituted lower alkyl, preferably, hydrogen.

The compound of formula (I-1) is, further preferably, the compound represented by any following formula.

[Chemical Formula 36]

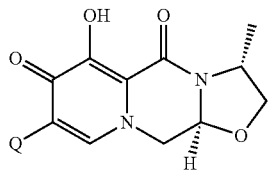

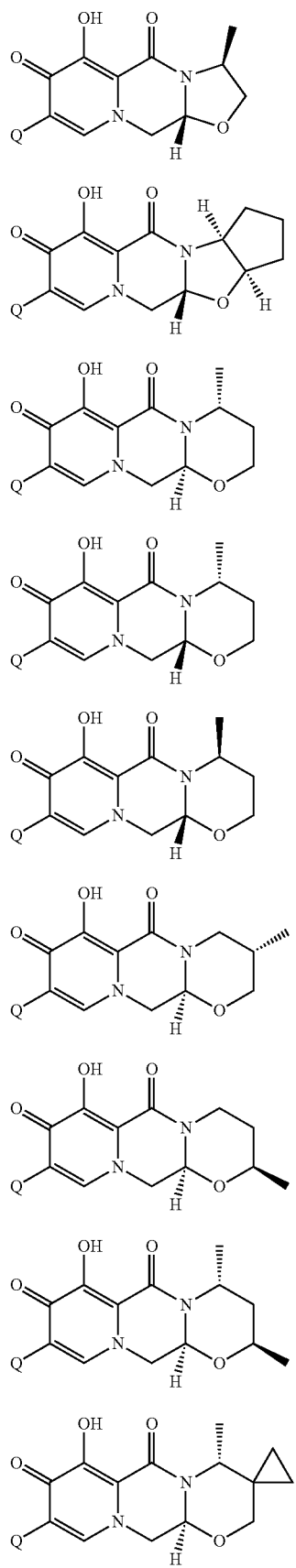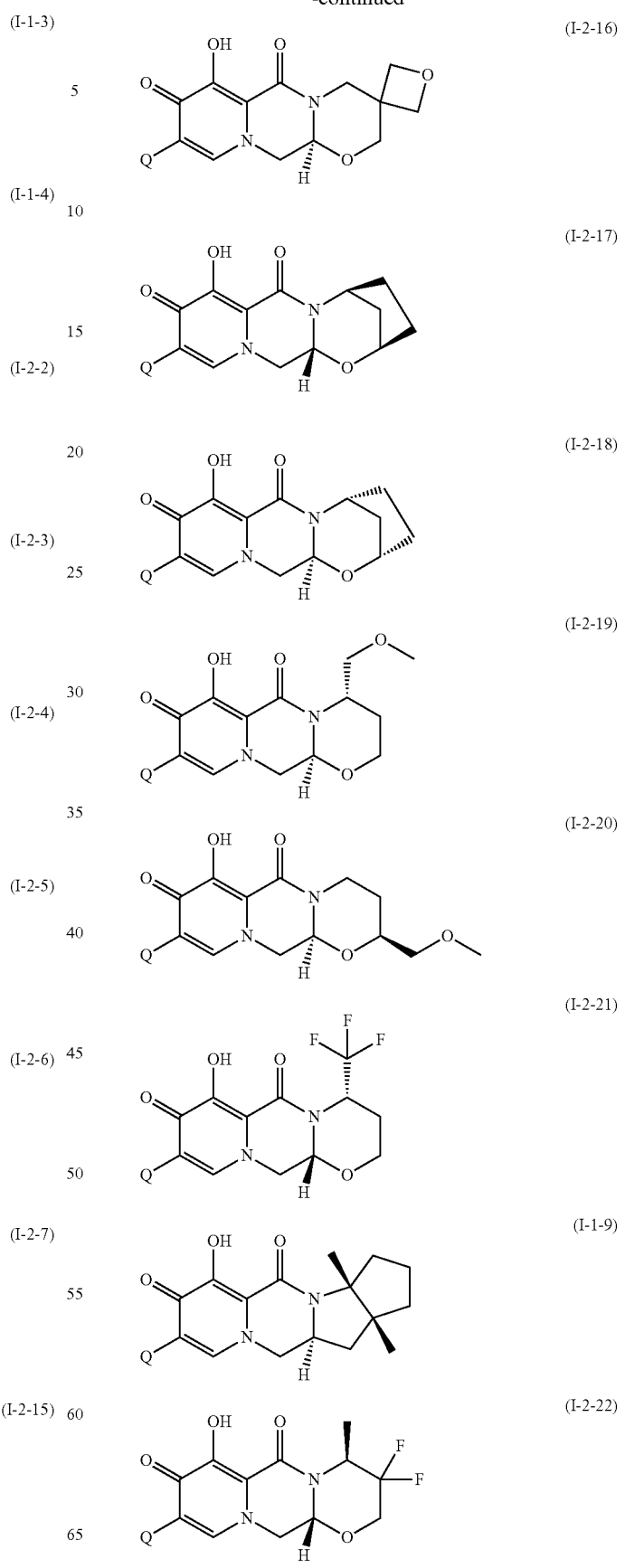

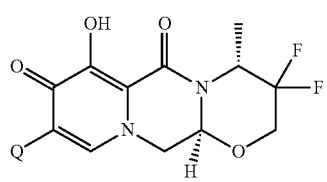
(I-2-23)
[Chemical Formula 37]
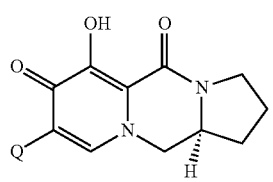
(I-1-5)
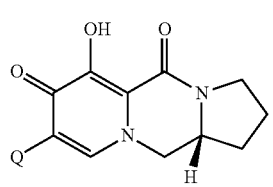
(I-1-6)
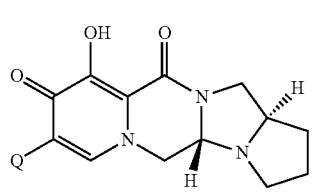
(I-1-7)
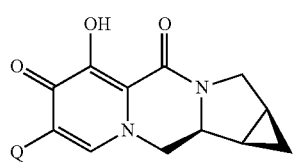
(I-1-8)
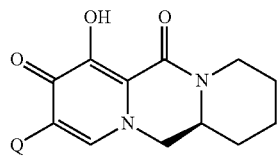
(I-2-8)
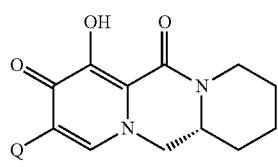
(I-2-9)
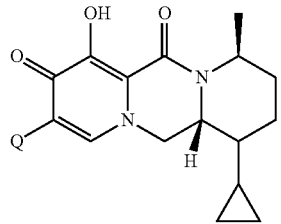
(I-2-10)
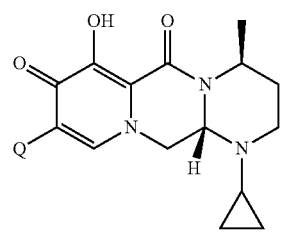
(I-2-11)
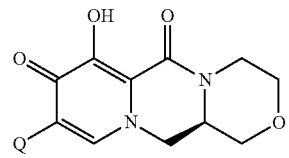
(I-2-12)
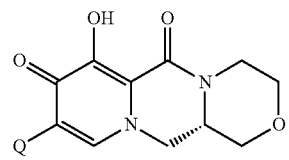
(I-2-13)
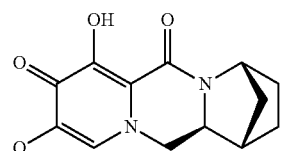
(I-2-14)
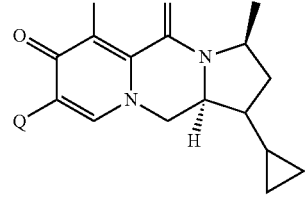
(I-1-10)
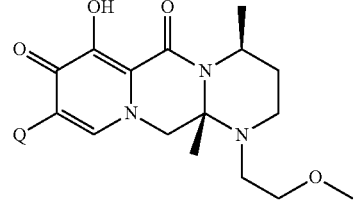
(I-2-24)
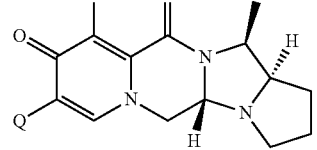
(I-1-11)
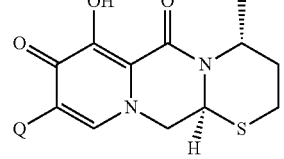
(I-2-25)

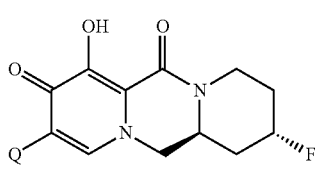

(I-2-26)

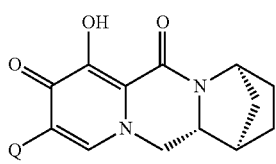

(I-2-27)

[Chemical Formula 38]

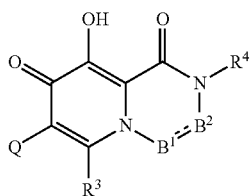

(I-3)

When either one of $B^1$ and $B^2$ is $CR^{20}R^{21}$ and the other is $NR^{22}$, preferably $B^1$ is $CR^{20}R^{21}$, $B^2$ is $NR^{22}$.

When $B^2$ is $NR^{22}$, $R^4$ and $R^{22}$ may be taken together with neighboring atoms to form substituted or unsubstituted heterocycle (e.g., F ring).

When $B^1$ is $CR^{20}R^{21}$ and $B^2$ is $NR^{22}$, or $B^1$ is $NR^{22}$ and $B^2$ is $CR^{20}R^{21}$, $R^{20}$ and $R^{22}$ may be taken together with neighboring atoms to form substituted or unsubstituted heterocycle (e.g., G ring). When $B^2$ is $CR^{20}R^{21}$, $R^4$ and $R^{21}$ may be taken together with neighboring atom to form substituted or unsubstituted heterocycle.

When either one of $B^1$ and $B^2$ is $CR^{23}$ and the other is N, the broken line represents the presence of a bond; when $B^2$ is $CR^{23}$, $R^4$ and $R^{23}$ may be taken together with neighboring atoms to form substituted or unsubstituted heterocycle.

$B^1$ and $B^2$ are each independently $CR^{20}R^{21}$ or $CR^{23}$.

$R^3$ is hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy or substituted or unsubstituted amino. Examples of a substituent(s) in the "substituted or unsubstituted" on $R^3$ include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

$R^3$ is more preferably, hydrogen, halogen, hydroxy, lower alkyl, lower alkenyl, lower alkoxy, lower alkenyloxy or amino, further preferably, hydrogen or lower alkyl (e.g., methyl), particularly preferably, hydrogen.

$R^4$ is hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, hydroxy, substituted or unsubstituted amino, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue or lower alkyl substituted with substituted or unsubstituted phosphoric acid residue (A heteroatom group selected from the group consisting of CO, O, S, SO, $SO_2$, $NR^a$ ($R^a$ is hydrogen or lower alkyl), —N= and =N— may intervene in the lower alkyl.), more preferably, hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted aryl, substituted or unsubstituted aryl lower alkyl, substituted or unsubstituted heterocyclyl or substituted or unsubstituted heterocyclyl lower alkyl.

$R^4$ is, preferably, substituted or unsubstituted lower alkyl (e.g., methyl, ethyl, n-propyl, i-propyl, n-butyl; example of substituent: hydroxy, amino, lower alkylamino, lower alkoxy, aryloxy, oxo, lower alkoxycarbonyl, substituted or unsubstituted heterocyclylcarbonyl (example of substituent: lower alkyl, lower alkoxy)), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl) or aryloxy lower alkyl (e.g., 2-phenoxyethyl, 3-phenoxypropyl); substituted or unsubstituted cycloalkyl (e.g., cyclopropyl); substituted or unsubstituted cycloalkyl lower alkyl (e.g., cyclopropylmethyl, 1-adamantylmethyl, 2-adamantylmethyl, dodecahedranemethyl, cubanemethyl); substituted or unsubstituted aryl (e.g., phenyl; example of substituent: lower alkyl, halogen, lower alkyloxy, nitro; or a substituent part may be lower alkylene that may be intervened by a heteroatom (e.g., O)); substituted or unsubstituted aryl lower alkyl (e.g., benzyl; example of substituent: lower alkyl, halogen, lower alkyloxy, nitro; or a substituent part may be lower alkylene that may be intervened by a heteroatom (e.g., O)); an substituted or unsubstituted heterocyclic group (preferably 5- to 6-membered ring) (e.g., picolyl, pyridyl; example of substituent: lower alkyl, halogen, lower alkyloxy, nitro); or an substituted or unsubstituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

$R^{20}$, $R^{21}$, $R^{22}$ and $R^{23}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N= and =N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido.

$R^{20}$, $R^{21}$, $R^{22}$ and $R^{23}$ are preferably, each independently, hydrogen, substituted or unsubstituted lower alkyl (example of substituent: amino, lower alkylamino, lower carbonylamino, lower alkoxy, aryloxy, cyano, halogen, acylamino (e.g., lower carbonylamino), lower alkynyl, hydroxy, lower alkoxycarbonyl, substituted or unsubstituted heterocyclylcarbonyl (example of substituent: lower alkyl, lower alkoxy), lower alkenyl, substituted or unsubstituted carbamoyl (example of substituent: lower alkyl), lower alkylcarbonyloxy, lower alkyloxycarbonyl, lower alkylcarbonylamino, oxo, lower alkynyl), cycloalkyl, cycloalkyl lower alkyl, substituted or unsubstituted aryl (example of substituent: lower alkyl, halogen, lower alkyloxy, nitro), substituted or unsubstituted aryl lower alkyl (example of substituent: lower alkyl, halogen, lower alkyloxy, nitro, oxo), substituted or unsubstituted heterocyclyl (example of substituent: lower alkyl, halogen, lower alkyloxy, nitro), substituted or unsubstituted heterocyclyl lower alkyl (example of substituent: lower alkyl, halogen, lower alkyloxy, nitro, oxo), substituted or unsubstituted lower alkylcarbonyl (substituent: lower alkoxy, halogen), cycloalkylcarbonyl, substituted or unsubstituted benzoyl (substituent: lower alkoxy, halogen), substituted sulfonyl (substituent: lower alkyl, aryl, heterocyclyl (preferably 5- to 6-membered aromatic heterocyclyl)).

$R^{20}$ and $R^{21}$ are more preferably, hydrogen.

The broken line represents the presence or absence of a bond, more preferably, represents the absence of a bond.

When $B^1$ is $NR^{22}$, the broken line represents the absence of a bond, the compound whose $R^4$ is unsubstituted ethyl or unsubstituted isopropyl are excluded from the present compound.

[Chemical Formula 39]

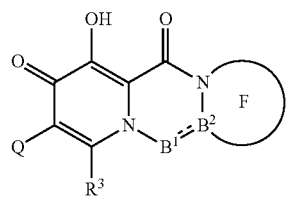

(I-3-1)

$B^1$ and $B^2$ are defined at the same as formula (I-3).

F ring is substituted or unsubstituted heterocycle, preferably, the following 5- to 7-membered substituted or unsubstituted heterocycle.

[Chemical Formula 40]

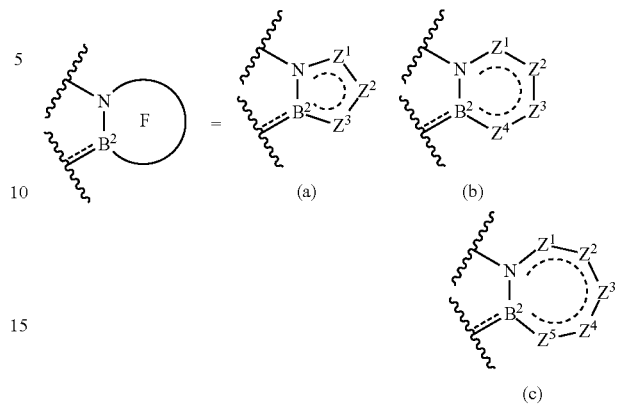

(a) (b)

(c)

$Z^1$, $Z^2$, $Z^3$, $Z^4$ and $Z^5$ are each independently, $CR^1R^2$, $CR^1$, O, S, SO, $SO_2$, N or $NR^{19}$.

$Z^1$ is preferably, $CR^1R^2$, O, S or $NR^{19}$, and more preferably is $CR^1R^2$.

$Z^2$ is preferably, $CR^1R^2$, O, S or $NR^{19}$, and more preferably is $CR^1R^2$.

$Z^3$ is preferably, $CR^1R^2$, O, S or $NR^{19}$, and more preferably is $CR^1R^2$ or O.

$Z^4$ is preferably, $CR^1R^2$, O, S or $NR^{19}$, and more preferably is $CR^1R^2$, O or $NR^{19}$, and particularly preferably is $CR^1R^2$ or O.

$Z^5$ is preferably, $CR^1R^2$, O, S or $NR^{19}$, and more preferably is $CR^1R^2$ or O.

$Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ may be taken together to form substituted or unsubstituted (C2-C4) bridge (example of substituent: lower alkyl, hydroxy, halogen).

$R^1$ and $R^2$ may be a variety of substituents as far as they do not adversely affect on the pharmacological activity of the present compound. Examples thereof include, for example, each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N= and =N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido, preferably, hydrogen, halogen, hydroxy, substituted or unsubstituted lower alkyl, substituted or unsubstituted cycloalkyl, and the like.

Examples of a substituent(s) in the "substituted or unsubstituted" on $R^1$ and $R^2$ include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

$R^1$ and $R^2$ are more preferably, each independently, hydrogen, halogen, hydroxy, lower alkyl, lower alkenyl, lower alkoxy, lower alkenyloxy or substitute d or unsubstituted amino, further preferably, each independently, hydrogen or lower alkyl (e.g., methyl), particularly preferably, hydrogen.

$R^1$ and $R^2$ may be taken together to form oxo, thioxo or substituted or unsubstituted spiro ring (example of substituent: lower alkyl, halogen, halogenated lower alkyl, hydroxy, amino), preferably, oxo or unsubstituted spiro ring.

$R^{19}$ is preferably, 1) hydrogen, 2) substituted or unsubstituted lower alkyl (example of substituent: amino substituted or unsubstituted with mono- or di-lower alkyl, cycloalkyl, hydroxy, an substituted or unsubstituted heterocyclic group (wherein the heterocycle is preferably a 5- to 7-membered ring; example: furyl, thienyl, thiazolyl, pyridyl, morpholino, imidazole; example of substituent: lower alkyl, halogen), substituted or unsubstituted heterocyclylcarbonyl (wherein the heterocycle is preferably a 5- to 7-membered ring; example: morpholinocarbonyl), substituted or unsubstituted phenyl (substituent: lower alkyl, amino, lower alkylamino, hydroxy, halogen, halogenated lower alkyl, lower alkoxy, halogenated lower alkoxy, lower alkylthio, lower alkylsulfonyl), acetylamino, carbamoyl, mono- or di-lower alkyl-substituted carbamoyl, lower alkylsulfonylamino, lower alkoxy, carbonyl, halogen, thiol, lower alkylthio), 3) lower alkenyl, 4) acyl (e.g., lower alkylcarbonyl), or 5) lower alkylsulfonyl. $R^{19}$ may be selected from the Substituent group S2 described below.

The broken line represents the presence or absence of a bond, preferably represents the absence of a bond.

Further, F ring may have H ring as the following. In this case, $Z^1$, $Z^2$, $Z^3$, $Z^4$ and $Z^5$ constituting 11 ring are each independently, $CR^1$, C or N.

[Chemical Formula 41]

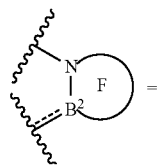

(a)

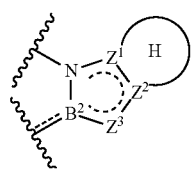

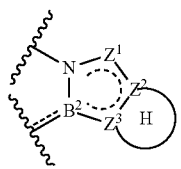

(b)

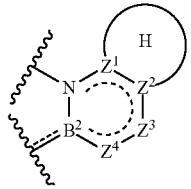

(c)

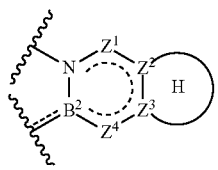

(d)

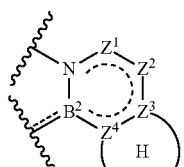

(e)

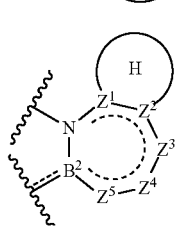

(f)

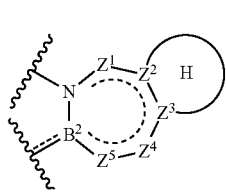

(g)

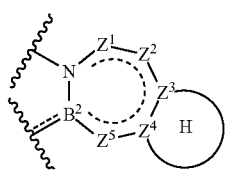

(h)

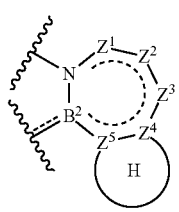

(i)

11 ring is each independently, substituted or unsubstituted carbocycle or substituted or unsubstituted heterocycle, preferably, substituted or unsubstituted 4- to 7-membered carbocycle (example of substituent: lower alkyl, halogen, hydroxy, halogenated lower alkyl) or substituted or unsubstituted 4- to 7-membered heterocycle (example of substituent: lower alkyl, halogen, hydroxy, halogenated lower alkyl), more preferably, 5- to 6-membered unsubstituted carbocycle or 5- to 6-membered unsubstituted heterocycle, particularly preferably, 5-membered unsubstituted carbocycle or 5-membered unsubstituted heterocycle.

[Chemical Formula 42]

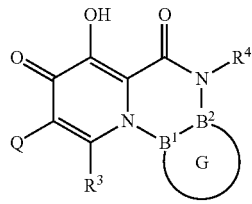

(I-3-2)

G ring is substituted or unsubstituted carbocycle or substituted or unsubstituted heterocycle. $B^1$ is $CR^{21}$ or N. When B is $CR^{21}$, $B^2$ is N. When $B^1$ is N, $B^2$ is $CR^{21}$. The same heterocycle of F ring is exemplified for G ring. The substituent on G ring is the same or different, one to four, further preferably one or two, substituent(s) selected from Substituent group S2. The part of substituent on G ring may be taken together with neighboring atoms to form, further condensed ring or spiro ring, preferably substituted or unsubstituted carbocycle (preferably 5- to 6-membered ring) or substituted or unsubstituted heterocycle (preferably 5- to 6-membered ring).

When G ring is carbocycle, $B^1$ and $B^2$ are each independently C or CH. 5- to 7-membered ring as carbocycle are examplified.

G ring including the following rings.

[Chemical Formula 43]

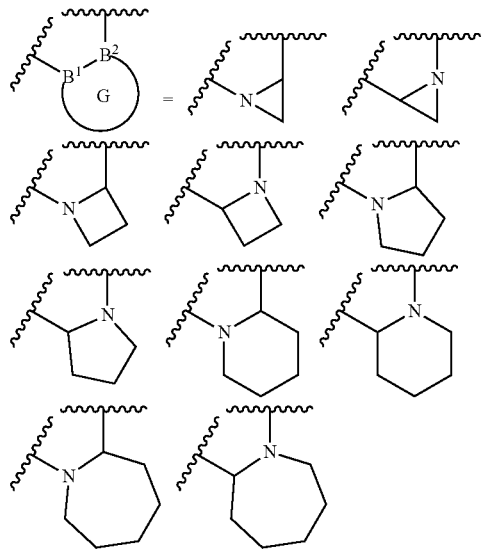

Preferable substituent on G ring is lower alkyl (e.g., methyl, isopropyl), lower alkoxylower alkyl (e.g., 2-methoxyethyl), substituted or unsubstituted amino (example of substituent: lower alkyl (e.g., methyl), lower alkylcarbonyl (e.g., acetyl)).

$R^3$ is preferably, hydrogen or substituted or unsubstituted lower alkyl, more preferably hydrogen.

$R^4$ is, preferably, substituted or unsubstituted lower alkyl (e.g., methyl, ethyl, n-propyl, i-propyl, n-butyl; example of substituent: hydroxy, amino, lower alkylamino, lower alkoxy, aryloxy, oxo, lower alkoxycarbonyl, substituted or unsubstituted heterocyclylcarbonyl (example of substituent: lower alkyl, lower alkoxy)), specifically, lower alkylamino lower alkyl (e.g., 2-dimethylaminoethyl, 2-diethylaminoethyl), lower alkoxy lower alkyl (e.g., 1-methoxyethyl, 2-methoxypropyl, 2-methoxyethyl, 3-methoxypropyl, 4-methoxybutyl, 2-ethoxyethyl, 3-ethoxypropyl, 4-ethoxybutyl, 2-propoxyethyl, 3-propoxypropyl, 4-propoxybutyl) or aryloxy lower alkyl (e.g., 2-phenoxyethyl, 3-phenoxypropyl); substituted or unsubstituted cycloalkyl (e.g., cyclopropyl); substituted or unsubstituted cycloalkyl lower alkyl (e.g., cyclopropylmethyl, 1-adamantylmethyl, 2-adamantylmethyl, dodecahedranemethyl, cubanemethyl); substituted or unsubstituted aryl (e.g., phenyl; example of substituent: lower alkyl, halogen, lower alkyloxy, nitro; or a substituent part may be lower alkylene that may be intervened by a heteroatom (e.g., O)); substituted or unsubstituted aryl lower alkyl (e.g., benzyl; example of substituent: lower alkyl, halogen, lower alkyloxy, nitro; or a substituent part may be lower alkylene that may be intervened by a heteroatom (e.g., O)); an substituted or unsubstituted heterocyclic group (preferably 5- to 6-membered ring) (e.g., picolyl, pyridyl; example of substituent: lower alkyl, halogen, lower alkyloxy, nitro); or an substituted or unsubstituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

[Chemical Formula 44]

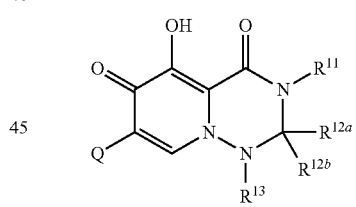

(I-3-3)

$R^{11}$, $R^{12a}$, $R^{12b}$ and $R^{13}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N═ and ═N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido.

$R^{11}$ is preferably, substituted or unsubstituted lower alkyl (e.g., methyl, n-propyl, n-buthyl (proviso ethyl and isopropyl are excluded); example of substituent: hydroxy, amino, lower alkylamino, lower alkoxy, aryloxy, oxo, lower alkoxycarbonyl, substituted or unsubstituted heterocyclylcarbonyl (example of substituent: lower alkyl, lower alkoxy), specifically, lower alkylamino lower alkyl (e.g., 2-dimethylaminoethyl, 2-diethylaminoethyl), lower alkoxylower alkyl (e.g., 1-methoxyethyl, 2-methoxypropyl, 2-methoxyethyl, 3-methoxypropyl, 4-methoxybuthyl, 2-ethoxyethyl, 3-ethoxypropyl, 4-ethoxybuthyl, 2-propoxyethyl, 3-propoxypropyl, 4-propoxybutyl) or aryloxy lower alkyl (e.g., 2-phenoxyethyl, 3-phenoxypropyl); substituted or unsubstituted cycloalkyl (e.g., cyclopropyl); substituted or unsubstituted cycloalkyl lower alkyl (e.g., cyclopropylmethyl, 1-adamantylmethyl, 2-adamantylmethyl, dodecahedranemethyl, cubanemethyl); substituted or unsubstituted aryl (e.g., phenyl; example of substituent: lower alkyl, halogen, lower alkyloxy, nitro; or a substituent part may be lower alkylene that may be intervened by a heteroatom (e.g., O)); substituted or unsubstituted aryl lower alkyl (e.g., benzyl; example of substituent: lower alkyl, halogen, lower alkyloxy, nitro; or a substituent part may be lower alkylene that may be intervened by a heteroatom (e.g., O)); substituted or unsubstituted heterocyclyl (preferably 5- to 6-membered ring) (e.g., picolyl, pyridyl; example of substituent: lower alkyl, halogen, lower alkyloxy, nitro); or an substituted or unsubstituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

$R^{12a}$ and $R^{12b}$ are preferably, each independently, hydrogen, substituted or unsubstituted lower alkyl (example of substituent: amino, lower alkylamino, lower carbonylamino, lower alkoxy, aryloxy, cyano, halogen, acylamino (e.g., lower carbonylamino), lower alkynyl, hydroxy, lower alkoxycarbonyl, substituted or unsubstituted heterocyclylcarbonyl (example of substituent: lower alkyl, lower alkoxy), lower alkenyl, substituted or unsubstituted carbamoyl (example of substituent: lower alkyl), lower alkylcarbonyloxy, lower alkyloxycarbonyl, lower alkylcarbonylamino, oxo, lower alkynyl), cycloalkyl, cycloalkyl lower alkyl, substituted or unsubstituted aryl (example of substituent: lower alkyl, halogen, lower alkyloxy, nitro), substituted or unsubstituted aryl lower alkyl (example of substituent: lower alkyl, halogen, lower alkyloxy, nitro, oxo), substituted or unsubstituted heterocyclyl (example of substituent: lower alkyl, halogen, lower alkyloxy, nitro), substituted or unsubstituted heterocyclyl lower alkyl (example of substituent: lower alkyl, halogen, lower alkyloxy, nitro, oxo), substituted or unsubstituted lower alkylcarbonyl (substituent: lower alkoxy, halogen), cycloalkylcarbonyl, substituted or unsubstituted benzoyl (substituent: lower alkoxy, halogen), substituted sulfonyl (substituent: lower alkyl, aryl, heterocyclyl (preferably 5- to 6-membered aromatic heterocyclyl)).

More preferably, $R^{12a}$ and $R^{12b}$ are hydrogen.

$R^{12a}$ and $R^{12b}$ may be taken together to form oxo or thioxo.

[Chemical Formula 45]

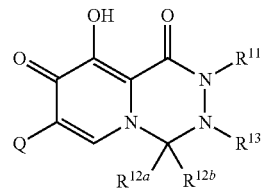

(I-3-4)

$R^{11}$, $R^{12a}$, $R^{12b}$ and $R^{13}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N═ and ═N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido.

$R^{11}$ is preferably, substituted or unsubstituted lower alkyl (e.g., methyl, n-propyl, n-buthyl (proviso ethyl and isopropyl are excluded); example of substituent: hydroxy, amino, lower alkylamino, lower alkoxy, aryloxy, oxo, lower alkoxycarbonyl, substituted or unsubstituted heterocyclylcarbonyl (example of substituent: lower alkyl, lower alkoxy), specifically, lower alkylamino lower alkyl (e.g., 2-dimethylaminoethyl, 2-diethylaminoethyl), lower alkoxylower alkyl (e.g., 1-methoxyethyl, 2-methoxypropyl, 2-methoxyethyl, 3-methoxypropyl, 4-methoxybuthyl, 2-ethoxyethyl, 3-ethoxypropyl, 4-ethoxybuthyl, 2-propoxyethyl, 3-propoxypropyl, 4-propoxybutyl) or aryloxy lower alkyl (e.g., 2-phenoxyethyl, 3-phenoxypropyl); substituted or unsubstituted cycloalkyl (e.g., cyclopropyl); substituted or unsubstituted cycloalkyl lower alkyl (e.g., cyclopropylmethyl, 1-adamantylmethyl, 2-adamantylmethyl, dodecahedranemethyl, cubanemethyl); substituted or unsubstituted aryl (e.g., phenyl; example of substituent: lower alkyl, halogen, lower alkyloxy, nitro; or a substituent part may be lower alkylene that may be intervened by a heteroatom (e.g., O)); substituted or unsubstituted aryl lower alkyl (e.g., benzyl; example of substituent: lower alkyl, halogen, lower alkyloxy, nitro; or a substituent part may be lower alkylene that may be intervened by a heteroatom (e.g., O)); substituted or unsubstituted heterocyclyl (preferably 5- to 6-membered ring) (e.g., picolyl, pyridyl; example of substituent: lower alkyl, halogen, lower alkyloxy, nitro); or an substituted or unsubstituted heterocyclic group (preferably 5- to 6-membered ring) lower alkyl (e.g., piperonylmethyl, 2-morpholinoethyl, thiophenemethyl, furanmethyl, tetrahydrofuranmethyl, dioxanemethyl, tetrahydropyranmethyl, thiazolemethyl, oxazolemethyl, 1,2,4-oxadiazolemethyl, 1,3,4-oxadiazolemethyl; example of substituent: lower alkyl, halogen, lower alkyloxy, nitro; and the heterocycle may be condensed to a benzene ring).

$R^{12a}$ and $R^{12b}$ are preferably, each independently, hydrogen, substituted or unsubstituted lower alkyl (example of substituent: amino, lower alkylamino, lower carbonylamino, lower alkoxy, aryloxy, cyano, halogen, acylamino (e.g., lower carbonylamino), lower alkynyl, hydroxy, lower alkoxycarbonyl, substituted or unsubstituted heterocyclylcarbonyl (example of substituent: lower alkyl, lower alkoxy), lower alkenyl, substituted or unsubstituted carbamoyl (example of substituent: lower alkyl), lower alkylcarbonyloxy, lower alkyloxycarbonyl, lower alkylcarbonylamino, oxo, lower alkynyl), cycloalkyl, cycloalkyl lower alkyl, substituted or unsubstituted aryl (example of substituent: lower alkyl, halogen, lower alkyloxy, nitro), substituted or unsubstituted aryl lower alkyl (example of substituent: lower alkyl, halogen, lower alkyloxy, nitro, oxo), substituted or unsubstituted heterocyclyl (example of substituent: lower alkyl, halogen, lower alkyloxy, nitro), substituted or unsubstituted heterocyclyl lower alkyl (example of substituent: lower alkyl, halogen, lower alkyloxy, nitro, oxo), substituted or unsubstituted lower alkylcarbonyl (substituent: lower alkoxy, halogen), cycloalkylcarbonyl, substituted or unsubstituted benzoyl (substituent: lower alkoxy, halogen), substituted sulfonyl (substituent: lower alkyl, aryl, heterocyclyl (preferably 5- to 6-membered aromatic heterocyclyl)).

More preferably, $R^{12a}$ and $R^{12b}$ are hydrogen.

$R^{12a}$ and $R^{12b}$ may be taken together to form oxo, thioxo or substituted or unsubstituted spiro ring (example of substituent: halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.).

[Formula 46]

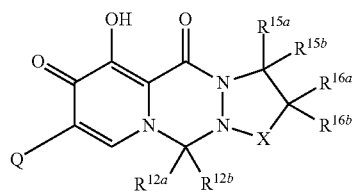

(I-3-5)

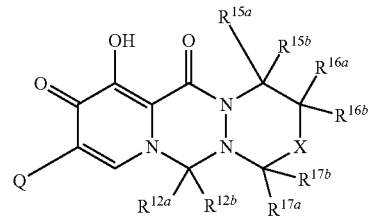

(I-3-6)

X is $CR^{18a}R^{18b}$, $NR^{24}$, O or S, preferably, is $CR^{18a}R^{18b}$ or O.

$R^{15a}$, $R^{15b}$, $R^{16a}$, $R^{16b}$, $R^{17a}$, $R^{17b}$, $R^{18a}$, $R^{18b}$ and $R^{24}$ may be a variety of substituents as far as they do not adversely affect on the pharmacological activity of the present compound. Examples thereof include, for example, each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (A heteroatom group selected from the group consisting of O, S, SO, $SO_2$, $NR^5$ ($R^5$ is selected independently from the same substituents group as $R^4$.), —N= and =N— may intervene in the lower alkyl.), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido or substituted or unsubstituted thioureido.

$R^{15a}$, $R^{15b}$, $R^{16a}$, $R^{16b}$, $R^{17a}$, $R^{17b}$, $R^{18a}$, $R^{18b}$ and $R^{24}$ are preferably, each independently, hydrogen, halogen, hydroxy, substituted or unsubstituted lower alkyl, substituted or unsubstituted cycloalkyl, and the like. Examples of a substituent(s) in the "substituted or unsubstituted" on $R^{15a}$, $R^{15b}$, $R^{16a}$, $R^{16b}$, $R^{17a}$, $R^{17b}$, $R^{18a}$, $R^{18b}$ or $R^{24}$ include halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

$R^{15a}$, $R^{15b}$, $R^{16a}$, $R^{16b}$, $R^{17a}$, $R^{17b}$, $R^{18a}$, $R^{18b}$ and $R^{24}$ are more preferably, each independently, hydrogen, halogen, hydroxy, lower alkyl, lower alkenyl, lower alkoxy, lower alkenyloxy or substituted or unsubstituted amino, further preferably, each independently, hydrogen or lower alkyl (e.g., methyl).

$R^{15a}$ and $R^{15b}$, $R^{16a}$ and $R^{16b}$, $R^{17a}$ and $R^{17b}$, or $R^{18a}$ and $R^{18b}$ may be taken together to form oxo, thioxo or substituted or unsubstituted spiro ring.

$R^{15b}$ and $R^{16b}$, $R^{16b}$ and $R^{18b}$, and/or $R^{17b}$ and $R^{18b}$ may be taken together to form substituted or unsubstituted carbocycle or substituted or unsubstituted heterocycle, or $R^{15b}$ and $R^{17b}$, $R^{15b}$ and $R^{18b}$, or $R^{16b}$ and $R^{17b}$ may be taken together to form substituted or unsubstituted (C2-C4) bridge.

$R^{16b}$ and $R^{24}$, or $R^{17b}$ and $R^{24}$ may be taken together to form substituted or unsubstituted heterocycle, or $R^{15b}$ and $R^{24}$ may be taken together to form substituted or unsubstituted (C2-C4) bridge.

In this case, example of substituent of "substituted or unsubstituted carbocycle", "substituted or unsubstituted heterocycle", "substituted or unsubstituted (C2-C4) bridge" or "substituted or unsubstituted spiro ring" is halogen, hydroxy, amino, lower alkylamino, cyano, carboxy, formyl, oxo, lower alkyl, lower alkoxy, lower alkylthio, carbamoyl, lower alkylcarbamoyl, aryl, heterocyclyl, lower alkylcarbonyl, lower alkylcarbonyloxy, lower alkoxycarbonyl, halogenated lower alkyl, halogenated lower alkoxy, and the like, more preferably, halogen, hydroxy, amino, lower alkylamino, lower alkyl, lower alkoxy, and the like.

Example of formula (I-3), (I-3-1), (I-3-2), (I-3-3), (I-3-4), (I-3-5) and (I-3-6) are specifically exemplified as following formula.

[Chemical Formula 47]

(I-3-7)

(I-3-8)

(I-3-9)

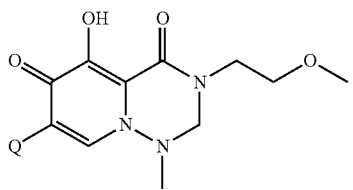
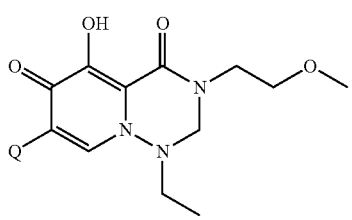
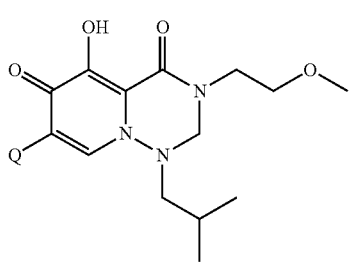

(I-3-10)
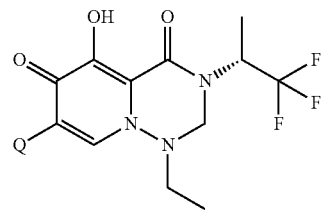

(I-3-11)
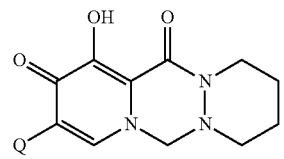

(I-3-12)
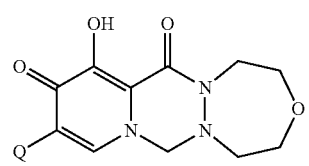

(I-3-13)
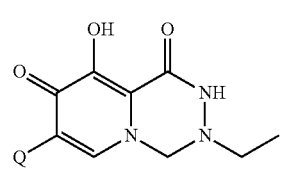

(I-3-14)
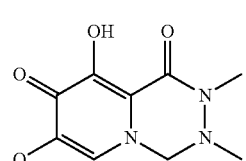

(I-3-15)
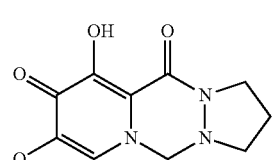

(I-3-16)
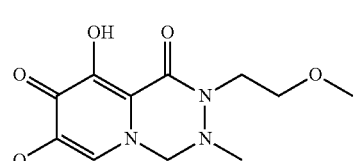

(I-3-17)
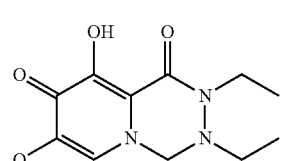

(I-3-18)

-continued (I-3-19)
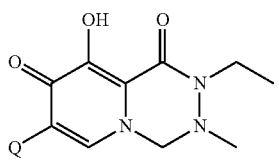

(I-3-20)
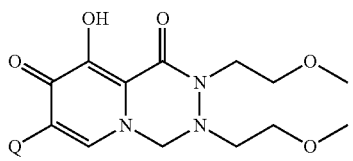

(I-3-21)
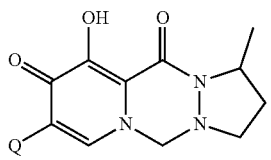

(Embodiment of the Combination Core Structure and Side Chain)

The present compound is including the compound combined any one of the above core structures formula (I-1-2) to (I-1-8), (I-2-2) to (I-2-14), (I-3-7) to (I-3-15) and (I-4-1) to (I-4-4) with any one of the side chains formula (Q1) to (Q30).

[Chemical Formula 48]

(I-4-1)
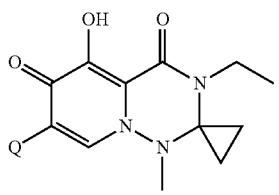

(I-4-2)
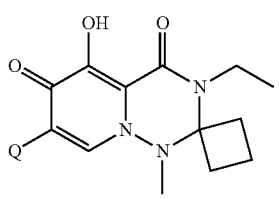

(I-4-3)
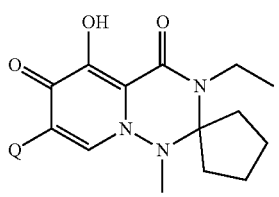

(I-4-4)
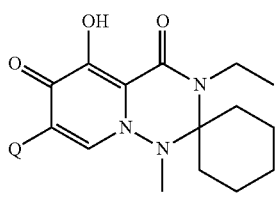

(Prodrug)

The present compound includes prodrug. Specifically, the compound or its pharmaceutically acceptable salt represented by any one of the following formula (I-1'), (I-2') or (I-3'):

[Chemical Formula 49]

(I-1')
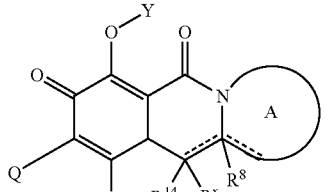

(I-2')
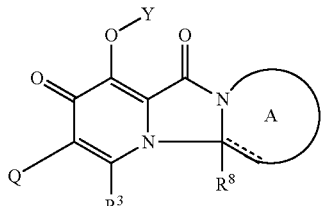

(I-3')
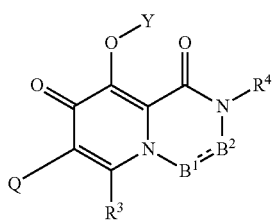

wherein Y is any groups of the following:

[Chemical Formula 50]

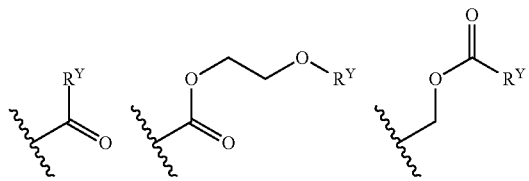

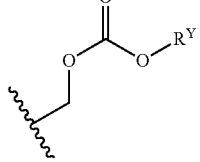

wherein $R^Y$ is substituted or unsubstituted alkyl (example of substituent: halogen, hydroxy, carboxy, cyano, amino, alkyloxy, aromatic carbocyclyl, unsubstituted aromatic carbocyclyl, aromatic heterocyclyl, unsubstituted aromatic heterocyclyl).

The other symbols are defined the same as the above item [1].

$R^Y$ is preferably, methyl, ethyl, n-propyl, isopropyl, n-buthyl, isobuthyl, sec-buthyl, tert-buthyl, or methoxyethyl.

$R^Y$ is further preferably, methyl, tert-buthyl, or methoxyethyl.

The present compound has at least the following characteristics as its chemical structure:
(1) the condensed heterocycle, which is the main backbone, is substituted with oxo (=O), hydroxy (OH), and oxo (=O); and
(2) an adjacent position to oxo on the condensed heterocycle has a cyclic group represented by -Q. Q is preferably an substituted or unsubstituted heterocyclic group.
By possession of such a structure, the present compound exhibits remarkably potent integrase inhibitory activity and/or cell proliferation inhibitory activity against viruses including HIV (preferably HIV-1). Preferably, it is also effective against resistant bacteria. Meanwhile, the structures of other parts ($R^3$, $R^{14}$, $R^x$, A ring, D ring, E ring, F ring, G ring, H ring, $B^1$, $B^2$, etc.) can be relatively freely selected from various structures, may have any kind of substituent, may form a condensed ring, and the condensed ring may be further substituted.

The present compound or its pharmaceutically acceptable salts may form solvates (e.g., hydrates or the like), cocrystal and/or crystal polymorphs. The present invention encompasses those various solvates, cocrystal and crystal polymorphs. "Solvates" may be those wherein any numbers of solvent molecules (e.g., water molecules or the like) are coordinated with the present compound or its pharmaceutically acceptable salts. When the present compound or its pharmaceutically acceptable salts are allowed to stand in the atmosphere, the compounds may absorb water, resulting in attachment of adsorbed water or formation of hydrates. Recrystallization of the present compound or its pharmaceutically acceptable salts may produce crystal polymorphs. The term "cocrystal" means that a present compound or salts and a counter-molecule exist in the same crystal lattice, and it can be formed with any number of counter-molecules. All theoretically possible tautomers, geometrical isomers, stereoisomers, optical isomers, racemates, and the like of the present compound are also within the scope of the invention.

Pharmaceutically acceptable salts of a compound of the present invention include, as basic salts, for example, alkali metal salts such as sodium salts, potassium salts, and the like; alkaline-earth metal salts such as calcium salts, magnesium salts, and the like; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts, ethylenediamine salts, and the like; aralkylamine salts such as N,N-dibenzylethylenediamine salts, benethamine salts, and the like; heterocyclic aromatic amine salts such as pyridine salts, picoline salts, quinoline salts, isoquinoline salts, and the like; quaternary ammonium salts such as tetramethylammonium salts, tetraethylammonium salts, benzyltrimethylammonium salts, benzyltriethylammonium salts, benzyltributylammonium salts, methyltrioctylammonium salts, tetrabutylammonium salts, and the like; basic amino acid salts such as arginine salts, lysine salts, and the like; and the like. Acid salts thereof include, for example, inorganic acid salts such as hydrochlorides, sulfates, nitrates, phosphates, carbonates, hydrogen carbonates, and perchlorates, and the like; organic acid salts such as acetates, propionates, lactates, maleates, fumarates, tartrates, malates, citrates, ascorbates, and the like; sulfonates such as methanesulfonates, isethionates, benzenesulfonates, p-toluenesulfonates, and the like; acidic amino acid salts such as aspartates, glutamates, and the like; and the like.

Solvates of a compound of the present invention include solvates with alcohol, hydrates, and the like.

The compounds of the present invention can be synthesized using commercially available reagents and known compounds as raw materials, preferably by the method described in Patent Document 15 or in accordance with the following method.

(Production Method 1)

[Chemical Formula 51]

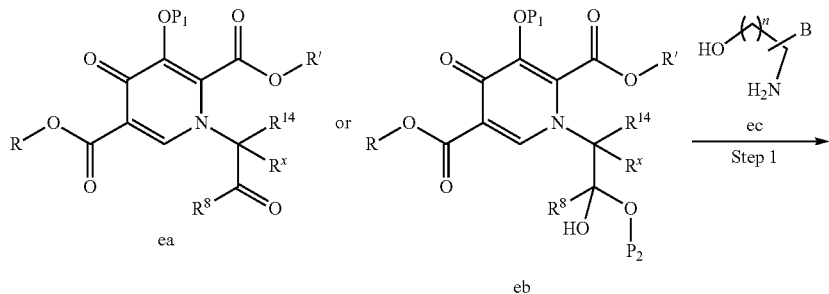

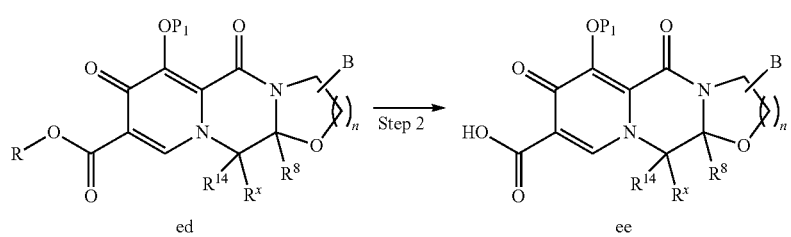

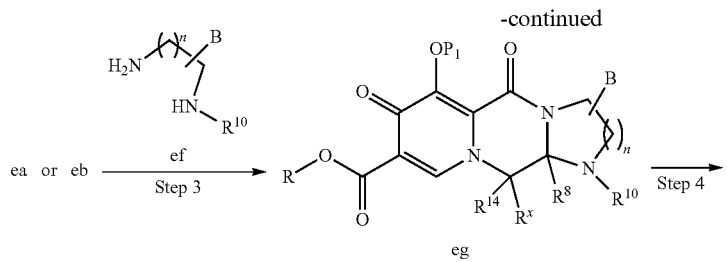

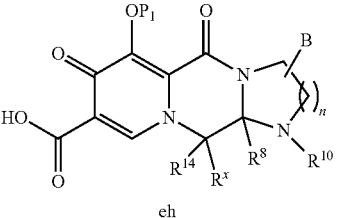

Wherein $P_1$ and $P_2$ are a hydroxy-protecting group; R and R' are a carboxy-protecting group; B is $R^{5a}$, $R^{5b}$, $R^{6a}$, $R^{6b}$, $R^{7a}$ and $R^{7b}$; the other symbols are defined the same as above; $P_1$ and $P_2$ are a group which can be protected and/or deprotected described in Protective Groups in Organic Synthesis, Theodora W Green (John Wiley & Sons) etc., for example, $P_1$ is arylalkyl, and the like; R, R' and $P_2$ are lower alkyl, and the like.

Step 1

Compound ec commercially available or prepared by a known method and acetic acid are added to Compound ea or Compound eb prepared by a known method in the solvent such as chloroform, dichloromethane, THF, and the like. Compound ed can be obtained by reacting at 0° C. to 40° C., preferably 10° C. to 30° C. for 0.5 hours to 24 hours, preferably an hour to 12 hours.

Step 2

Compound cc can be obtained from Compound ed by a known deprotective reaction of a hydroxy-protecting group.

Step 3

Compound ef and acetic acid are added to Compound ea or Compound eb in the solvent such as chloroform, dichloromethane, THF, and the like. Compound eg can be obtained by reacting at 0° C. to 40° C., preferably 10° C. to 30° C. for 0.5 hours to 24 hours, preferably an hour to 12 hours.

Step 4

Compound eh can be obtained from Compound eg by a known deprotective reaction of a hydroxy-protecting group.

[Chemical Formula 52]

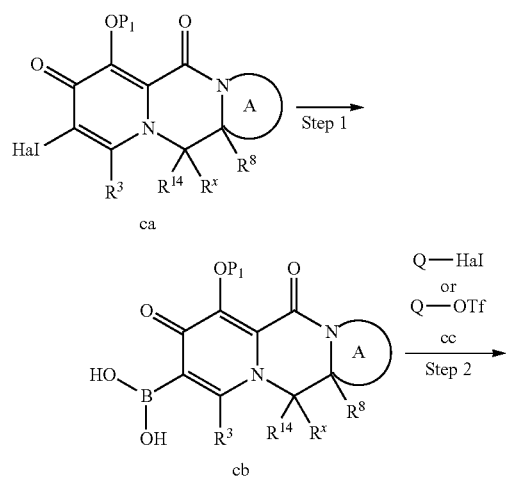

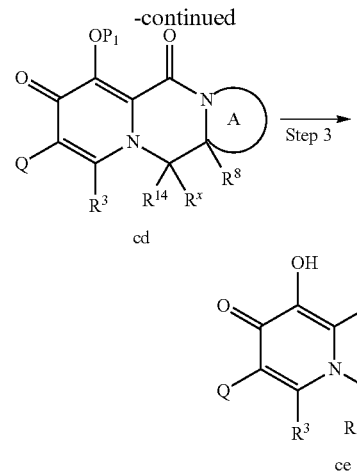

Wherein $P_1$ is a hydroxy-protecting group; Hal is halogen; other symbols are defined the same as above; $P_1$ is a group which can be protected and/or deprotected described in Protective Groups in Organic Synthesis, Theodora W Green (John Wiley & Sons) etc., for example, $P_1$ is arylalkyl, and the like.

Step 1

A palladium catalyst such as $Pd(PPh_3)_4$, $Pd(OAc)_2$, $Pd(PPh_3)_2Cl_2$, $Pd(dppf)_2Cl_2$, $Pd(dtbpf)$, and the like and base such as potassium acetic acid, sodium acetic acid, potassium carbonate, potassium phosphate, and the like and bis(pinacolato)diboron were added to Compound ca prepared by a known method in solvent such as dioxane, DMF, DME, tetrahydrofuran, DMSO, and the like or its solvent mixture. Compound cb can be obtained by reacting at 0° C. to 150° C., preferably 60° C. to 120° C. for 0.5 hours to 24 hours, preferably an hour to 12 hours under the nitrogen atmosphere.

Step 2

A palladium catalyst such as $Pd(PPh_3)_4$, $Pd(OAc)_2$, $Pd(PPh_3)_2Cl_2$, $Pd(dppf)_2Cl_2$, $Pd(dtbpf)$, and the like and base such as potassium carbonate, sodium carbonate, cesium carbonate, potassium phosphate, and the like Compound cc commercially available or prepared by a known method are added to Compound cb in solvent such as dioxane, DMF, DME, tetrahydrofuran, water, and the like or its solvent mixture. Compound cd can be obtained by reacting at 0° C. to 150° C., preferably 60° C. to 120° C. for 0.5 hours to 24 hours, preferably an hour to 12 hours under the nitrogen atmosphere.

Step 3

Compound ce can be obtained from Compound cd by a known deprotective reaction of a hydroxy-protecting group.

(Production Method 2)

[Chemical Formula 53]

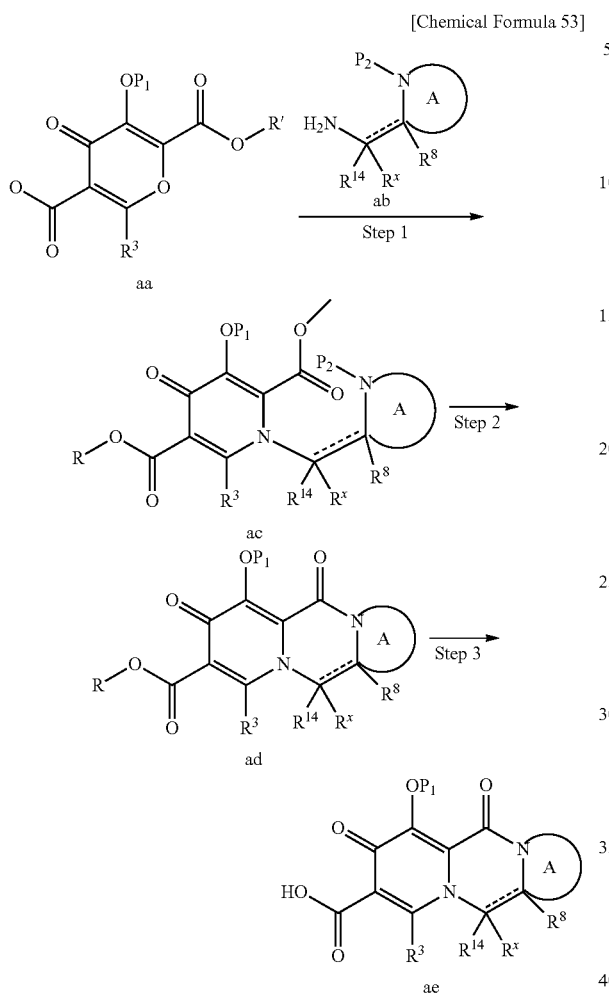

Step 3
Compound ae can be obtained from Compound ad by a known deprotective reaction of a carboxy-protecting group.

[Chemical Formula 54]

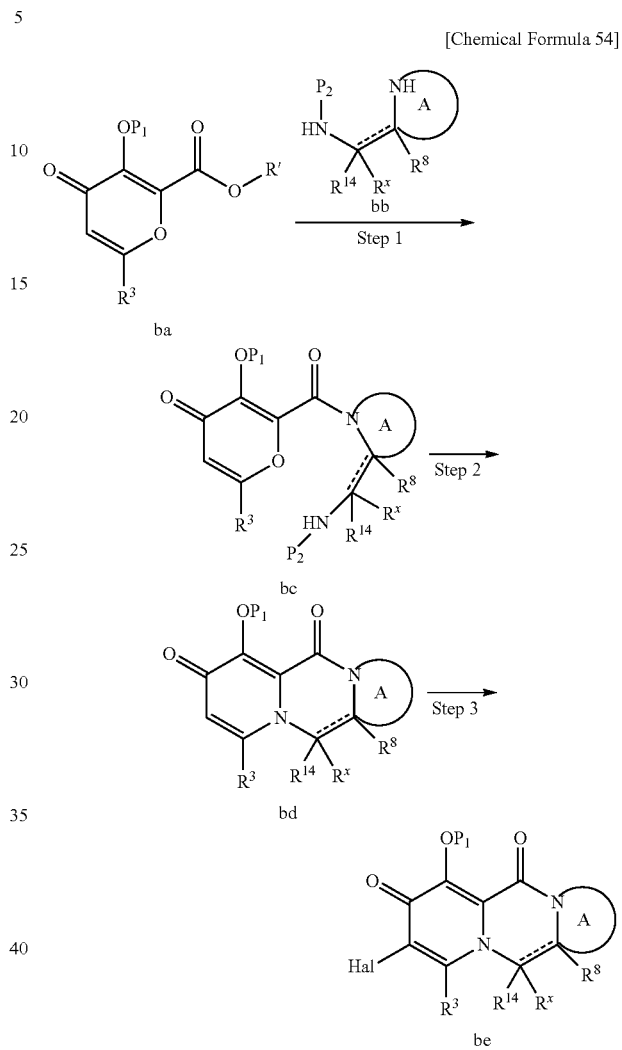

Wherein R and R' are a carboxy-protecting group; $P_1$ is a hydroxy-protecting group; $P_2$ is an amino-protecting group; other symbols are defined the same as above; R, R', $P_1$ and $P_2$ are a group which can be protected and/or deprotected described in Protective Groups in Organic Synthesis, Theodora W Green (John Wiley & Sons) etc., for example, $P_1$ is arylalkyl, and the like; $P_2$ is lower alkyloxycarbonyl, and the like.

Step 1
Compound ab commercially available or prepared by a known method is added to Compound aa commercially available or prepared by a known method in solvent such as toluene, THF, dioxane, acetonitrile, and the like or its solvent mixture. Compound ac can be obtained by reacting at 20° C. to 10° C., preferably 40° C. to under heat reflux for 0.5 hours to 24 hours, preferably an hour to 12 hours.

Step 2
After a known general deprotective reaction of an amino-protecting group to Compound ac, Compound ad can be obtained by reacting at 20° C. to 110° C., preferably 80° C. to 110° C. for 0.1 hours to 10 hours, preferably 0.5 hours to 3 hours with tertiary amine such as triethylamine, diisopropylethylamine, N-methylmorphiline, and the like in solvent such as toluene, THF, dioxane, acetonitrile, and the like.

Wherein R is a carboxy-protecting group; $P_1$ is a hydroxy-protecting group; $P_2$ is an amino-protecting group; Hal is halogen; other symbols are defined the same as above; $P_1$, $P_2$ and R are a group which can be protected and/or deprotected described in Protective Groups in Organic Synthesis, Theodora W Green (John Wiley & Sons) etc., for example, R is lower alkyl, and the like; $P_1$ is arylalkyl, and the like; $P_2$ is lower alkyloxycarbonyl, and the like.

Step 1
Condensing agent such as HATU, WSC.HCl, and the like is added to Compound ba commercially available or prepared by a known method in solvent such as DMF, DMA, NMP, THF, and the like, and Compound bb commercially available or prepared by a known method and tertiary amine such as triethylamine, N-methylmorphiline, pyridine, and the like are added to the mixture. Compound bc can be obtained by reacting at 10° C. to 60° C., preferably 20° C. to 40° C. for 0.1 hours to 24 hours, preferably an hour to 12 hours.

Step 2
Compound bd can be obtained from Compound be by a known deprotective reaction of an amino-protecting group.

Step 3

Halogenated agent such as bromine, NBS, NCS, NIS, and the like is added to the mixture containing Compound bd in solvent such as dichloromethane, dichloroethane, acetonitrile, DMF, and the like. When Hal is bromine, Compound be can be obtained by reacting at −30° C. to 50° C., preferably −10° C. to 20° C. for 0.1 hours to 10 hours, preferably 0.5 hours to 2 hours. When Hal is chlorine or iodine, Compound be can be obtained by reacting at 10° C. to 150° C., preferably 60° C. to 120° C. for 0.5 hours to 24 hours, preferably an hour to 6 hours.

(Production Method 3)

[Chemical Formula 55]

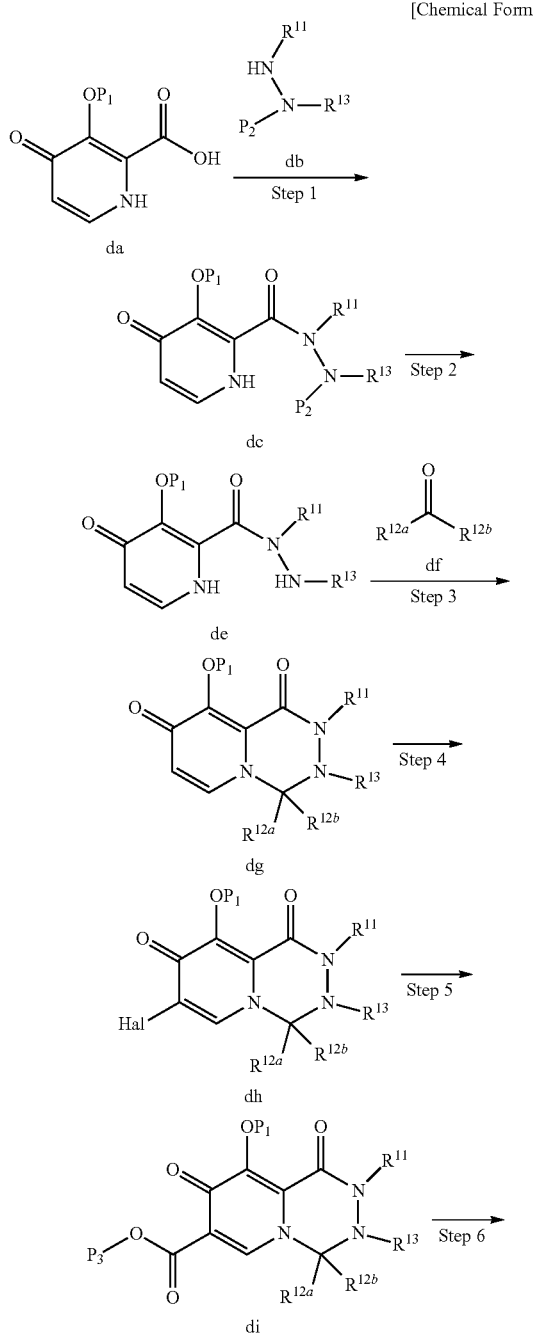

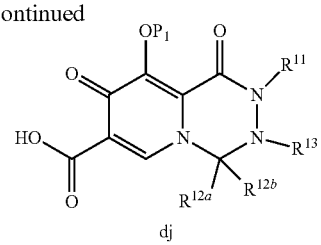

Wherein $P_1$ is a hydroxy-protecting group; $P_2$ is an amino-protecting group; $P_3$ is a carboxy-protecting group; Hal is halogen; other symbols are defined the same as above; $P_1$, $P_2$ and $P_3$ are a group which can be protected and/or deprotected described in Protective Groups in Organic Synthesis, Theodora W Green (John Wiley & Sons) etc., for example, $P_1$ is arylalkyl, and the like; $P_2$ is lower alkyloxycarbonyl, and the like; $P_3$ is lower alkyl, and the like.

Step 1

Condensing agent such as HATU, WSC.HCl, and the like is added to Compound da prepared by a known method in solvent such as DMF, DMA, NMP, THF, and the like, and Compound db commercially available or prepared by a known method and tertiary amine such as triethylamine, N-methylmorphiline, pyridine, and the like are added to the mixture. Compound dc can be obtained by reacting at 10° C. to 60° C., preferably 20° C. to 40° C. for 0.1 hours to 24 hours, preferably an hour to 12 hours.

Step 2

Compound de can be obtained from Compound dc by a known deprotective reaction of an amino-protecting group.

Step 3

Compound df commercially available or prepared by a known method, tertiary amine such as triethylamine, diisopropylethylamine, N-methylmorphiline, and the like and acetic acid are added to Compound de in solvent such as toluene, DMF, DMA, NMP, and the like. Compound dg can be obtained by reacting at 60° C. to 120° C., preferably 80° C. to 100° C. for 0.1 hours to 24 hours, preferably an hour to 12 hours.

Step 4

Halogenated agent such as bromine, NBS, NCS, NIS, and the like is added to Compound dg in solvent such as dichloromethane, dichloroethane, acetonitrile, DMF, and the like. When Hal is bromine, Compound dh can be obtained by reacting at −30° C. to 50° C., preferably −10° C. to 20° C. for 0.1 hours to 10 hours, preferably 0.5 hours to 2 hours. When Hal is chlorine or iodine, Compound dh can be obtained by reacting at 10° C. to 150° C., preferably 60° C. to 120° C. for 0.5 hours to 24 hours, preferably an hour to 6 hours.

Step 5

A palladium catalyst such as $Pd(PPh_3)_4$, $Pd(OAc)_2$, $Pd(PPh_3)_2Cl_2$, $Pd(dppf)_2Cl_2$, $Pd(dtbpf)$, and the like and lower alkylalcohol such as ethanol, propanol, butanol, and the like are added to Compound dh in solvent such as dioxane, DMF, DME, tetrahydrofuran, and the like or its reaction mixture. Compound di can be obtained by reacting at 0° C. to 150° C., preferably 60° C. to 120° C. for 0.5 hours to 24 hours, preferably an hour to 12 hours under the carbon monoxide atmosphere.

Step 6

Compound dj can be obtained from Compound di by a known deprotective reaction of a carboxy-protecting group.

The present compound obtained above may be further chemically modified to synthesize another compound. In addition, in the above reaction, when a reactive functional group (e.g., OH, COOH, NH$_2$) is present on a side chain part, etc., the group may be protected before the reaction and may be deprotected after the reaction if desired.

Examples of protecting groups (such as amino protecting group, hydroxy protecting group, and the like) can include protecting groups, such as ethoxycarbonyl, t-butoxycarbonyl, acetyl, benzyl, and the like, which are described in Protective Groups in Organic Synthesis, written by T. W. Greene, John Wiley & Sons Inc. (1991), or the like. Methods for the introduction and removal of a protecting group are methods commonly used in synthetic organic chemistry (see, for example, methods described in Protective Groups in Organic Synthesis, written by T. W. Greene, John Wiley & Sons Inc., (1991), or the like) or can be obtained in accordance therewith. In addition, a functional group included in each substituent can be converted by a known method (for example, those described in Comprehensive Organic Transformations, written by R. C. Larock (1989), and the like) in addition to the above production methods. Some of the compounds of the present invention can be used as a synthetic intermediate, further leading to a new derivative. Intermediates and target compounds produced in each of the above production methods can be isolated and purified by a purification method commonly used in synthetic organic chemistry, for example, subjecting them to neutralization, filtration, extraction, washing, drying, concentration, recrystallization, any kind of chromatography, or the like. In addition, intermediates can be subjected to a next reaction without further purification.

The present compound is useful, for example, as a medicament such as antiviral agent and the like. The present compound has remarkable inhibitory activity against virus integrase. Therefore, the present compound can be expected to have a preventive or therapeutic effect on various diseases caused by a virus which produces at least integrase and increases at infection in an animal cell; and, for example, it is useful as an integrase inhibiting agent against retroviruses (e.g., HIV-1, HIV-2, HTLV-1, SIV, FIV, etc.); and useful as an anti-HIV agent and the like. A preferred compound also has the following characteristics as pharmacokinetics in the body: the blood concentration is high; the duration of an effect is long; the transitivity to tissue is remarkable; and/or the like. In addition, a preferred compound is safe with regard to a side effect.

In addition, the present compound may be used in a combination therapy in combination with an anti-HIV agent having the different action mechanism such as a reverse transcriptase inhibitor and/or a protease inhibiting agent, etc.

Further, the above use includes not only use as a mixture for anti-HIV, but also use as a concomitant agent for increasing the anti-HIV activity of another anti-HIV agent such as cocktail therapy and the like.

In addition, the present compound can be used to prevent infection with a retrovirus vector from spreading into a tissue other than a target tissue, upon use of a retrovirus vector based on HIV or MLV in the field of gene therapy. Particularly, when a cell or the like is infected with a vector in vitro and then returned into a body, if the present compound is administered in advance, unnecessary infection in the body can be prevented.

The present compound can be administered orally or parenterally. In the case of oral administration, the present compound can be also used as a conventional preparation, for example, as any dosage form of a solid agent such as tablet, powder, granule, capsule, and the like; pharmaceutical solution; oleaginous suspension; liquid such as syrup and elixir; or the like. In the case of parenteral administration, the present compound can be used as an aqueous or oleaginous suspended injection, or a nasal drop. Upon preparation of it, any conventional excipients, binders, lubricants, aqueous solvents, oleaginous solvents, emulsifiers, suspending agents, preservatives, stabilizers and the like may be used. In addition, as an anti-IIIV agent, an oral agent is particularly preferred. A preparation of the present invention is produced by combining (e.g. mixing) a therapeutically effective amount of the present compound with a pharmaceutically acceptable carrier or diluent.

The dose of a compound of the present invention varies depending on an administration method, the age, weight and condition of a patient, and the type of a disease. Usually, in the case of oral administration, about 0.05 mg to 3000 mg, preferably about 0.1 mg to 1000 mg, may be administered per adult daily, if necessary, by dividing the dose. In addition, in the case of parenteral administration, about 0.01 mg to 1000 mg, preferably about 0.05 mg to 500 mg, is administered per adult daily.

EXAMPLES

Hereinafter, Examples are described.

Abbreviation

Bn: Benzyl
DMA: N,N-Dimethylacetamide
DMF: N,N-dimethylformamide
HATU: O-(7-Aza-1H-benzotriazol-1-yl)-N,N,N',N'-tetramethyluronium hexafluorophosphate
NBS: N-Bromosuccinimide
NCS: N-Chlorosuccinimide
NIS: N-Iodosuccinimide
NMP: N-methylpyrrolidone
PdCl$_2$ (dppf): [1,1'-Bis(diphenylphosphino)ferrocene]palladium(II) Dichloride
Pd(PPh$_3$)$_4$: Tetrakis(triphenylphosphine)palladium(0)
TFA: trifluoroacetic acid
THF: tetrahydrofuran
WSC.HCl: 1-(3-Dimethylaminopropyl)-3-ethylcarbodiimide hydrochloride NMR analysis of each example was performed by 300 MHz or 400 MHz using DMSO-d$_6$ or CDCl$_3$.

In the tables "No." means Compound No., "Structure" means chemical structure, "RT (min)" means retention time (min) in LC/MS: liquid column chromatography/mass analysis, "[M+H]+" means molecular weight in LC/MS: liquid column chromatography/mass analysis, and "Method" means the following measuring condition. As for compounds that two type isomers are existed in mobile phase, two peaks may be shown.

(Analytical Method)
(A) Column: ACQUITY UPLC® BEH C18 (1.7 μm i.d. 2.1×50 mm) (Waters)
Flow rate: 0.8 mL/min;
UV detection wavelength: 254 nm;
Mobile phases: [A] aqueous solution containing 0.1% formic acid, [B] acetonitrile containing 0.1% formic acid;
Gradient: linear gradient of 5% to 100% solvent [B] for 3.5 minutes was performed, and 100% solvent [B] was maintained for 0.5 minute.
(B) Column: Shim-pack XR-ODS (2.2 μm, i.d. 50×3.0 mm) (Shimadzu)
Flow rate: 1.6 mL/min;
UV detection wavelength: 254 nm;

Mobile phases: [A] aqueous solution containing 0.1% formic acid, [B] acetonitrile containing 0.1% formic acid;
Gradient: linear gradient of 5% to 100% solvent [B] for 3 minutes was performed, and 100% solvent [B] was maintained for 0.5 minute.

Example 1

The following compound was synthesized by a similar procedure to Example 1 of Patent Document 15 (WO2013/054862).

TABLE 1

| No. | Structure | RT (min) | [M + H]+ | Method |
|---|---|---|---|---|
| A-1 | 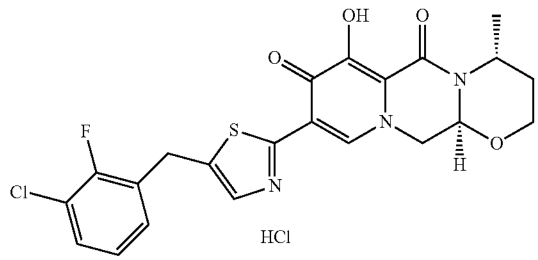 [SMILES: C[C@@H]1CCO[C@H]2Cn3cc(-c4ncc(Cc5cccc(Cl)c5F)s4)c(=O)c(O)c3C(=O)N12 ; Cl] | 1.98 | 476 | A |
| A-2 | 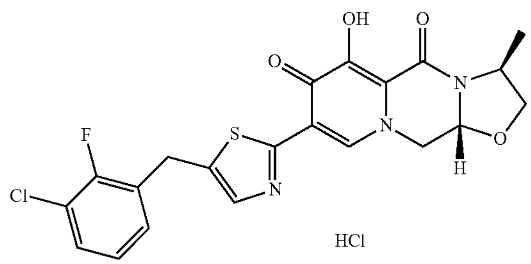 [SMILES: C[C@H]1CO[C@@H]2Cn3cc(-c4ncc(Cc5cccc(Cl)c5F)s4)c(=O)c(O)c3C(=O)N12 ; Cl] | 1.9 | 462 | A |
| A-3 | 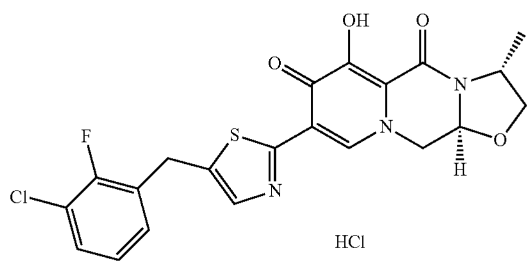 [SMILES: C[C@@H]1CO[C@H]2Cn3cc(-c4ncc(Cc5cccc(Cl)c5F)s4)c(=O)c(O)c3C(=O)N12 ; Cl] | 1.9 | 462 | A |
| A-4 | 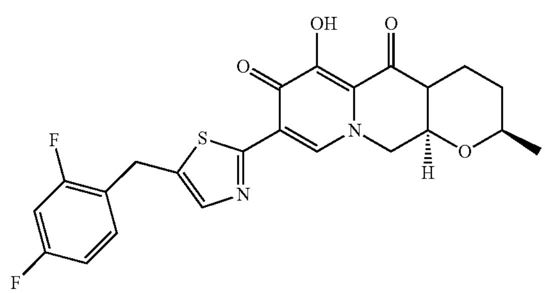 [SMILES: C[C@@H]1CCC2C(=O)c3c(O)c(=O)c(-c4ncc(Cc5ccc(F)cc5F)s4)cn3C[C@@H]2O1] | 1.95 | 460.1 | A |
| A-5 | 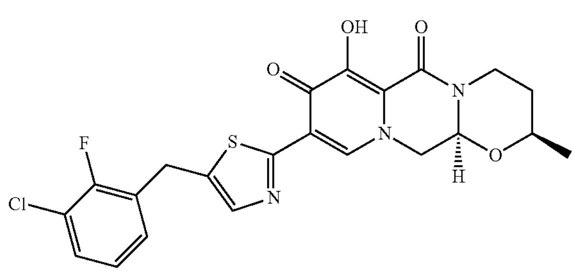 [SMILES: C[C@@H]1CCN2C(=O)c3c(O)c(=O)c(-c4ncc(Cc5cccc(Cl)c5F)s4)cn3C[C@@H]2O1] | 2.08 | 476 | A |

TABLE 1-continued

| No. | Structure | RT (min) | [M + H]+ | Method |
|---|---|---|---|---|
| A-6 | 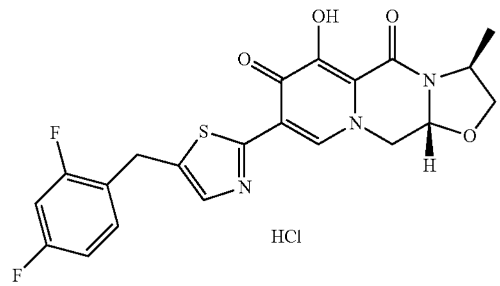 [SMILES: C[C@H]1CO[C@@H]2Cn3cc(-c4ncc(Cc5ccc(F)cc5F)s4)c(=O)c(O)c3C(=O)N12 ; Cl] | 1.77 | 446 | A |

TABLE 2

| No. | Structure | RT (min) | [M + H]+ | Method |
|---|---|---|---|---|
| A-7 | 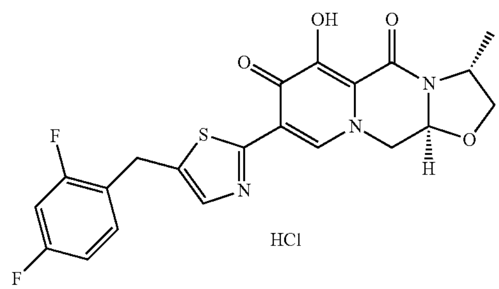 [SMILES: C[C@@H]1CO[C@H]2Cn3cc(-c4ncc(Cc5ccc(F)cc5F)s4)c(=O)c(O)c3C(=O)N12 ; Cl] | 1.77 | 446 | A |
| A-8 | 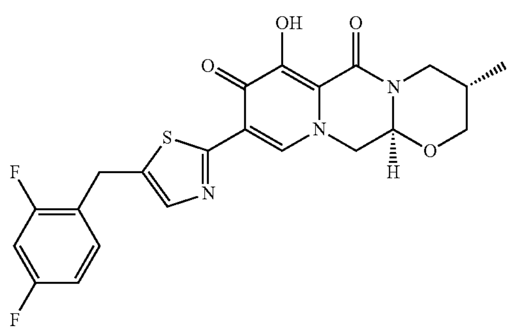 [SMILES: C[C@@H]1CO[C@H]2Cn3cc(-c4ncc(Cc5ccc(F)cc5F)s4)c(=O)c(O)c3C(=O)N2C1] | 1.88 | 460 | A |
| A-9 | 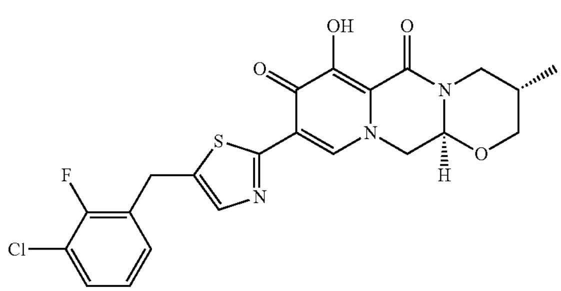 [SMILES: C[C@@H]1CO[C@H]2Cn3cc(-c4ncc(Cc5cccc(Cl)c5F)s4)c(=O)c(O)c3C(=O)N2C1] | 2.0 | 476 | A |

TABLE 2-continued

| No. | Structure | RT (min) | [M + H]+ | Method |
|---|---|---|---|---|
| A-10 | (structure, HCl) | 1.93 | 460 | A |
| A-11 | (structure, HCl) | 2.06 | 476 | A |
| A-12 | (structure) | 1.94 | 478.1 | A |

TABLE 3

| No. | Structure | RT (min) | [M + H]+ | Method |
|---|---|---|---|---|
| A-13 | (structure) | 1.87 | 460 | B |
| A-14 | (structure) | 1.80 | 464 | A |

The following compound was synthesized by a similar procedure to Example 3 of Patent Document 15 (WO2013/054862).

TABLE 4

| No. | Structure | RT (min) | [M + H]+ | Method |
|---|---|---|---|---|
| A-15 | 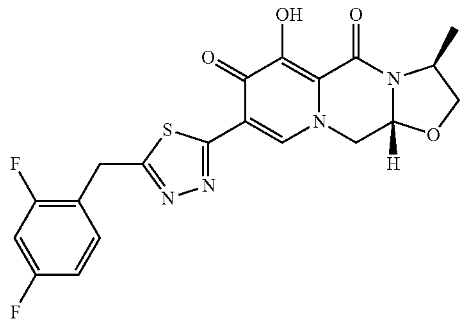 [SMILES: C[C@H]1CO[C@@H]2Cn3cc(-c4nnc(Cc5ccc(F)cc5F)s4)c(=O)c(O)c3C(=O)N12] | 1.55 | 447 | A |
| A-16 | 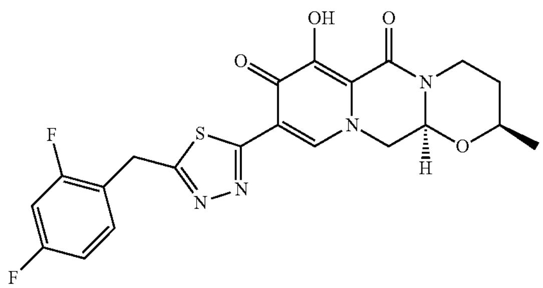 [SMILES: C[C@@H]1CCN2C(=O)c3c(O)c(=O)c(-c4nnc(Cc5ccc(F)cc5F)s4)cn3C[C@@H]2O1] | 1.66 | 461.2 | A |
| A-17 | 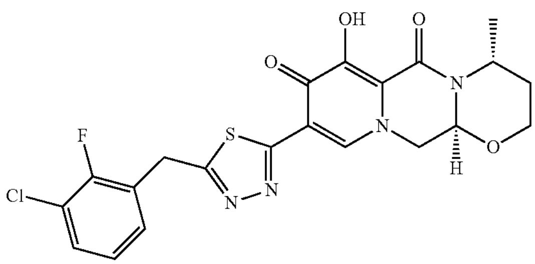 [SMILES: C[C@@H]1CCO[C@H]2Cn3cc(-c4nnc(Cc5cccc(Cl)c5F)s4)c(=O)c(O)c3C(=O)N12] | 1.77 | 477.2 | A |
| A-18 | 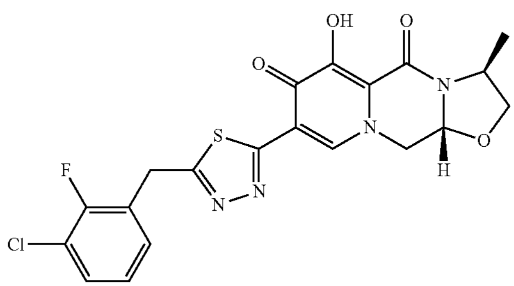 [SMILES: C[C@H]1CO[C@@H]2Cn3cc(-c4nnc(Cc5cccc(Cl)c5F)s4)c(=O)c(O)c3C(=O)N12] | 1.69 | 463 | A |
| A-19 | 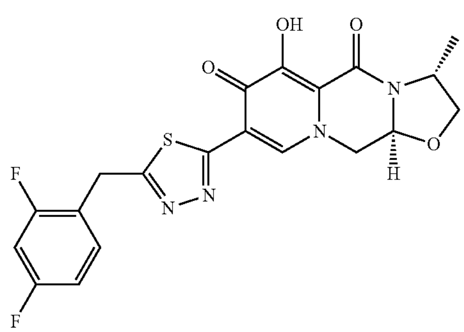 [SMILES: C[C@@H]1CO[C@H]2Cn3cc(-c4nnc(Cc5ccc(F)cc5F)s4)c(=O)c(O)c3C(=O)N12] | 1.55 | 447 | A |

TABLE 4-continued

| No. | Structure | RT (min) | [M + H]+ | Method |
|---|---|---|---|---|
| A-20 | 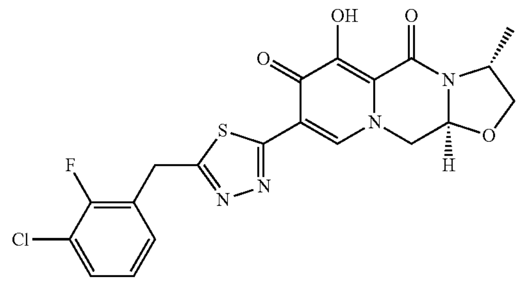 [SMILES: C[C@@H]1CO[C@H]2Cn3cc(-c4nnc(Cc5cccc(Cl)c5F)s4)c(=O)c(O)c3C(=O)N12] | 1.69 | 463 | A |

TABLE 5

| No. | Structure | RT (min) | [M + H]+ | Method |
|---|---|---|---|---|
| A-21 | 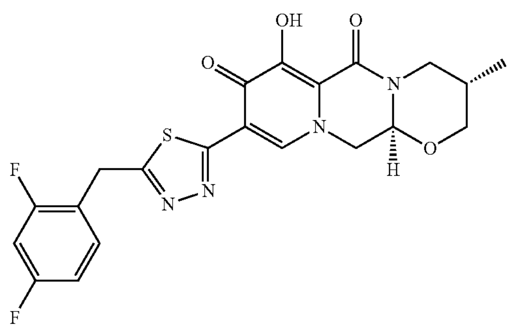 | 1.68 | 461 | A |
| A-22 | 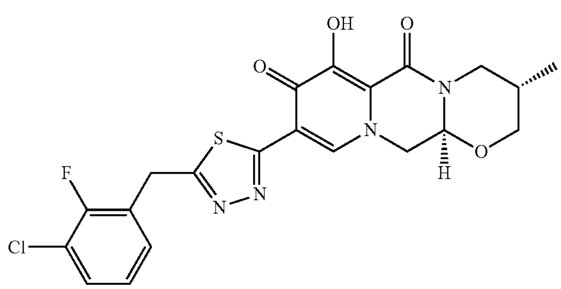 [SMILES: C[C@@H]1CO[C@H]2Cn3cc(-c4nnc(Cc5cccc(Cl)c5F)s4)c(=O)c(O)c3C(=O)N2C1] | 1.81 | 477 | A |
| A-23 | 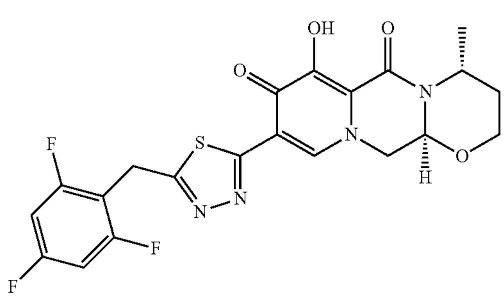 [SMILES: C[C@@H]1CCO[C@H]2Cn3cc(-c4nnc(Cc5c(F)cc(F)cc5F)s4)c(=O)c(O)c3C(=O)N12] | 1.73 | 479.1 | A |

TABLE 5-continued

| No. | Structure | RT (min) | [M + H]+ | Method |
|-----|-----------|----------|----------|--------|
| A-24 | 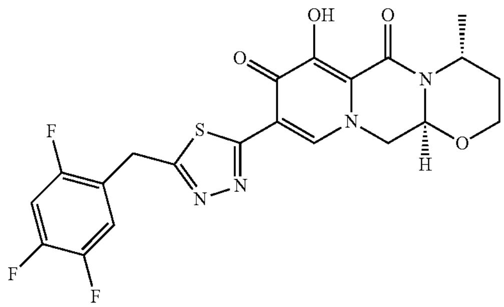 [SMILES: C[C@@H]1CCO[C@H]2Cn3cc(-c4nnc(Cc5cc(F)c(F)cc5F)s4)c(=O)c(O)c3C(=O)N12] | 1.76 | 479.1 | A |
| A-25 | 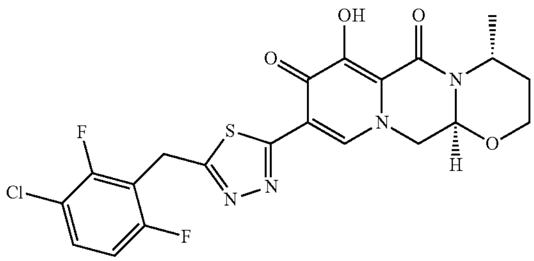 [SMILES: C[C@@H]1CCO[C@H]2Cn3cc(-c4nnc(Cc5c(F)ccc(Cl)c5F)s4)c(=O)c(O)c3C(=O)N12] | 1.84 | 495 | A |
| A-26 | 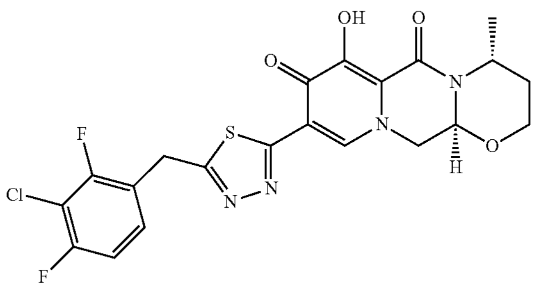 [SMILES: C[C@@H]1CCO[C@H]2Cn3cc(-c4nnc(Cc5ccc(F)c(Cl)c5F)s4)c(=O)c(O)c3C(=O)N12] | 1.89 | 495 | A |

TABLE 6

| No. | Structure | RT (min) | [M + H]+ | Method |
|-----|-----------|----------|----------|--------|
| A-27 | 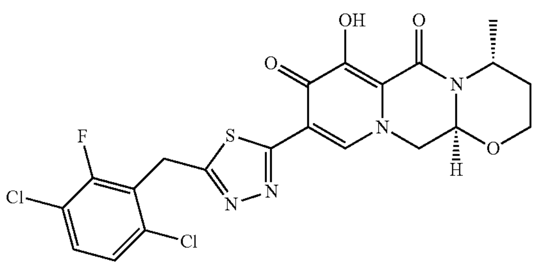 [SMILES: C[C@@H]1CCO[C@H]2Cn3cc(-c4nnc(Cc5c(Cl)ccc(Cl)c5F)s4)c(=O)c(O)c3C(=O)N12] | 1.89 | 511.2 | A |
| A-28 | 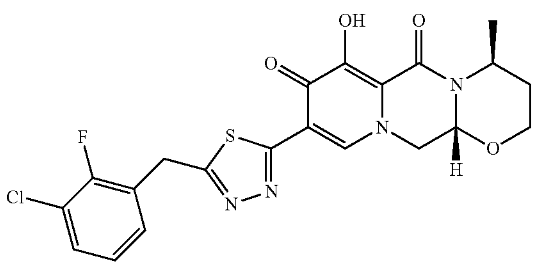 [SMILES: C[C@H]1CCO[C@@H]2Cn3cc(-c4nnc(Cc5cccc(Cl)c5F)s4)c(=O)c(O)c3C(=O)N12] | 1.77 | 477.2 | A |

TABLE 6-continued

| No. | Structure | RT (min) | [M + H]+ | Method |
|---|---|---|---|---|
| A-29 | 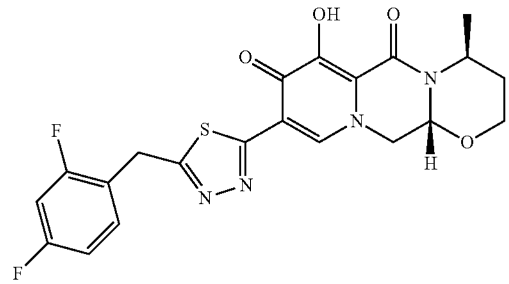 [SMILES: C[C@H]1CCO[C@@H]2Cn3cc(-c4nnc(Cc5ccc(F)cc5F)s4)c(=O)c(O)c3C(=O)N12] | 1.7 | 481.1 | A |
| A-31 | 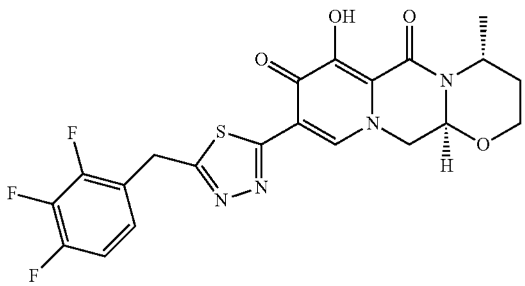 [SMILES: C[C@@H]1CCO[C@H]2Cn3cc(-c4nnc(Cc5ccc(F)c(F)c5F)s4)c(=O)c(O)c3C(=O)N12] | 1.73 | 479.2 | A |
| A-32 | 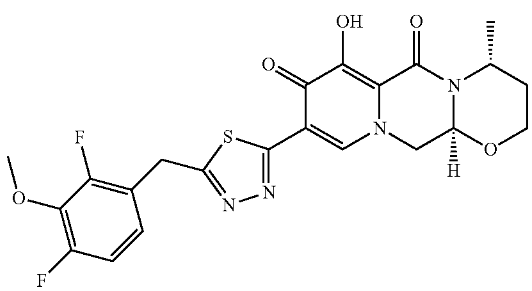 [SMILES: COc1c(F)ccc(Cc2nnc(-c3cn4c(c(O)c3=O)C(=O)N3[C@H](C)CCO[C@H]3C4)s2)c1F] | 1.67 | 491.2 | A |
| A-33 | 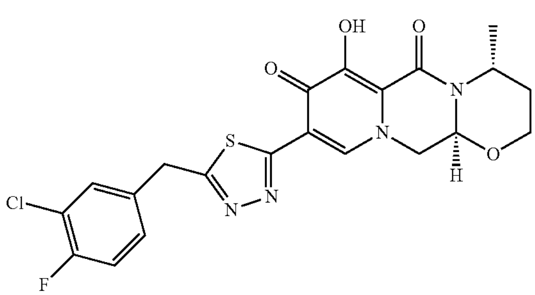 [SMILES: C[C@@H]1CCO[C@H]2Cn3cc(-c4nnc(Cc5ccc(F)c(Cl)c5)s4)c(=O)c(O)c3C(=O)N12] | 1.8 | 477 | A |

TABLE 7

| No. | Structure | RT (min) | [M + H]+ | Method |
|---|---|---|---|---|
| A-34 | 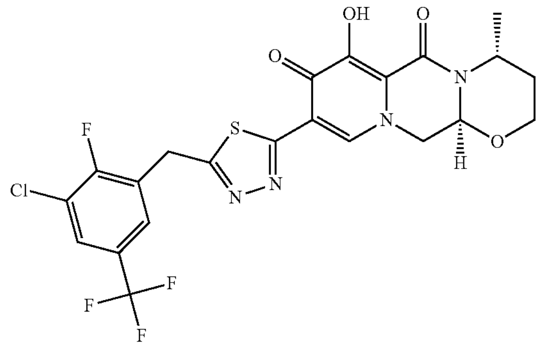 [SMILES: C[C@@H]1CCO[C@H]2Cn3cc(-c4nnc(Cc5cc(C(F)(F)F)cc(Cl)c5F)s4)c(=O)c(O)c3C(=O)N12] | 2.07 | 545 | A |
| A-35 | HCl | 1.44 | 472.1 | A |
| A-36 | 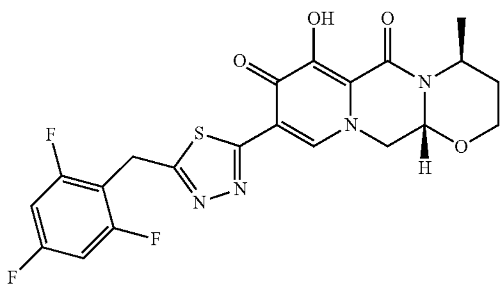 [SMILES: C[C@H]1CCO[C@@H]2Cn3cc(-c4nnc(Cc5c(F)cc(F)cc5F)s4)c(=O)c(O)c3C(=O)N12] | 1.77 | 500 | A |
| A-37 | 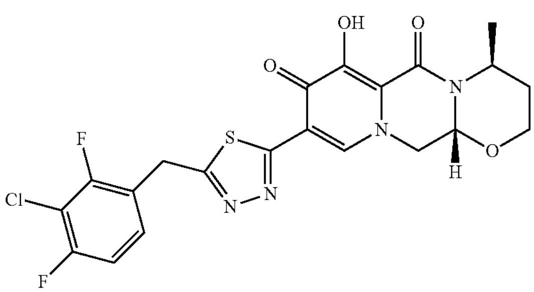 [SMILES: C[C@H]1CCO[C@@H]2Cn3cc(-c4nnc(Cc5ccc(F)c(Cl)c5F)s4)c(=O)c(O)c3C(=O)N12] | 1.91 | 516 | A |
| A-38 | HCl | 1.92 | 491 | A |

TABLE 7-continued

| No. | Structure | RT (min) | [M + H]+ | Method |
|---|---|---|---|---|
| A-39 | 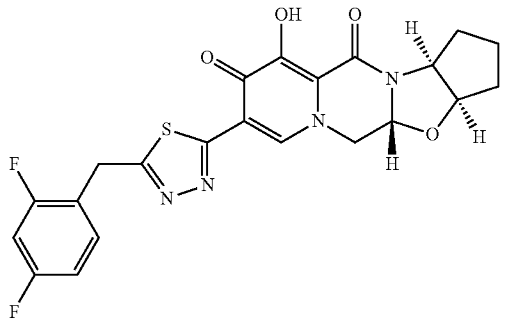 [SMILES: O=C1c2c(O)c(=O)c(-c3nnc(Cc4ccc(F)cc4F)s3)cn2C[C@H]2O[C@@H]3CCC[C@@H]3N12] | 1.73 | 479 | A |

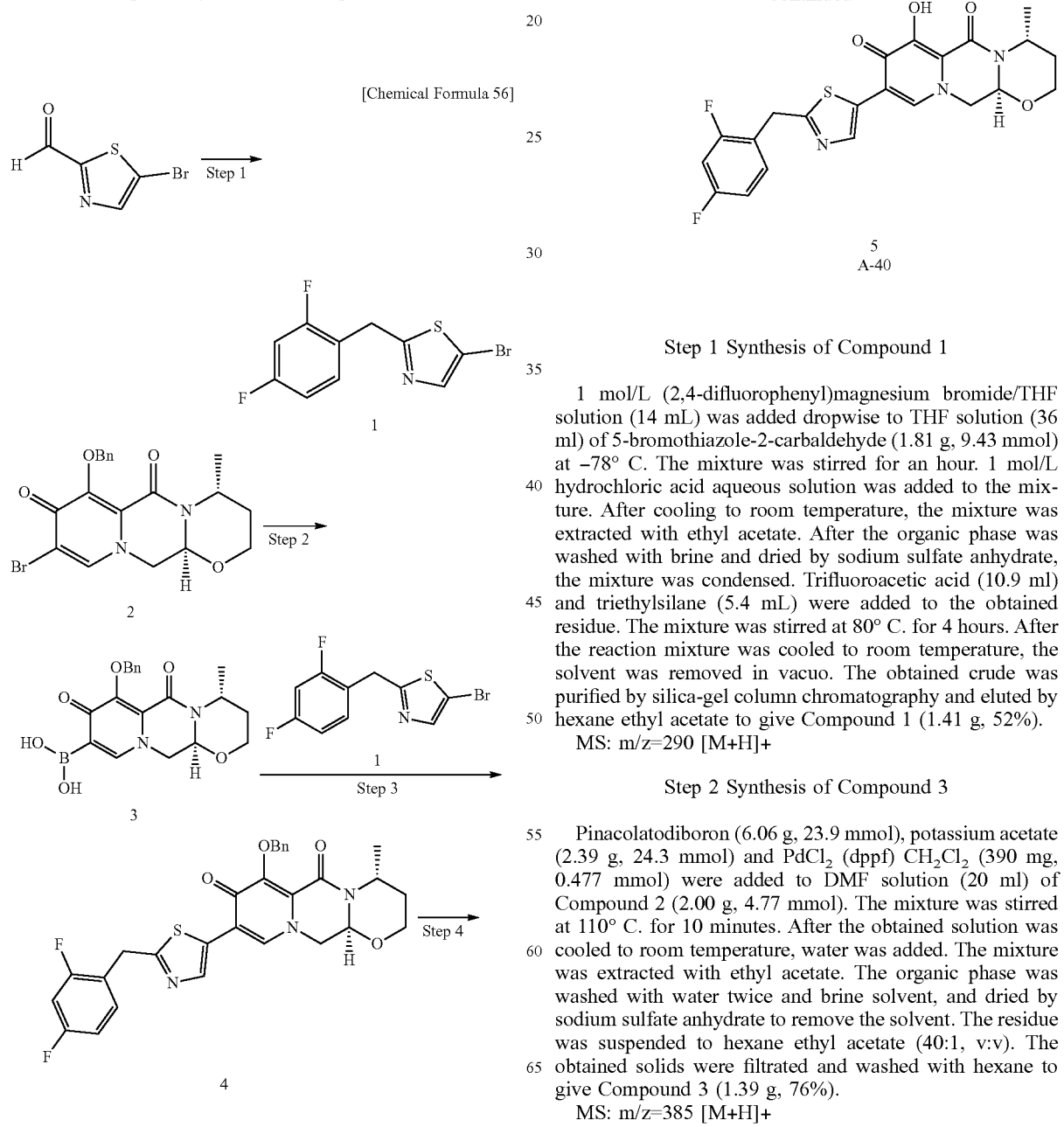

Example 2: Synthesis of Compound A-40

[Chemical Formula 56]

Step 1 Synthesis of Compound 1

1 mol/L (2,4-difluorophenyl)magnesium bromide/THF solution (14 mL) was added dropwise to THF solution (36 ml) of 5-bromothiazole-2-carbaldehyde (1.81 g, 9.43 mmol) at −78° C. The mixture was stirred for an hour. 1 mol/L hydrochloric acid aqueous solution was added to the mixture. After cooling to room temperature, the mixture was extracted with ethyl acetate. After the organic phase was washed with brine and dried by sodium sulfate anhydrate, the mixture was condensed. Trifluoroacetic acid (10.9 ml) and triethylsilane (5.4 mL) were added to the obtained residue. The mixture was stirred at 80° C. for 4 hours. After the reaction mixture was cooled to room temperature, the solvent was removed in vacuo. The obtained crude was purified by silica-gel column chromatography and eluted by hexane ethyl acetate to give Compound 1 (1.41 g, 52%).

MS: m/z=290 [M+H]+

Step 2 Synthesis of Compound 3

Pinacolatodiboron (6.06 g, 23.9 mmol), potassium acetate (2.39 g, 24.3 mmol) and PdCl$_2$ (dppf) CH$_2$Cl$_2$ (390 mg, 0.477 mmol) were added to DMF solution (20 ml) of Compound 2 (2.00 g, 4.77 mmol). The mixture was stirred at 110° C. for 10 minutes. After the obtained solution was cooled to room temperature, water was added. The mixture was extracted with ethyl acetate. The organic phase was washed with water twice and brine solvent, and dried by sodium sulfate anhydrate to remove the solvent. The residue was suspended to hexane ethyl acetate (40:1, v:v). The obtained solids were filtrated and washed with hexane to give Compound 3 (1.39 g, 76%).

MS: m/z=385 [M+H]+

Step 3 Synthesis of Compound 4

Compound 1 obtained by Step 1, 2 mol/L sodium carbonate aqueous solution (521 μl) and PdCl$_2$ (dppf) CH$_2$Cl$_2$ (43 mg, 0.052 mmol) were added to DMF solution (2 ml) of Compound 3 (200 mg, 0.521 mmol) obtained by Step 2. The mixture was stirred at 110° C. for 90 minutes. After the obtained solution was cooled to room temperature, water was added, and the mixture was extracted with ethyl acetate. The organic phase was washed with water twice and dried with sodium sulfate anhydrate to remove the solvent. The obtained crude was purified by silica-gel column chromatography and eluted by chloroform methanol to give Compound 4 (142 mg, 50%).

MS: m/z=369 [M+H]+

Step 4 Synthesis of Compound A-40

Compound 4 (142 mg, 0.258 mmol) was dissolved to TFA (2 ml). The mixture was stirred at room temperature for an hour. The obtained reaction solution was condensed in vacuo. The mixture was diluted with chloroform and washed with sodium hydrogen carbonate aqueous solution and 5% citric acid aqueous solution. The organic phase was dried with sodium sulfate anhydrate. The solvent was removed in vacuo. Ethyl acetate diisopropyl ether was added to the obtained residue to solidify. The solids were filtrated to give Compound A-40 (100 mg, 85%).

LC/MS (ESI): 1.78 min, found 460 (M+1)

$^1$H-NMR (DMSO-D$_6$) δ: 12.29 (1H, s), 8.53 (1H, s), 8.16 (1H, s), 7.57-7.46 (1H, m), 7.31-7.22 (1H, m), 7.15-7.04 (1H, m), 5.53-5.43 (1H, m), 4.88-4.76 (1H, m), 4.52-4.40 (1H, m), 4.33 (2H, s), 4.30-4.21 (1H, m), 4.10-4.01 (1H, m), 3.95-3.86 (1H, m), 2.05-1.98 (1H, m), 1.59-1.50 (1H, m), 1.35 (3H, d, J=7.0 Hz).

The following compound was synthesized by a similar procedure to Example 2.

TABLE 8

| No. | Structure | RT (min) | [M + H]+ | Method |
|---|---|---|---|---|
| A-41 | 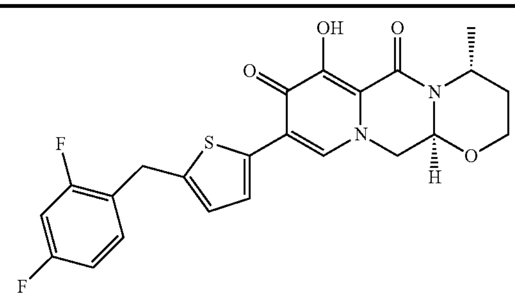 | 1.95 | 459 | B |
| A-42 | 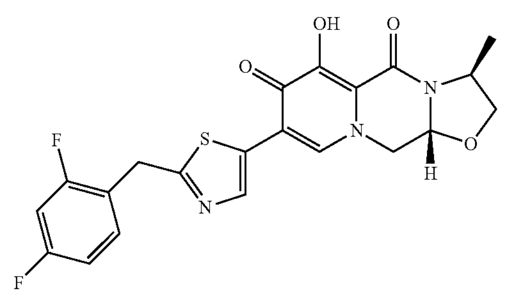 [SMILES: C[C@H]1CO[C@@H]2Cn3cc(-c4cnc(Cc5ccc(F)cc5F)s4)c(=O)c(O)c3C(=O)N12] | 1.69 | 446.2 | A |
| A-43 | 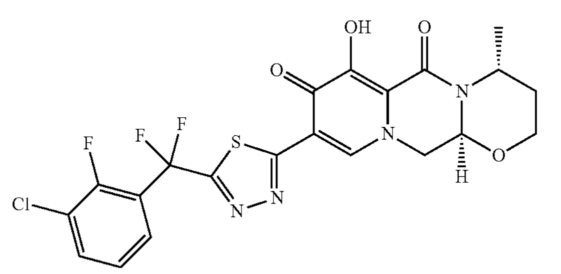 [SMILES: C[C@@H]1CCO[C@H]2Cn3cc(-c4nnc(C(F)(F)c5cccc(Cl)c5F)s4)c(=O)c(O)c3C(=O)N12] | 2.07 | 513.1 | B |

TABLE 8-continued

| No. | Structure | RT (min) | [M + H]+ | Method |
|---|---|---|---|---|
| A-44 | 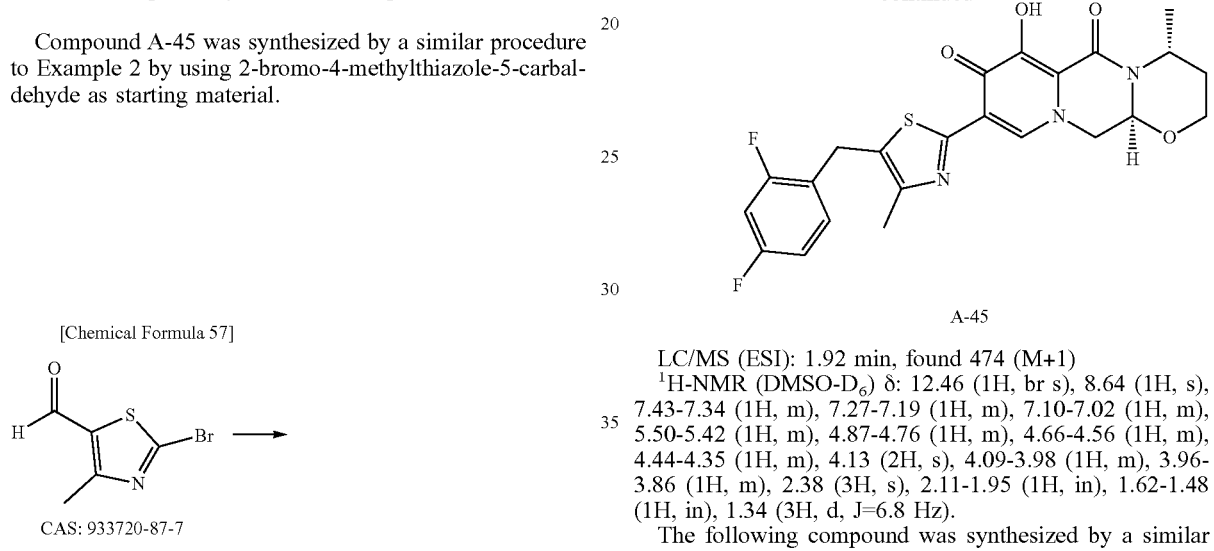 | 1.05 | 429 | A |

Example 3: Synthesis of Compound A-45

Compound A-45 was synthesized by a similar procedure to Example 2 by using 2-bromo-4-methylthiazole-5-carbaldehyde as starting material.

[Chemical Formula 57]

CAS: 933720-87-7

-continued

A-45

LC/MS (ESI): 1.92 min, found 474 (M+1)
$^1$H-NMR (DMSO-$D_6$) δ: 12.46 (1H, br s), 8.64 (1H, s), 7.43-7.34 (1H, m), 7.27-7.19 (1H, m), 7.10-7.02 (1H, m), 5.50-5.42 (1H, m), 4.87-4.76 (1H, m), 4.66-4.56 (1H, m), 4.44-4.35 (1H, m), 4.13 (2H, s), 4.09-3.98 (1H, m), 3.96-3.86 (1H, m), 2.38 (3H, s), 2.11-1.95 (1H, in), 1.62-1.48 (1H, in), 1.34 (3H, d, J=6.8 Hz).

The following compound was synthesized by a similar procedure to Example 3.

TABLE 9

| No. | Structure | RT (min) | [M + H]+ | Method |
|---|---|---|---|---|
| A-46 | 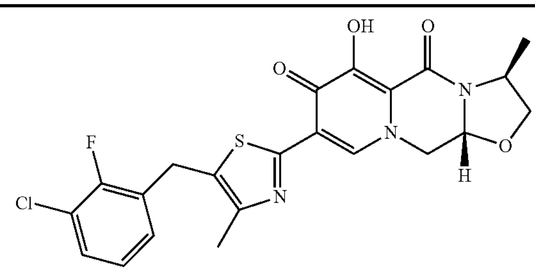 | 1.99 | 476 | A |
| A-47 | 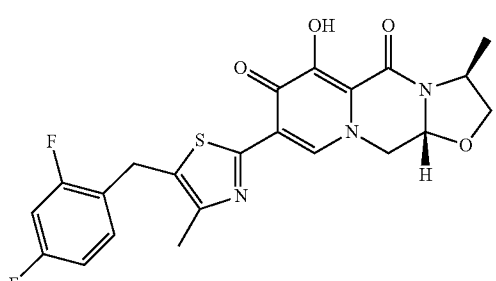 | 1.88 | 460.2 | A |

TABLE 9-continued

| No. | Structure | RT (min) | [M + H]+ | Method |
|---|---|---|---|---|
| A-48 | 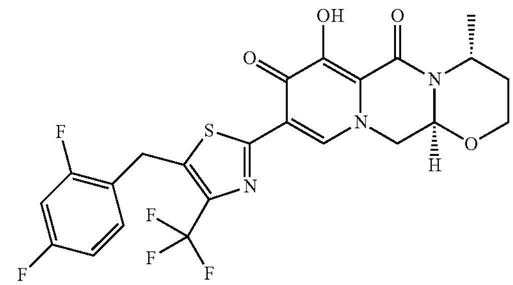 [SMILES: C[C@@H]1CCO[C@H]2Cn3cc(-c4nc(C(F)(F)F)c(Cc5ccc(F)cc5F)s4)c(=O)c(O)c3C(=O)N12] | 2.31 | 528.2 | A |

Example 4: Synthesis of Compound A-49

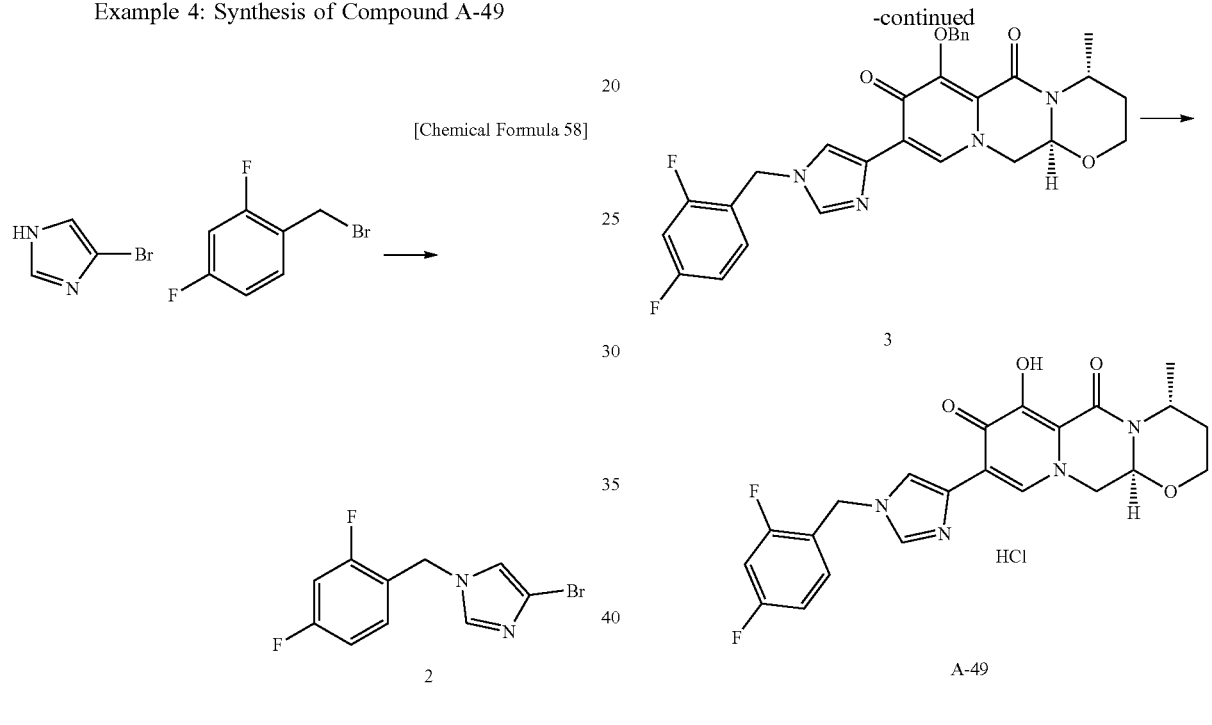

Synthesis of Compound 2

Potassium carbonate (244 mg, 1.77 mmol) and 2,4-difluorobenzyl bromide (0.175 ml, 1.361 mmol) were added to acetone (3 ml) solution of 4-bromo-1H-imidazole (200 mg, 1.36 mmol) under nitrogen atmosphere. The mixture was stirred at room temperature for 2 hours. The obtained reaction solution was filtrated. The filtrate was condensed in vacuo. The obtained crude was purified by silica-gel column chromatography and eluted by hexaneethyl acetate (9:1, v/v) first, and hexaneethyl acetate (1:1, v/v) second. The obtained fractions were condensed to give Compound 2 (256 mg, 69%).

$^1$H-NMR (DMSO-d6) δ: 5.25 (s, 2H), 7.13 (m, 1H), 7.29-7.35 (m, 2H), 7.40 (m, 1H), 7.74 (s, 1H).

Compound A-49 was synthesized by a similar procedure to Example 2 by using Compound 2 from Compound 1.

LC/MS (ESI): 1.14 min, found 443 (M+1)

The following compound was synthesized by a similar procedure to Example 4.

TABLE 10
| No. | Structure | RT (min) | [M + H]+ | Method |
|---|---|---|---|---|
| A-50 | 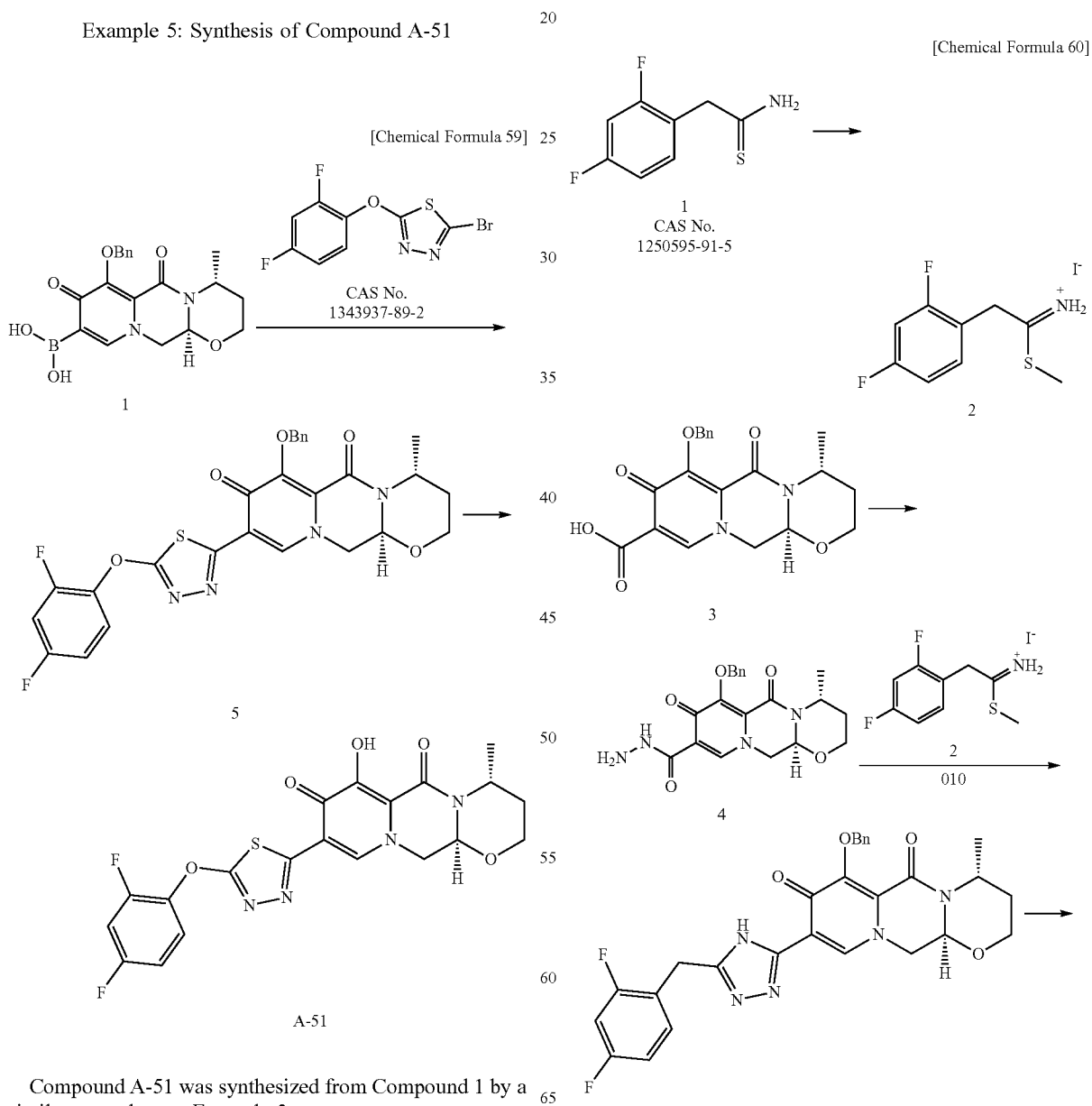 | 1.28 | 459 | A |
Example 5: Synthesis of Compound A-51
[Chemical Formula 59]
A-51
Compound A-51 was synthesized from Compound 1 by a similar procedure to Example 2.
LC/MS (ESI): 1.72 min, found 463 (M+1)
Example 6: Synthesis of Compound A-52
[Chemical Formula 60]
1
CAS No. 1250595-91-5

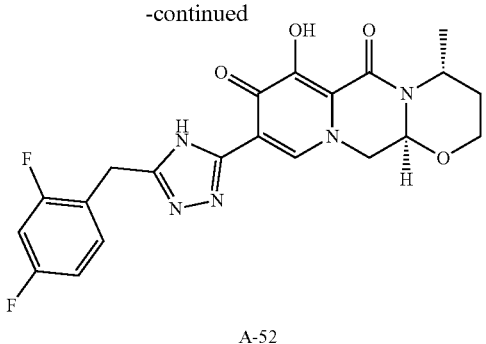

A-52

Synthesis of Compound 2

Compound 1 (200 mg, 1.07 mmol) was dissolved to acetonitrile (2 ml) in an ice-water bath. Methyl iodide (0.334 ml, 5.34 mmol) was added to the mixture. The mixture was stirred at 80° C. for 2 hours. After cooled to room temperature, the half quantity of the solvent was removed in vacuo to give Compound 2 (328 mg, 93%) by filtration.

$^1$H-NMR (DMSO-d6) δ: 2.63 (s, 1H), 4.23 (s, 1H), 7.19 (m, 1H), 7.36 (m, 1H), 7.55 (m, 1H), 11.70 (brs, 1H).

Step 1 Synthesis of Compound 4

Compound 3 (500 mg, 1.30 mmol) was suspended to THF (5 ml) in an ice-water bath. Triethylamine (0.19 ml, 1.43 mmol) and isobutyl chloroformate (0.36 ml, 2.60 mmol) were added. After the mixture was stirred at room temperature for an hour, the suspension solution was added to THF (3 ml) solution of hydrazine monohydrate (0.64 ml, 13.0 mmol) in an ice-water bath. After heated to room temperature, the mixture was stirred for 2 hours. After sodium bicarbonate aqueous solution was added, the mixture was extracted by chloroform twice. After the mixture of extracted solution was dried with sodium sulfate anhydrate, the solvent was removed. The obtained crude was purified by silica-gel column chromatography (chloroform methanol). The objective fractions were condensed to give Compound 4 (430.5 mg, 830%).

$^1$H-NMR (DMSO-d6) δ: 1.27 (d, J=6.8 Hz, 3H), 1.50 (dd, J=1.2 Hz, 13.6 Hz, 1H), 1.94 (m, 1H), 3.85 (m, 1H), 3.96 (m, 1H), 4.37 (dd, J=6.0 Hz, 14.0 Hz, 1H), 4.56 (dd, J=4.5 Hz, 14.0 Hz, 1H), 4.66 (d, J=4.8 Hz, 2H), 4.78 (m, 1H), 5.07 (s, 1H), 5.34 (m, 1H), 7.28-7.40 (m, 3H), 7.54-7.60 (m, 2H), 8.31 (s, 1H), 8.57 (s, 1H), 10.80 (s, 1H).

Step 2 Synthesis of Compound 5

Compound 2 (282 mg, 0.86 mmol) and triethylamine (0.14 ml, 0.97 mmol) were added to Ethanol (3 ml) solution of Compound 4 (155 mg, 0.39 mmol). The mixture was stirred at 90° C. for 3 hours under heat reflux in an oil bath. Further more, the mixture was irradiated with microwave. The mixture was stirred at 140° C. for 8 minutes. After the obtained reaction solution was filtrated, the filtrate was condensed in vacuo. The obtained residue was purified by silica-gel column chromatography (chloroform methanol). The objective fractions were condensed to give Compound 5 (66 mg, 32%).

$^1$H-NMR (CDCl$_3$) δ: 1.34 (d, J=5.1 Hz, 3H), 1.51 (dd, J=2.4 Hz, 14.4 Hz, 1H), 2.16 (m, 1H), 3.92-3.99 (m, 2H), 4.11 (dd, J=6.0 Hz, 14.4 Hz, 1H), 4.13 (s, 2H), 4.22 (dd, J=3.6 Hz, 13.2 Hz, 1H), 5.01 (m, 1H), 5.17 (m, 1H), 5.38 (m, 2H), 6.81 (m, 2H), 7.20-7.37 (m, 4H), 7.60-7.64 (m, 2H), 8.32 (s, 1H), 8.57 (s, 1H), 13.0 (s, 1H).

Step 3 Synthesis of Compound A-52

Compound 5 (65 mg, 0.39 mmol) was dissolved to TFA (1 ml). The mixture was stirred at room temperature for an hour. After the obtained reaction solution was condensed in vacuo, the residue was diluted with chloroform. The mixture was washed with sodium hydrogen carbonate aqueous solution and 5% citric acid aqueous solution. The organic phase was dried with sodium sulfate anhydrate. The solvent was removed in vacuo. Ethyl acetate was added to the obtained residue to solidify. The solids were filtrated to give Compound A-52 (45 mg, 84%).

LC/MS (ESI): 1.44 min, found 444 (M+1)

Example 7: Synthesis of Compound A-53

[Chemical Formula 61]

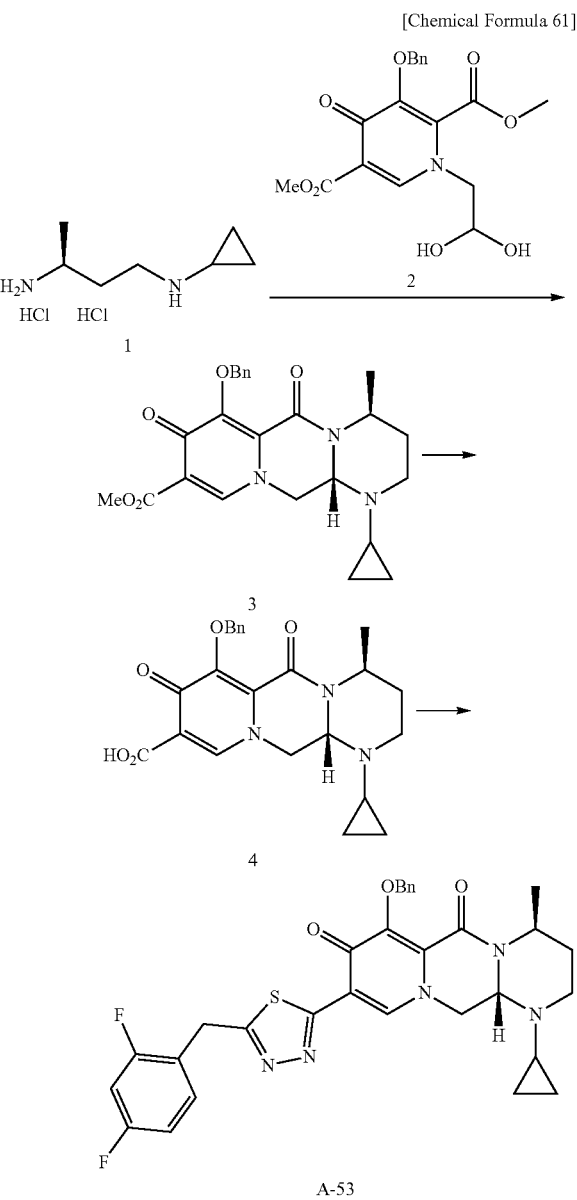

A-53

Step 1 Synthesis of Compound 3

Compound 1 (82 mg, 0.41 mmol) was dissolved to dichloromethane (15 mL) and methanol (3 mL). Triethylamine (165 mg, 1.63 mmol), Compound 2 (231 mg, 0.61 mmol) and acetic acid (25 mg, 0.41 mmol) were added. The mixture was stirred at 60° C. for 48 hours under heat reflux. Saturated ammonium chloride aqueous solution was added to the reaction mixture. The mixture was extracted with dichloromethane twice. After the organic phase was washed with brine, the mixture was died by sodium sulfate anhydrate. The solvent was removed in vacuo. The obtained residue was purified by silica-gel column chromatography (methanol chloroform) to give Compound 3 (114 mg, 64%).

LC/MS (EST): 438[M+1]

Step 2 Synthesis of Compound 4

Compound 3 (114 mg, 0.26 mmol) was dissolved to methanol (5 mL). After 2 mol/L sodium hydroxide aqueous solution (0.26 mL, 0.52 mmol) was added, the mixture was stirred at room temperature for 18 hours. Water was added to the reaction mixture. After the mixture was adjusted to pH6.8 with 1 mol/L hydrochloric acid aqueous solution, the mixture was extracted with chloroform. After the mixture was washed with brine, the mixture was dried with sodium sulfate anhydrate. The solvent was removed in vacuo to give Compound 4 (102 mg, 92%).

LC/MS (EST): 424[M+1]

Compound A-53 was synthesized by a similar procedure to Example 3 of Patent Document 15 (WO2013/054862) from Compound 4.

LC/MS (ESI): 500[M+1]

The following compound was synthesized by a similar procedure to Example 7.

TABLE 11

| No. | Structure | RT (min) | [M + H]+ | Method |
|---|---|---|---|---|
| A-54 | 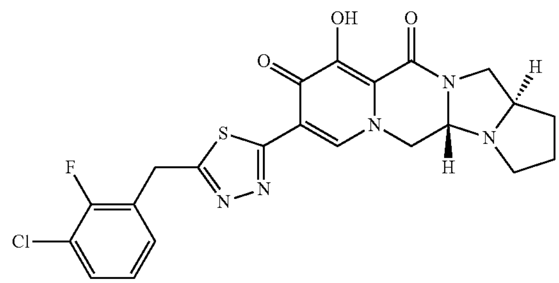 [SMILES: O=C1c2c(O)c(=O)c(-c3nnc(Cc4cccc(Cl)c4F)s3)cn2C[C@@H]2N1C[C@H]1CCCN12] | 1.53 | 488 | A |
| A-55 | 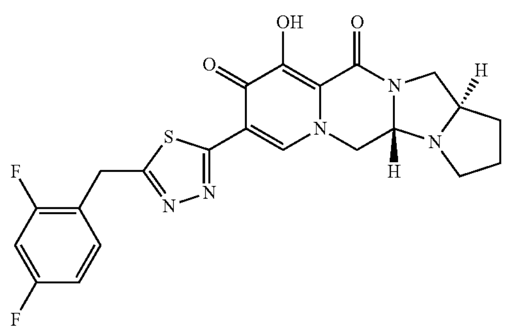 [SMILES: O=C1c2c(O)c(=O)c(-c3nnc(Cc4ccc(F)cc4F)s3)cn2C[C@@H]2N1C[C@H]1CCCN12] | 1.44 | 472.1 | A |
| A-56 | 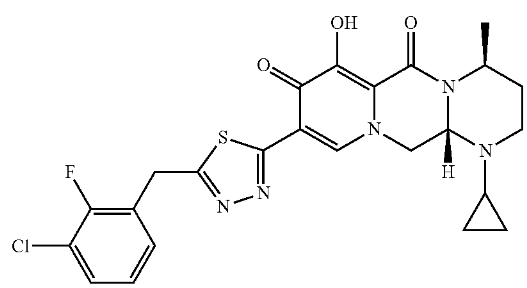 [SMILES: C[C@H]1CCN(C2CC2)[C@@H]2Cn3cc(-c4nnc(Cc5cccc(Cl)c5F)s4)c(=O)c(O)c3C(=O)N12] | 1.91 | 516 | A |

The following compound was synthesized by a similar procedure to any of the above procedure.

TABLE 12

| No. | Structure | RT (min) | [M + H]+ | Method |
|---|---|---|---|---|
| A-57 | 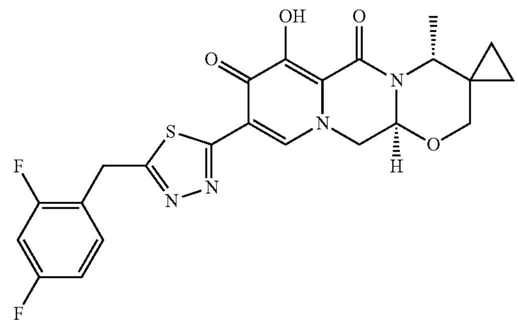 [SMILES: C[C@H]1N2C(=O)c3c(O)c(=O)c(-c4nnc(Cc5ccc(F)cc5F)s4)cn3C[C@@H]2OCC12CC2] | 1.80 | 487.2 | A |
| A-58 | 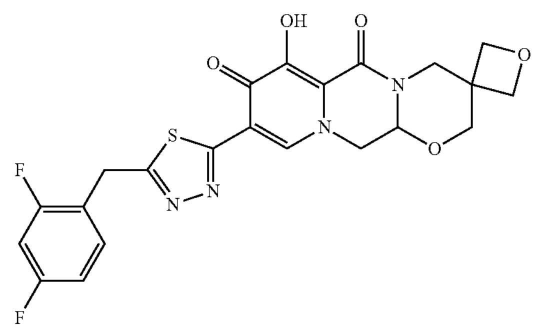 [SMILES: O=C1c2c(O)c(=O)c(-c3nnc(Cc4ccc(F)cc4F)s3)cn2CC2OCC3(COC3)CN12] | 1.45 | 489.2 | A |
| A-59 | 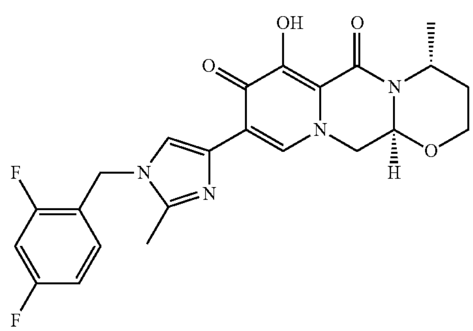 [SMILES: Cc1nc(-c2cn3c(c(O)c2=O)C(=O)N2[C@H](C)CCO[C@H]2C3)cn1Cc1ccc(F)cc1F] | 1.17 | 457.3 | A |
| A-60 | 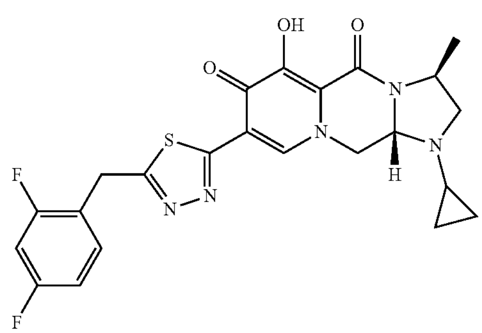 [SMILES: C[C@H]1CN(C2CC2)[C@@H]2Cn3cc(-c4nnc(Cc5ccc(F)cc5F)s4)c(=O)c(O)c3C(=O)N12] | 1.78 | 486.3 | A |

TABLE 12-continued
| No. | Structure | RT (min) | [M + H]+ | Method |
|---|---|---|---|---|
| A-61 | 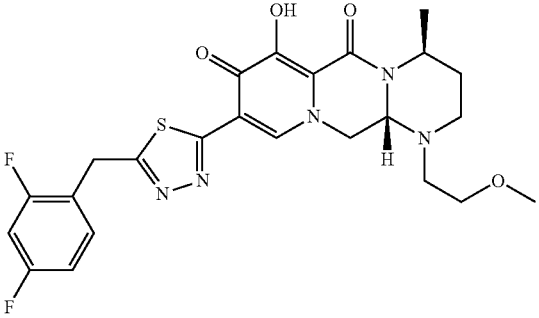 [SMILES: COCCN1CC[C@H](C)N2C(=O)c3c(O)c(=O)c(-c4nnc(Cc5ccc(F)cc5F)s4)cn3C[C@@H]12] | 1.52 | 518.3 | A |
TABLE 13
| No. | Structure | RT (min) | [M + H]+ | Method |
|---|---|---|---|---|
| A-62 | 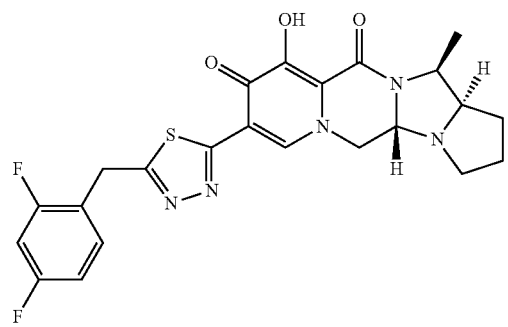 [SMILES: C[C@H]1[C@H]2CCCN2[C@@H]2Cn3cc(-c4nnc(Cc5ccc(F)cc5F)s4)c(=O)c(O)c3C(=O)N12] | 1.50 | 486.3 | A |
| A-63 | 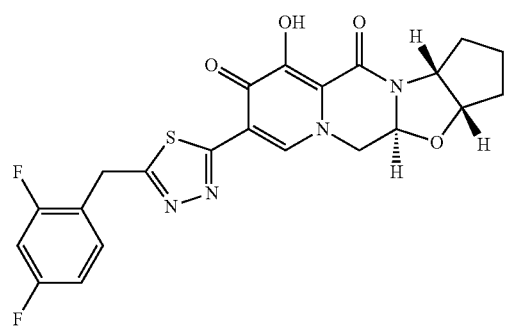 [SMILES: O=C1c2c(O)c(=O)c(-c3nnc(Cc4ccc(F)cc4F)s3)cn2C[C@@H]2O[C@H]3CCC[C@H]3N12] | 1.69 | 473.2 | A |
| A-64 | 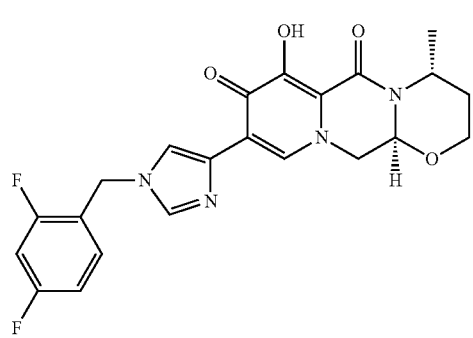 [SMILES: C[C@@H]1CCO[C@H]2Cn3cc(-c4cn(Cc5ccc(F)cc5F)cn4)c(=O)c(O)c3C(=O)N12] | 1.14 | 443.3 | A |

TABLE 13-continued

| No. | Structure | RT (min) | [M + H]+ | Method |
|---|---|---|---|---|
| A-65 | 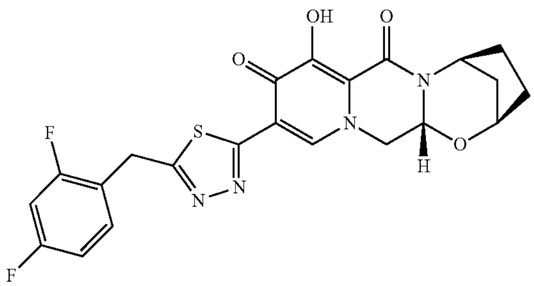 [SMILES: O=C1c2c(O)c(=O)c(-c3nnc(Cc4ccc(F)cc4F)s3)cn2C[C@H]2O[C@@H]3CC[C@@H](C3)N12] | 1.74 | 473.2 | A |
| A-66 | 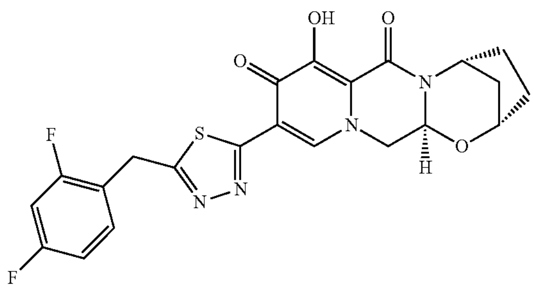 [SMILES: O=C1c2c(O)c(=O)c(-c3nnc(Cc4ccc(F)cc4F)s3)cn2C[C@@H]2O[C@H]3CC[C@H](C3)N12] | 1.73 | 473.2 | A |

TABLE 14

| No. | Structure | RT (min) | [M + H]+ | Method |
|---|---|---|---|---|
| A-67 | 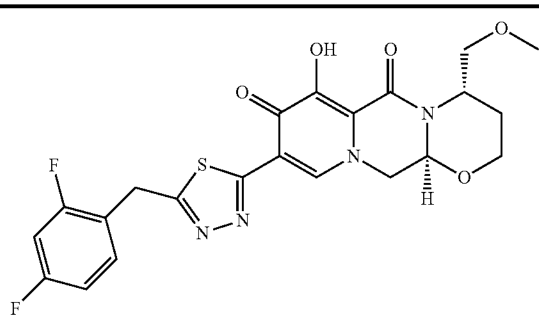 | 1.66 | 491.2 | A |
| A-68 | 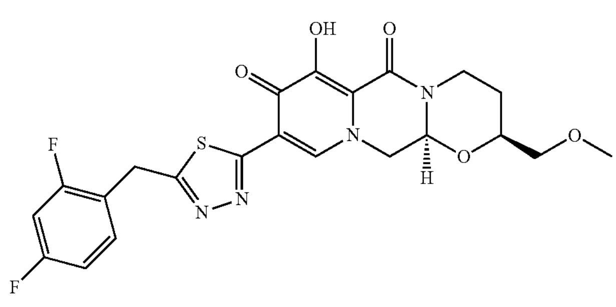 [SMILES: COC[C@@H]1CCN2C(=O)c3c(O)c(=O)c(-c4nnc(Cc5ccc(F)cc5F)s4)cn3C[C@@H]2O1] | 1.60 | 491.2 | A |

TABLE 14-continued

| No. | Structure | RT (min) | [M + H]+ | Method |
|---|---|---|---|---|
| A-69 | 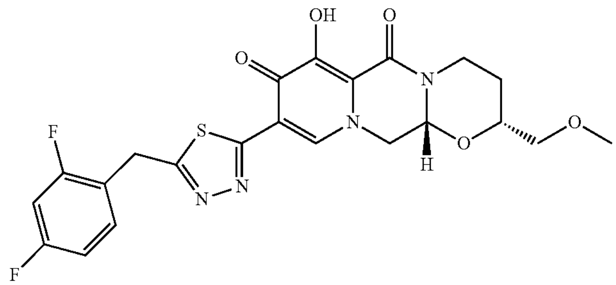 [SMILES: COC[C@H]1CCN2C(=O)c3c(O)c(=O)c(-c4nnc(Cc5ccc(F)cc5F)s4)cn3C[C@H]2O1] | 1.60 | 491.2 | A |
| A-70 | 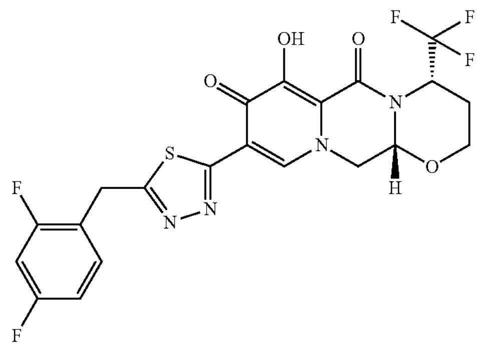 [SMILES: O=C1c2c(O)c(=O)c(-c3nnc(Cc4ccc(F)cc4F)s3)cn2C[C@H]2OCC[C@@H](C(F)(F)F)N12] | 1.81 | 515.2 | A |
| A-71 | 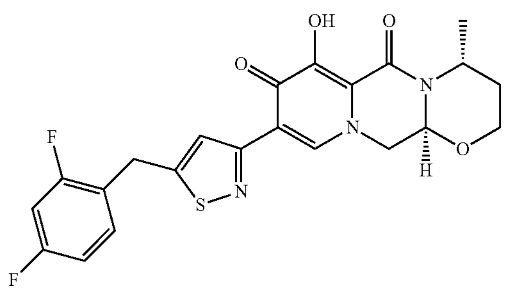 [SMILES: C[C@@H]1CCO[C@H]2Cn3cc(-c4cc(Cc5ccc(F)cc5F)sn4)c(=O)c(O)c3C(=O)N12] | 1.87 | 460.3 | B |

TABLE 15

| No. | Structure | RT (min) | [M + H]+ | Method |
|---|---|---|---|---|
| A-72 | 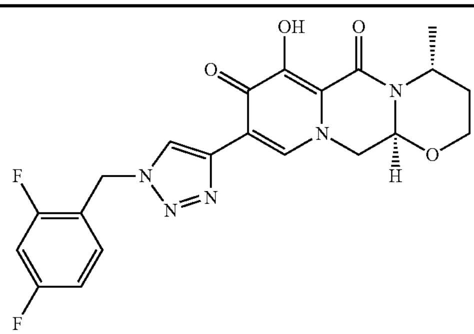 | 1.47 | 444.3 | A |

TABLE 15-continued

| No. | Structure | RT (min) | [M + H]+ | Method |
|-----|-----------|----------|----------|--------|
| A-73 | 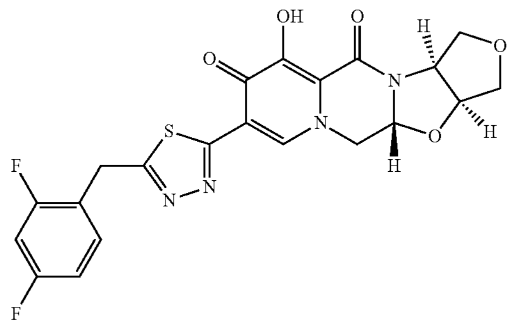 [SMILES: O=C1c2c(O)c(=O)c(-c3nnc(Cc4ccc(F)cc4F)s3)cn2C[C@H]2O[C@@H]3COC[C@@H]3N12] | 1.46 | 475.2 | A |
| A-74 | 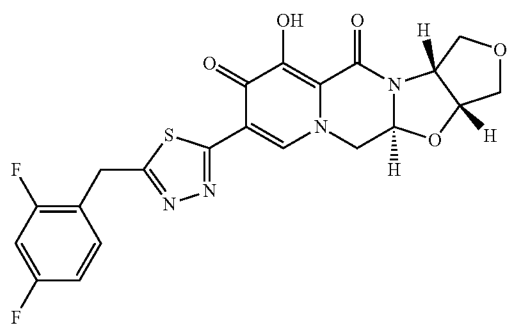 [SMILES: O=C1c2c(O)c(=O)c(-c3nnc(Cc4ccc(F)cc4F)s3)cn2C[C@@H]2O[C@H]3COC[C@H]3N12] | 1.46 | 475.2 | A |
| A-75 | 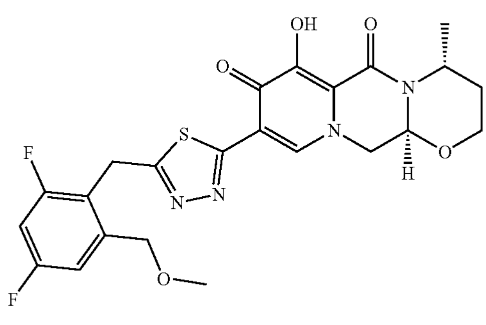 [SMILES: COCc1cc(F)cc(F)c1Cc1nnc(-c2cn3c(c(O)c2=O)C(=O)N2[C@H](C)CCO[C@H]2C3)s1] | 1.69 | 505.2 | A |
| A-76 | 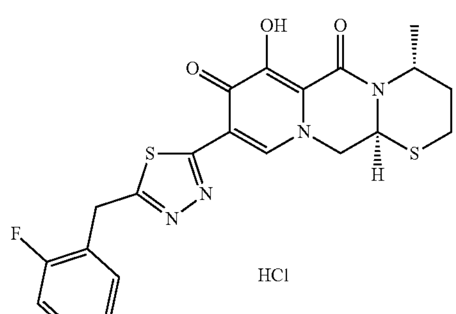 | 1.81 | 477.1 | A |

TABLE 16

| No. | Structure | RT (min) | [M + H]+ | Method |
|---|---|---|---|---|
| A-77 | 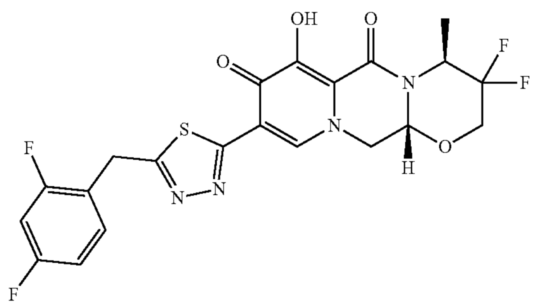 [SMILES: C[C@@H]1N2C(=O)c3c(O)c(=O)c(-c4nnc(Cc5ccc(F)cc5F)s4)cn3C[C@H]2OCC1(F)F] | 1.76 | 497.2 | A |
| A-78 | 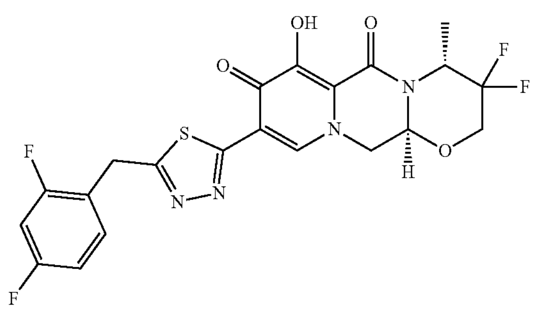 [SMILES: C[C@H]1N2C(=O)c3c(O)c(=O)c(-c4nnc(Cc5ccc(F)cc5F)s4)cn3C[C@@H]2OCC1(F)F] | 1.74 | 497.2 | A |
| A-79 | 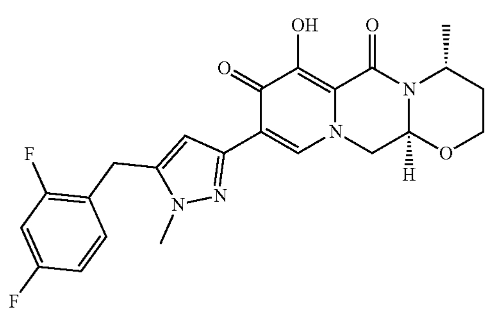 [SMILES: C[C@@H]1CCO[C@H]2Cn3cc(-c4cc(Cc5ccc(F)cc5F)n(C)n4)c(=O)c(O)c3C(=O)N12] | 1.60 | 457.2 | A |
| A-80 | 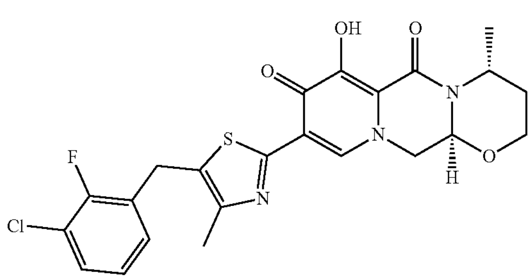 [SMILES: Cc1nc(-c2cn3c(c(O)c2=O)C(=O)N2[C@H](C)CCO[C@H]2C3)sc1Cc1cccc(Cl)c1F] | 2.06 | 490.2 | A |

Example 8: Synthesis of Compound B-1

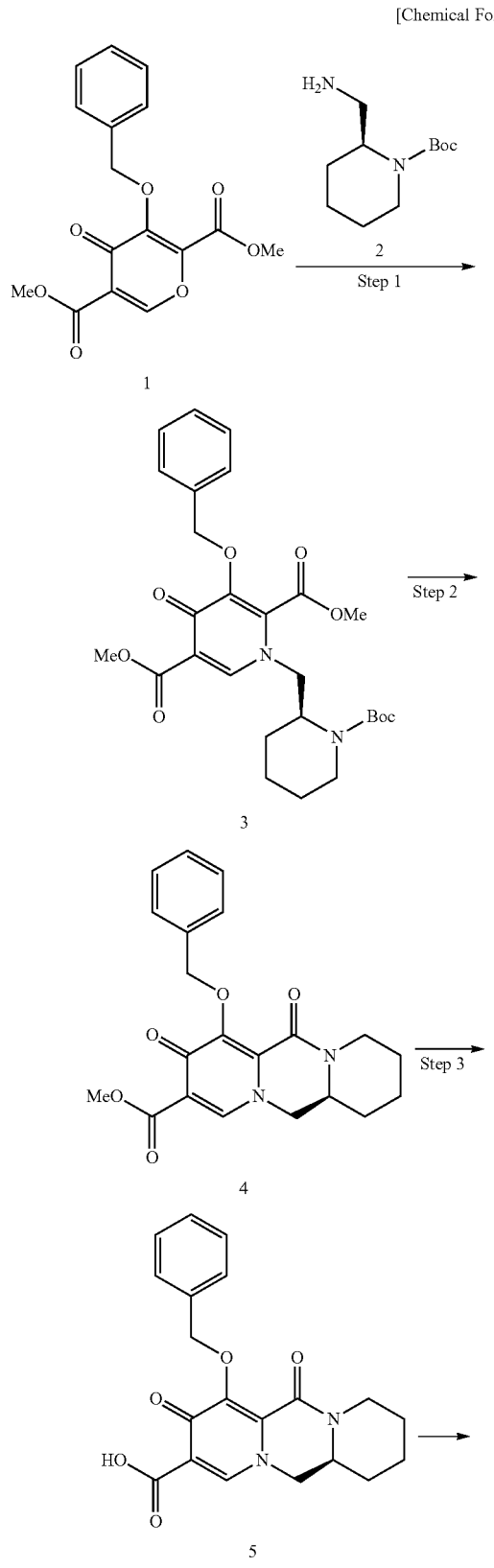

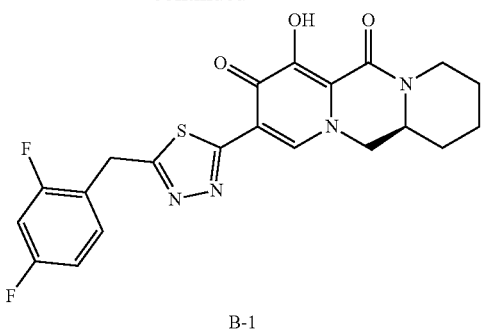

Step 1

Compound 1 (7.43 g, 23.3 mmol) and Compound 2 (5.00 g, 23.3 mmol) were added to toluene (75 ml). The mixture was stirred at 100° C. for 5 hours. After the reaction mixture was cooled to room temperature, the solvent was removed in vacuo. The obtained crude was purified by silica-gel column chromatography and eluted with n-hexaneethyl acetate to give Compound 3 (7.78 g, 65%).

MS: m/z=515 [M+H]+

Step 2

Compound 3 (7.78 g, 15.1 mmol) obtained by Step 1 was dissolved to 4 mol/L hydrochloric acid/ethyl acetate solution (80 ml). The mixture was stirred at room temperature for 30 minutes. After the solvent was removed in vacuo, toluene and trimethylamine were added. The mixture was stirred at 80° C. for 2 hours. After the reaction mixture was cooled to room temperature, the solvent was removed in vacuo. The obtained crude was washed with diethyl ether to give Compound 4 (5.45 g, 94%).

MS: m/z=383 [M+H]+

Step 3

Compound 4 (5.45 g, 14.3 mmol) obtained by Step 2 was dissolved to methanol (100 ml) and tetrahydrofuran (50 ml). 2 mol/L sodium hydroxide aqueous solution (35.6 ml, 71.3 mmol) was added. The mixture was stirred at room temperature for an hour. After 1 mol/L hydrochloric acid was added to the reaction mixture to be acidic, the obtained white precipitate was filtrated. The filtrate was washed with water and diethyl ether and dried to give Compound 5 (4.89 g, 93%).

MS: m/z=369 [M+H]+

Compound B-1 was synthesized by a similar procedure to Example 3 of Patent Document 15 (WO2013/054862) from Compound 5.

MS: m/z=445 [M+H]+

The following compound was synthesized by a similar procedure to Example 8.

TABLE 17

| No. | Structure | RT (min) | [M + H]+ | Method |
|---|---|---|---|---|
| B-2 | 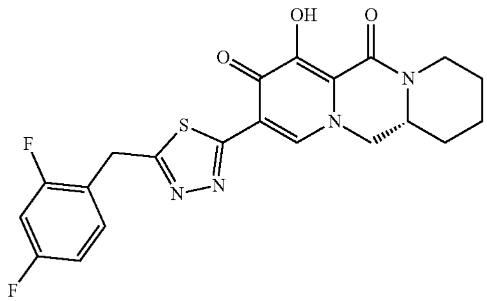 | 1.70 | 445 | B |
| B-3 | 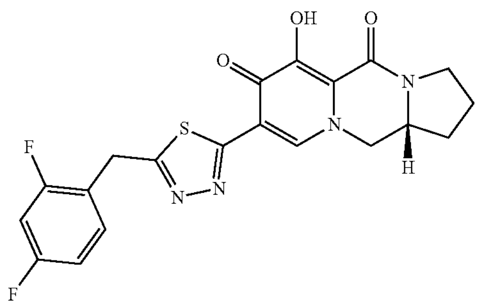 [SMILES: O=C1c2c(O)c(=O)c(-c3nnc(Cc4ccc(F)cc4F)s3)cn2C[C@H]2CCCN12] | 1.51 | 431.1 | A |
| B-4 | 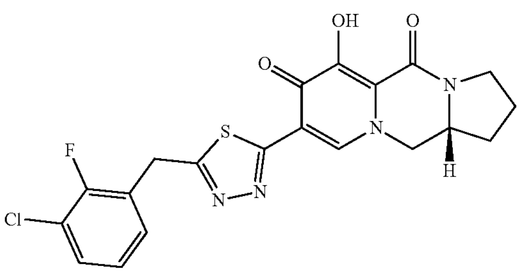 [SMILES: O=C1c2c(O)c(=O)c(-c3nnc(Cc4cccc(Cl)c4F)s3)cn2C[C@H]2CCCN12] | 1.59 | 447.2 | A |
| B-5 | 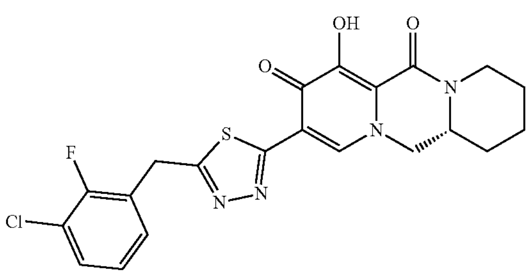 | 1.79 | 461 | B |
| B-6 | 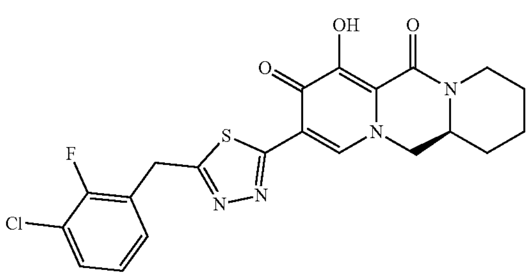 [SMILES: O=C1c2c(O)c(=O)c(-c3nnc(Cc4cccc(Cl)c4F)s3)cn2C[C@@H]2CCCCN12] | 1.80 | 461 | B |

TABLE 17-continued

| No. | Structure | RT (min) | [M + H]+ | Method |
|---|---|---|---|---|
| B-7 | 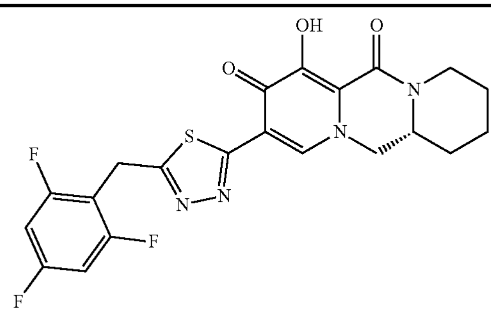 | 1.73 | 463 | B |

TABLE 18

| No. | Structure | RT (min) | [M + H]+ | Method |
|---|---|---|---|---|
| B-8 | 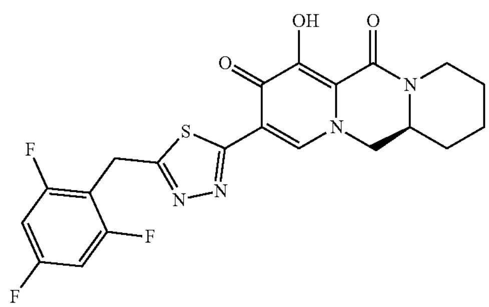 [SMILES: O=C1c2c(O)c(=O)c(-c3nnc(Cc4c(F)cc(F)cc4F)s3)cn2C[C@@H]2CCCCN12] | 1.73 | 463 | B |
| B-9 | 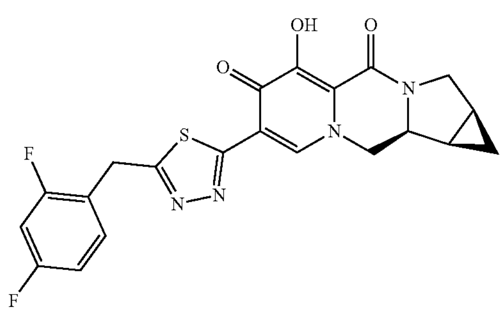 [SMILES: O=C1c2c(O)c(=O)c(-c3nnc(Cc4ccc(F)cc4F)s3)cn2C[C@@H]2[C@@H]3C[C@@H]3CN12] | 1.61 | 443 | B |
| B-10 | 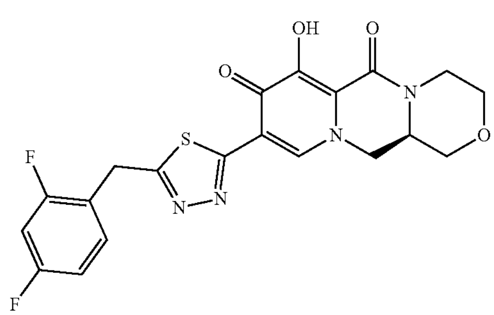 [SMILES: O=C1c2c(O)c(=O)c(-c3nnc(Cc4ccc(F)cc4F)s3)cn2C[C@@H]2COCCN12] | 1.5 | 447 | B |

TABLE 18-continued

| No. | Structure | RT (min) | [M + H]+ | Method |
|---|---|---|---|---|
| B-11 | 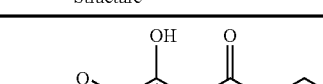 | 1.5 | 447 | B |

Example 9: Synthesis of Compound B-12

[Chemical Formula 63]

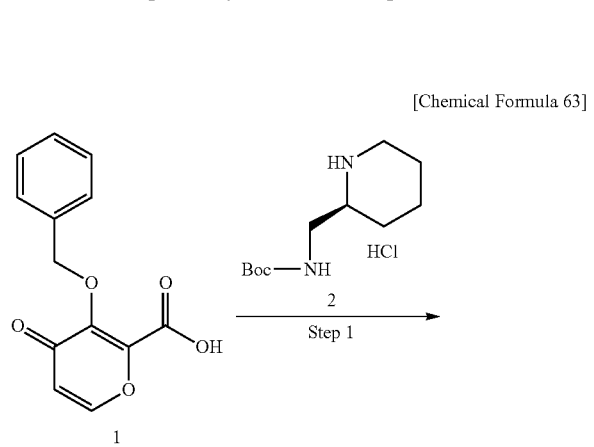

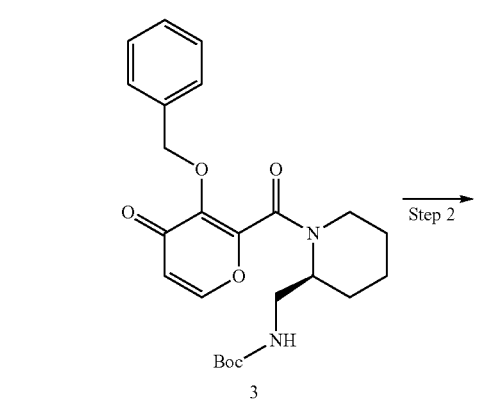

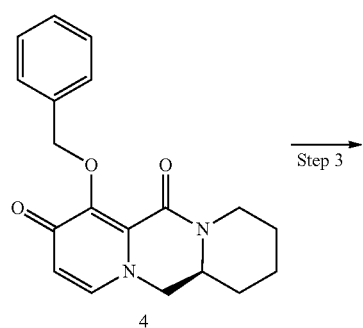

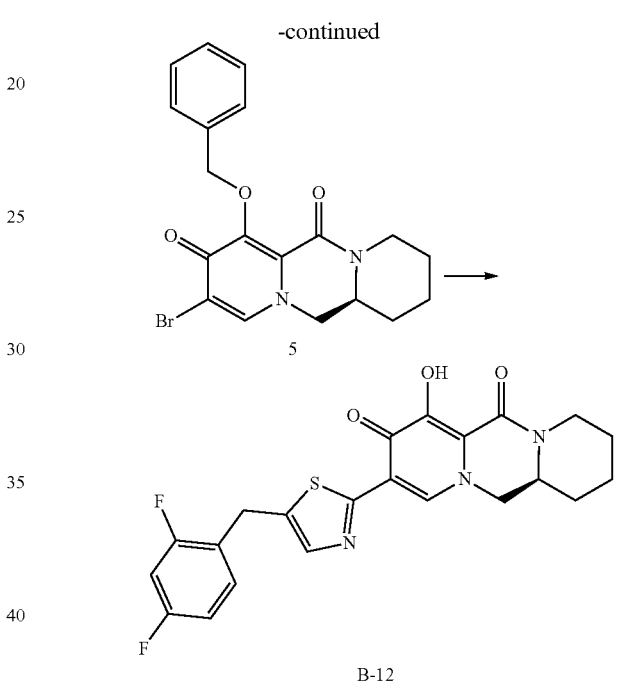

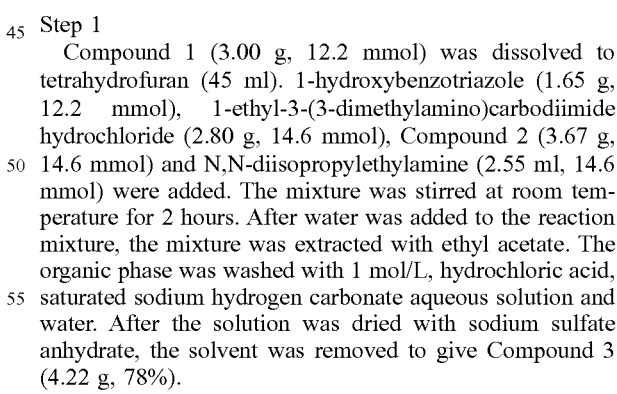

B-12

Step 1

Compound 1 (3.00 g, 12.2 mmol) was dissolved to tetrahydrofuran (45 ml). 1-hydroxybenzotriazole (1.65 g, 12.2 mmol), 1-ethyl-3-(3-dimethylamino)carbodiimide hydrochloride (2.80 g, 14.6 mmol), Compound 2 (3.67 g, 14.6 mmol) and N,N-diisopropylethylamine (2.55 ml, 14.6 mmol) were added. The mixture was stirred at room temperature for 2 hours. After water was added to the reaction mixture, the mixture was extracted with ethyl acetate. The organic phase was washed with 1 mol/L, hydrochloric acid, saturated sodium hydrogen carbonate aqueous solution and water. After the solution was dried with sodium sulfate anhydrate, the solvent was removed to give Compound 3 (4.22 g, 78%).

MS: m/z=465 [M+H]+

Step 2

Compound 3 (4.22 g, 9.54 mmol) obtained by Step 1 was dissolved to 4 mol/L hydrochloric acid/ethyl acetate solution (45 ml). The mixture was stirred at room temperature for 30 minutes. After the solvent was removed in vacuo, ethanol was added. The reaction mixture was adjusted to basicity with saturated sodium carbonate aqueous solution. The mixture was stirred at 50° C. for 2 hours. After the reaction mixture was cooled to room temperature, the mixture was extracted with chloroform. The organic phase was dried with sodium sulfate anhydrate. After the solvent was removed in vacuo, the obtained crude was crystalized with dichloromethane and diisopropyl ether to give Compound 4 (2.33 g, 75%).

MS: m/z=325 [M+H]+

Step 3

Compound 4 (2.33 g, 7.18 mmol) obtained by Step 2 was dissolved to N,N-dimethylformamide (30 ml). N-bromosuccinimide (1.34 g, 7.54 mmol) was added. The mixture was stirred at room temperature for 30 minutes. After water was added to the reaction mixture, the mixture was extracted with dichloromethane. After the organic phase was washed with water, the mixture was dried with sodium sulfate anhydrate. After the solvent was removed in vacuo, the obtained crude was washed with dichloromethane and diisopropyl ether to give Compound 5 (2.80 g, 97%).

Compound B-12 was synthesized by a similar procedure to Example 1 of Patent Document 15 (WO2013/054862) from Compound 5.

The following compound was synthesized by a similar procedure to Example 9.

TABLE 19

| No. | Structure | RT (min) | [M + H]+ | Method |
| --- | --- | --- | --- | --- |
| B-13 | 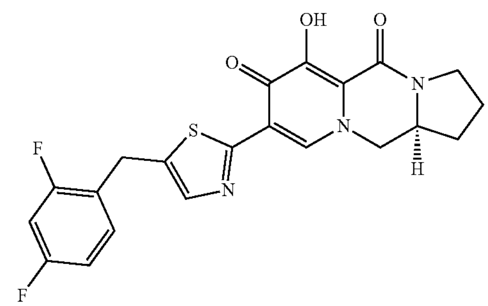 [SMILES: O=C1c2c(O)c(=O)c(-c3ncc(Cc4ccc(F)cc4F)s3)cn2C[C@@H]2CCCN12] | 1.67 | 430 | A |
| B-14 | 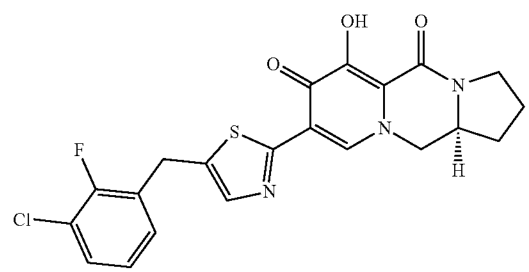 [SMILES: O=C1c2c(O)c(=O)c(-c3ncc(Cc4cccc(Cl)c4F)s3)cn2C[C@@H]2CCCN12] | 1.8 | 446 | A |
| B-15 | 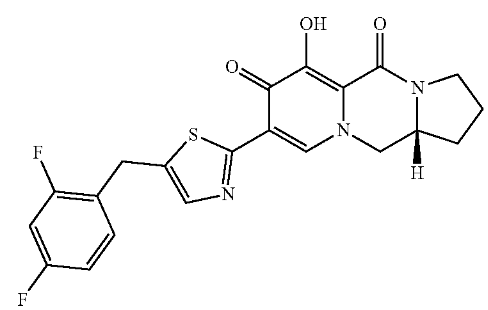 | 1.75 | 430 | A |
| B-16 | 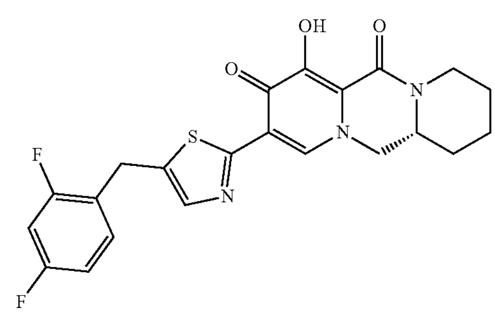 [SMILES: O=C1c2c(O)c(=O)c(-c3ncc(Cc4ccc(F)cc4F)s3)cn2C[C@H]2CCCCN12] | 1.87 | 444 | B |

TABLE 19-continued
| No. | Structure | RT (min) | [M + H]+ | Method |
|---|---|---|---|---|
| B-17 | 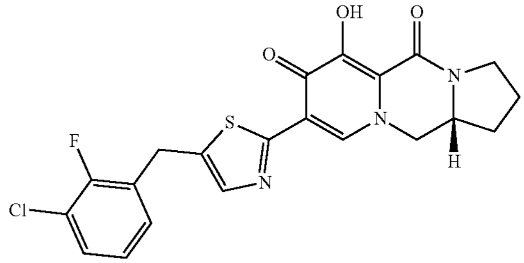 [SMILES: O=C1c2c(O)c(=O)c(-c3ncc(Cc4cccc(Cl)c4F)s3)cn2C[C@H]2CCCN12] | 1.8 | 446.2 | A |
| B-18 | 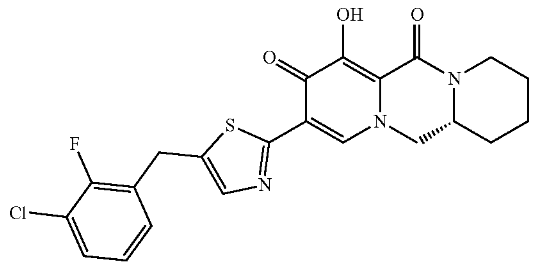 [SMILES: O=C1c2c(O)c(=O)c(-c3ncc(Cc4cccc(Cl)c4F)s3)cn2C[C@H]2CCCCN12] | 1.98 | 460 | B |
TABLE 20
| No. | Structure | RT (min) | [M + H]+ | Method |
|---|---|---|---|---|
| B-19 | 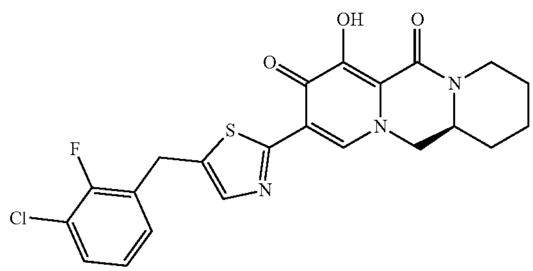 [SMILES: O=C1c2c(O)c(=O)c(-c3ncc(Cc4cccc(Cl)c4F)s3)cn2C[C@@H]2CCCCN12] | 1.98 | 460 | B |
[Chemical Formula 64]
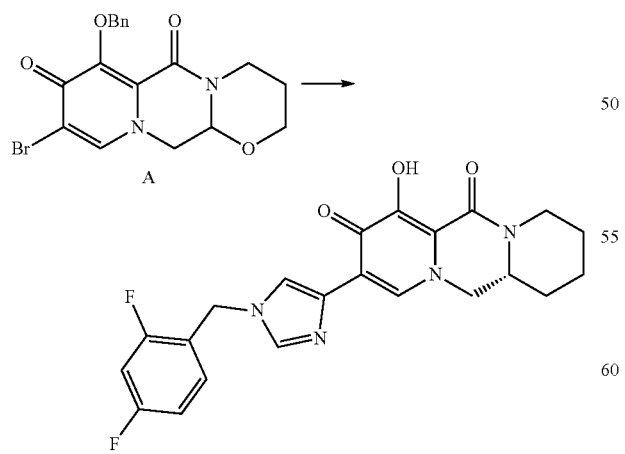
Compound B-20 was synthesized from Compound A by a similar procedure to Example 2.

TABLE 21

| No. | Structure | RT (min) | [M + H]+ | Method |
|---|---|---|---|---|
| B-20 | 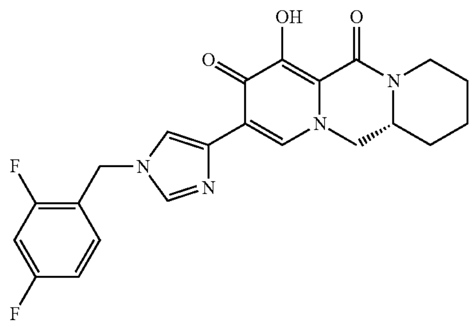 [SMILES: O=C1c2c(O)c(=O)c(-c3cn(Cc4ccc(F)cc4F)cn3)cn2C[C@H]2CCCCN12] | 1.19 | 427 | A |

The following compound was synthesized by a similar procedure to any of the above procedure.

TABLE 22

| No. | Structure | RT (min) | [M + H]+ | Method |
|---|---|---|---|---|
| B-21 | 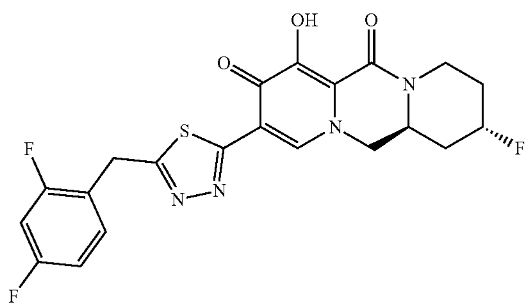 [SMILES: O=C1c2c(O)c(=O)c(-c3nnc(Cc4ccc(F)cc4F)s3)cn2C[C@@H]2C[C@@H](F)CCN12] | 1.61 | 463.1 | B |
| B-22 | 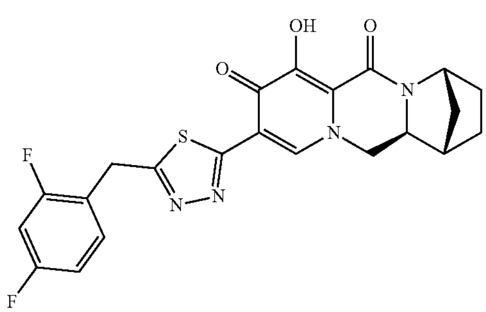 [SMILES: O=C1c2c(O)c(=O)c(-c3nnc(Cc4ccc(F)cc4F)s3)cn2C[C@@H]2[C@H]3CC[C@H](C3)N12] | 1.65 | 457.1 | B |

Example 10: Synthesis of Compound C-1
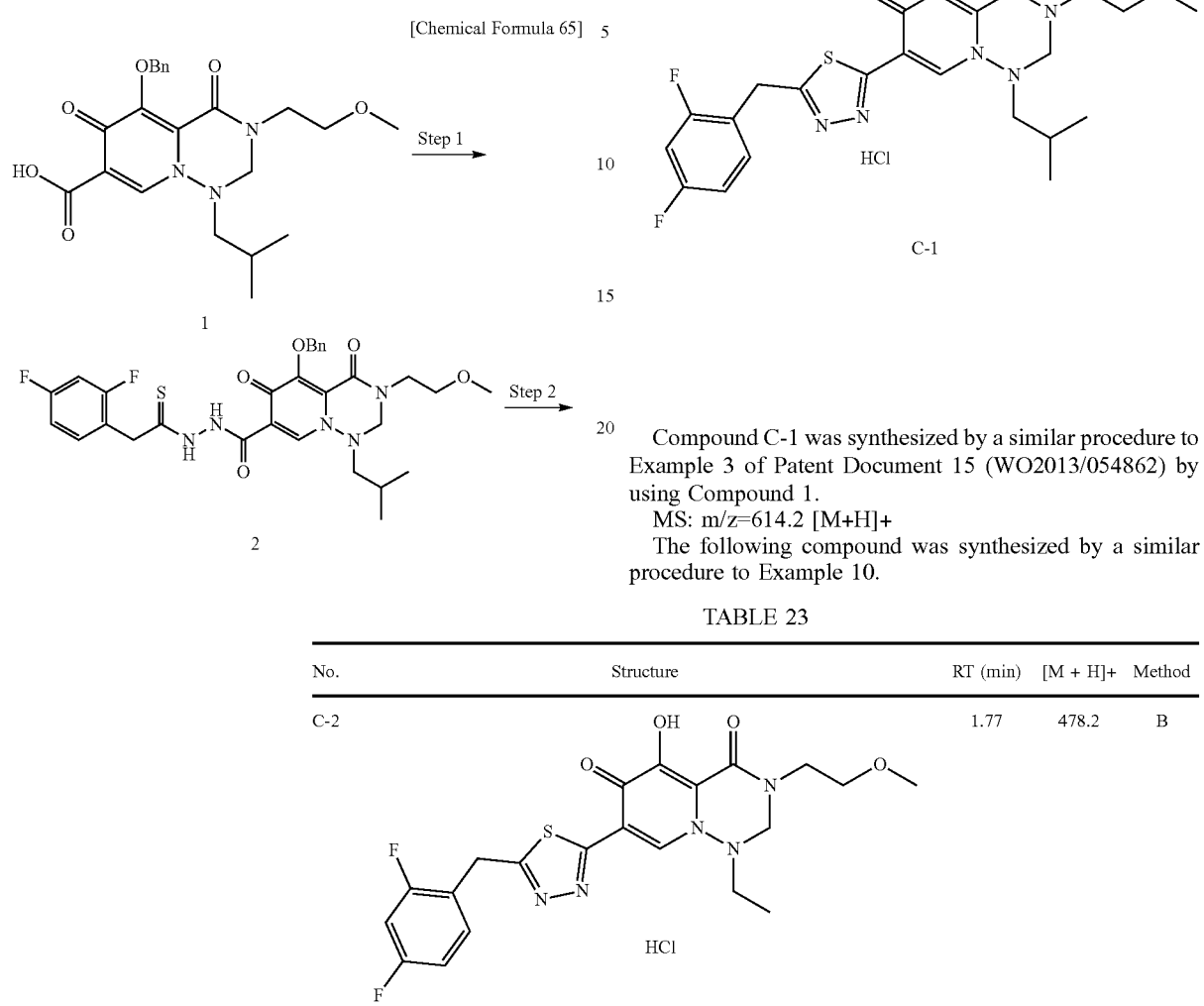
Compound C-1 was synthesized by a similar procedure to Example 3 of Patent Document 15 (WO2013/054862) by using Compound 1.
MS: m/z=614.2 [M+H]+
The following compound was synthesized by a similar procedure to Example 10.
TABLE 23
| No. | Structure | RT (min) | [M + H]+ | Method |
|-----|-----------|----------|----------|--------|
| C-2 | 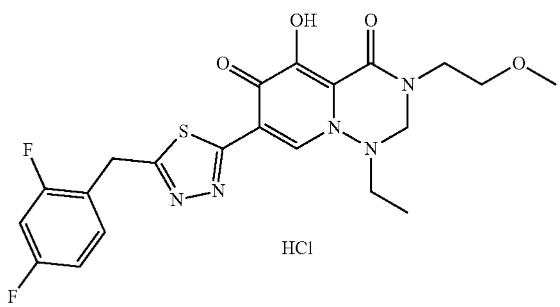 [SMILES: CCN1CN(CCOC)C(=O)c2c(O)c(=O)c(-c3nnc(Cc4ccc(F)cc4F)s3)cn21 ; Cl] | 1.77 | 478.2 | B |
| C-3 | 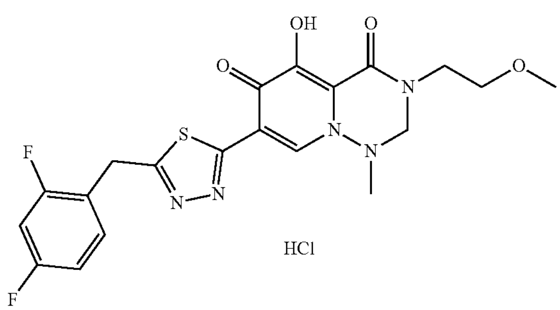 [SMILES: COCCN1CN(C)n2cc(-c3nnc(Cc4ccc(F)cc4F)s3)c(=O)c(O)c2C1=O ; Cl] | 1.65 | 464.3 | B |
| C-4 | 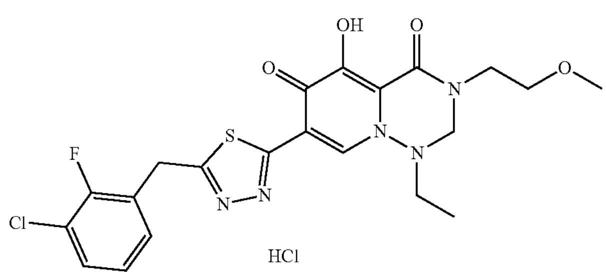 [SMILES: CCN1CN(CCOC)C(=O)c2c(O)c(=O)c(-c3nnc(Cc4cccc(Cl)c4F)s3)cn21 ; Cl] | 1.88 | 494 | B |

TABLE 23-continued
| No. | Structure | RT (min) | [M + H]+ | Method |
|---|---|---|---|---|
| C-5 | 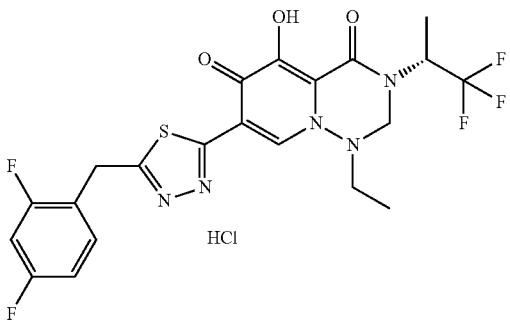 [SMILES: CCN1CN([C@H](C)C(F)(F)F)C(=O)c2c(O)c(=O)c(-c3nnc(Cc4ccc(F)cc4F)s3)cn21 ; Cl] | 2.01 | 516 | A |
| C-6 | 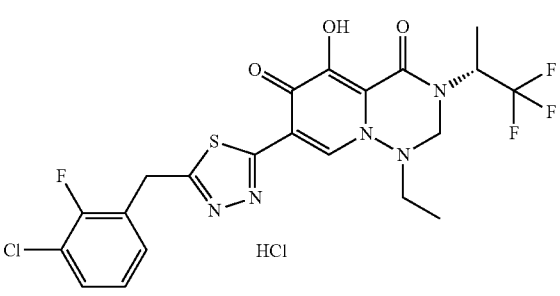 [SMILES: CCN1CN([C@H](C)C(F)(F)F)C(=O)c2c(O)c(=O)c(-c3nnc(Cc4cccc(Cl)c4F)s3)cn21 ; Cl] | 2.14 | 532 | A |
| C-7 | 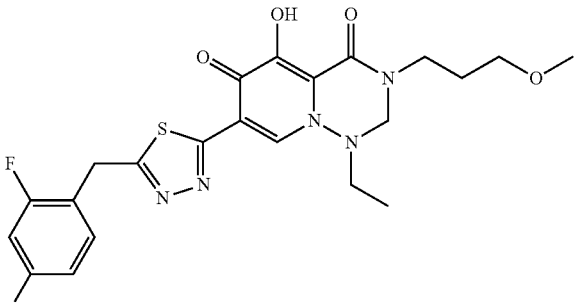 | 1.74 | 492 | A |
TABLE 24
| No. | Structure | RT (min) | [M + H]+ | Method |
|---|---|---|---|---|
| C-8 | 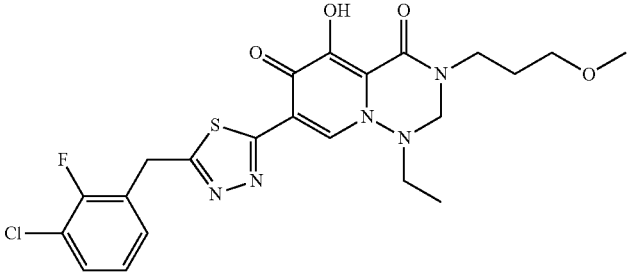 [SMILES: CCN1CN(CCCOC)C(=O)c2c(O)c(=O)c(-c3nnc(Cc4cccc(Cl)c4F)s3)cn21] | 1.87 | 508 | A |

Example 11: Synthesis of Compound C-10
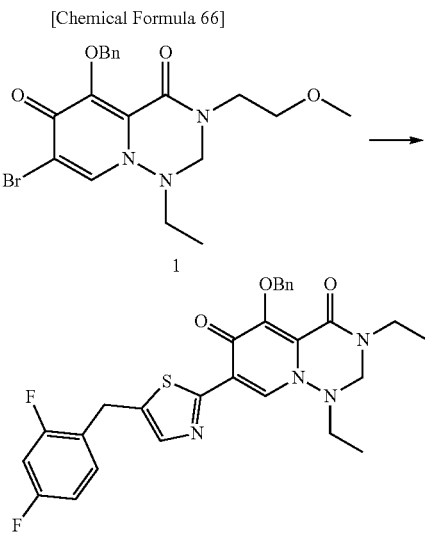
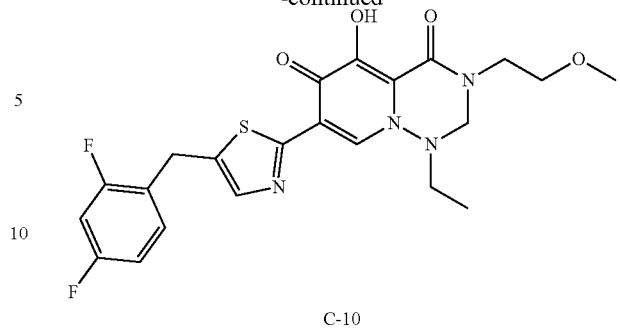
Compound C-10 was synthesized by a similar procedure to Example 1 of Patent Document 15 (WO2013/054862) from Compound 1 synthesized by a similar procedure to Example 145 of Patent Document 13 (WO2010/147068).
LC/MS (ESI): 477 (M+1)
The following compound was synthesized by a similar procedure to Example 11.
TABLE 25
| No. | Structure | RT (min) | [M + H]+ | Method |
|---|---|---|---|---|
| C-11 | 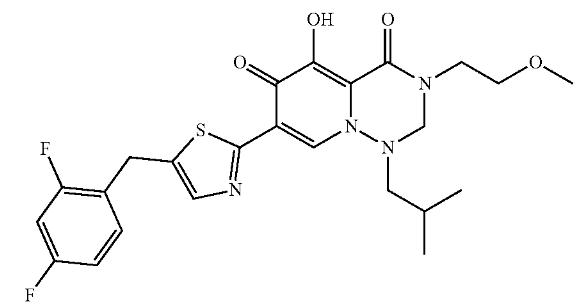 [SMILES: COCCN1CN(CC(C)C)n2cc(-c3ncc(Cc4ccc(F)cc4F)s3)c(=O)c(O)c2C1=O] | 2.31 | 505 | B |
| C-12 | 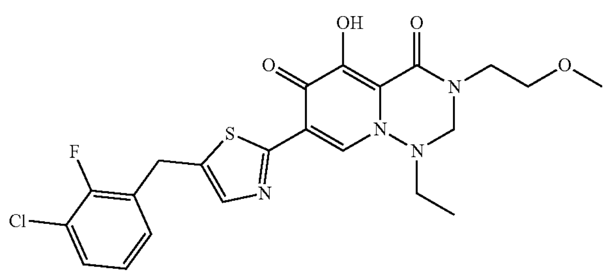 [SMILES: CCN1CN(CCOC)C(=O)c2c(O)c(=O)c(-c3ncc(Cc4cccc(Cl)c4F)s3)cn21] | 2.12 | 494 | B |
| C-13 | 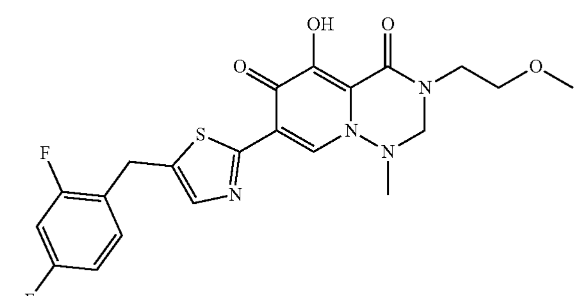 | 1.87 | 463 | B |

Example 12: Synthesis of Compound C-14

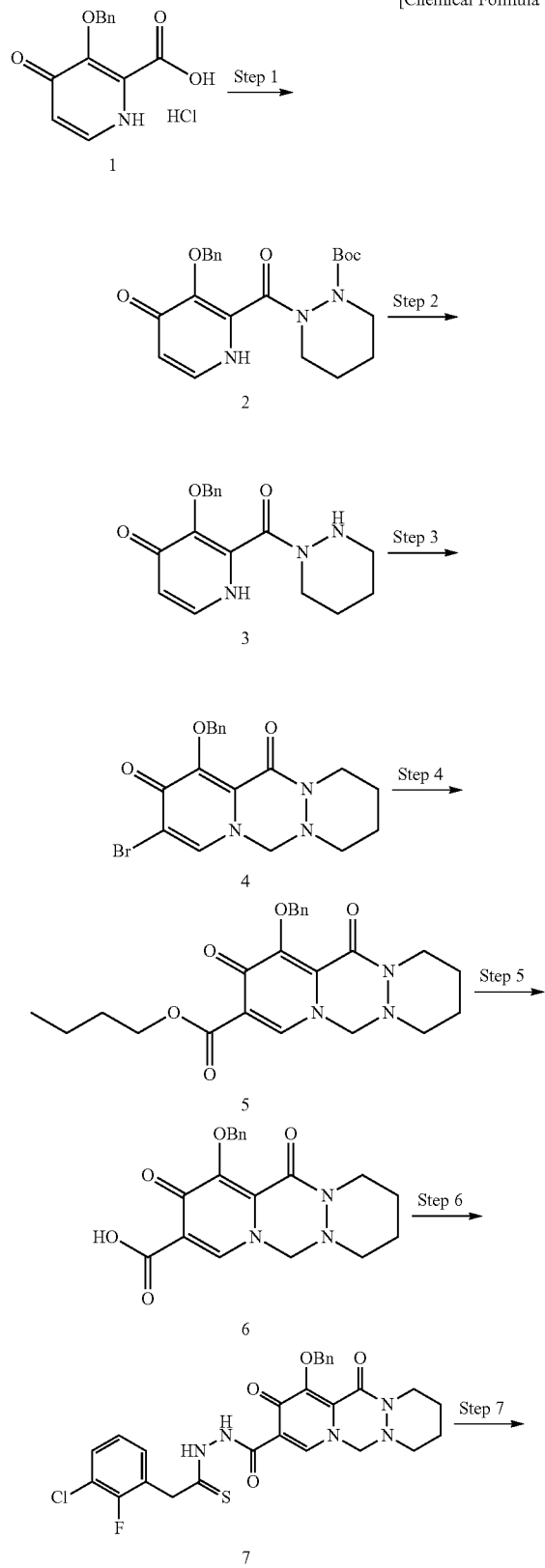

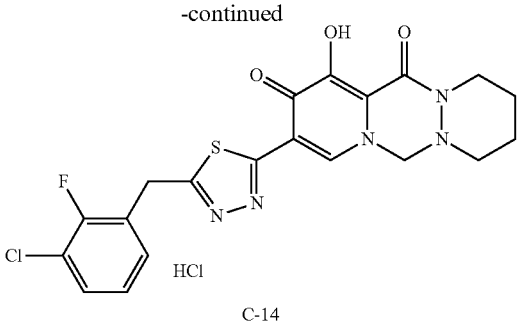

C-14

Step 1

Compound 2 was synthesized by a similar procedure to Compound 177A of Patent Document 13 (WO2010/147068).

Step 2

4 mol/L hydrochloric acid (ethyl acetate solution, 2.6 ml, 10.4 mmol) was added to ethyl acetate (3 ml) solution of Compound 2 (1.137 g, 2.75 mmol). The mixture was stirred at room temperature for 2 hours. After the mixture was neutralized with sodium hydrogen carbonate aqueous solution, the mixture was extracted with chloroform three times. After the organic phase was dried with sodium sulfate anhydrate, the solvent was removed in vacuo to give Compound 3 (768 mg, 89%).

Step 3

Paraformaldehyde (72 mg, 2.39 mmol) was added to DMF (3.7 ml) solution of Compound 3 (749 mg, 2.39 mmol). The mixture was stirred at 120° C. for an hour in an oil bath. After cooling to room temperature, the deposited solids were dissolved to DMF (3.7 ml) and dichloromethane (7.5 ml). N-bromosuccinimide (425 mg, 2.39 mmol) was added. After the mixture was stirred at room temperature for an hour, water was added. The mixture was extracted with ethyl acetate. After the organic phase was washed with water and brine, the organic phase was dried with sodium sulfate anhydrate. The solvent was removed in vacuo. After the obtained solids were suspended to ethyl acetate/isopropyl ether (1:2), the solids were filtrated to give Compound 4 (632 mg, 65%).

LC/MS (ESI): 1.30 min. found 404 (M+1)

Step 4

$PdCl_2$ (dppf) $CH_2Cl_2$ (121 mg, 0.148 mmol) and triethylamine (1.03 ml, 7.42 mmol) were added to n-butanol (6 ml) solution of Compound 4 (600 mg, 1.48 mmol) to exchange with carbon monoxide. After the mixture was stirred at 110° C. for 2 hours under heat reflux in an oil bath, the mixture was cooled to room temperature. After insoluble matter was removed by filtration, the filtrate was condensed in vacuo. The obtained residue was purified by silica-gel column chromatography (chloroform methanol, 99:1 to 95:5). The objective fractions were condensed in vacuo to give Compound 5 (404 mg, 64%).

LC/MS (ESI): 1.69 min. found 426 (M+1)

Step 5

2 mol/L sodium hydroxide aqueous solution (0.94 ml, 1.88 mmol) was added to methanol (4 ml) solution of Compound 5 (400 mg, 0.94 mmol). After the mixture was stirred at room temperature for 2 hours, 2 mol/L hydrochloric acid was added. The deposited solids were filtrated to give Compound 6 (234 mg, 67%).

LC/MS (EST): 1.50 min. found 370 (M+1)

Compound C-14 was synthesized by a similar procedure to Example 3 of Patent Document 15 (WO2013/054862) from Compound 6.

LC/MS (ESI): 462 (M+1)

The following compound was synthesized by a similar procedure to Example 12.

TABLE 26

| No. | Structure | RT (min) | [M + H]+ | Method |
|---|---|---|---|---|
| C-15 | 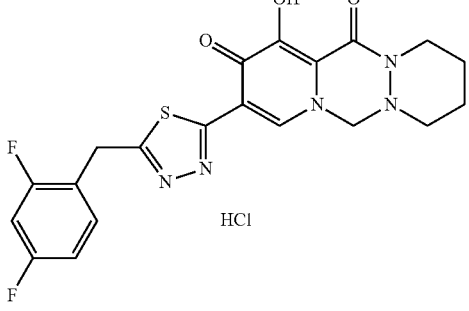 | 1.63 | 446 | A |
| C-16 | 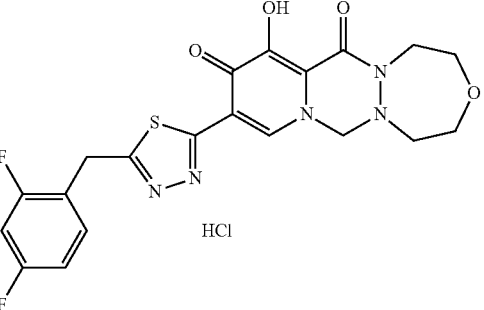 | 1.48 | 462 | A |
| C-17 | 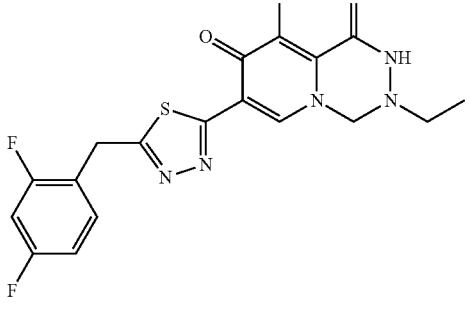 | 1.5 | 420.1 | A |
| C-18 | 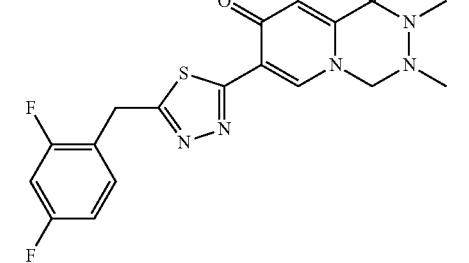 | 1.53 | 420.1 | A |

TABLE 26-continued

| No. | Structure | RT (min) | [M + H]+ | Method |
|---|---|---|---|---|
| C-19 | 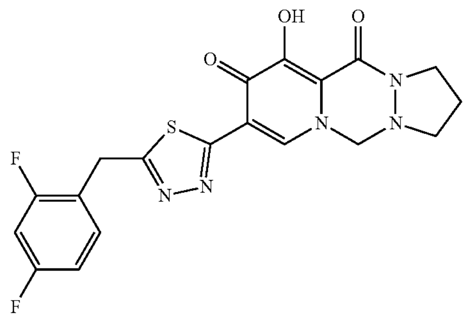 [SMILES: O=C1c2c(O)c(=O)c(-c3nnc(Cc4ccc(F)cc4F)s3)cn2CN2CCCN12] | 1.43 | 432 | A |

The following compound was synthesized by a similar procedure to any of the above procedure.

TABLE 27

| No. | Structure | RT (min) | [M + H]+ | Method |
|---|---|---|---|---|
| C-20 | 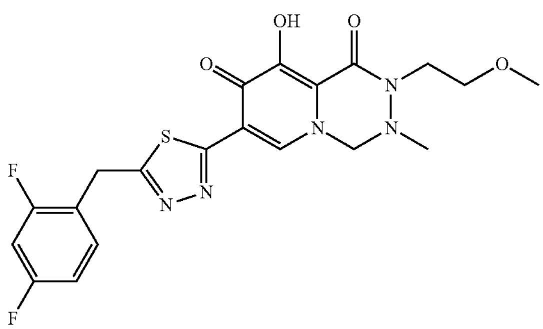 [SMILES: COCCN1C(=O)c2c(O)c(=O)c(-c3nnc(Cc4ccc(F)cc4F)s3)cn2CN1C] | 1.79 | 464.2 | A |
| C-21 | 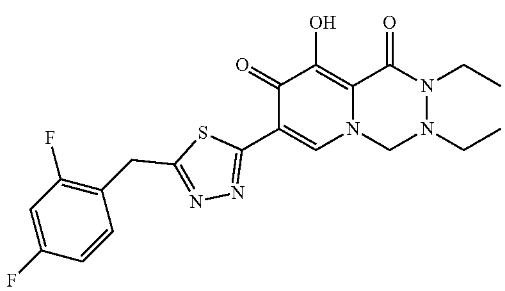 [SMILES: CCN1Cn2cc(-c3nnc(Cc4ccc(F)cc4F)s3)c(=O)c(O)c2C(=O)N1CC] | 1.81 | 448.2 | A |
| C-22 | 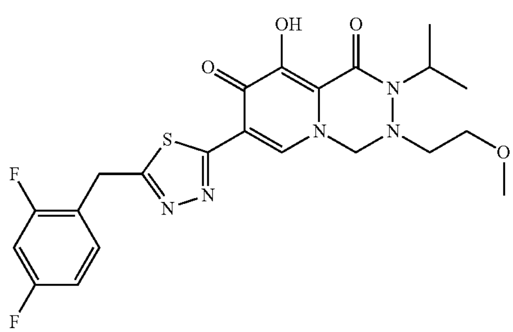 [SMILES: COCCN1Cn2cc(-c3nnc(Cc4ccc(F)cc4F)s3)c(=O)c(O)c2C(=O)N1C(C)C] | 1.90 | 492.2 | A |

TABLE 27-continued

| No. | Structure | RT (min) | [M + H]+ | Method |
|---|---|---|---|---|
| C-23 | 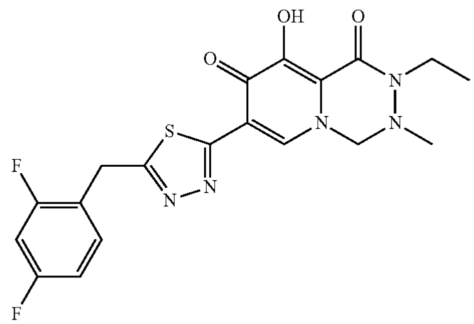 [SMILES: CCN1C(=O)c2c(O)c(=O)c(-c3nnc(Cc4ccc(F)cc4F)s3)cn2CN1C] | 1.67 | 434.1 | A |
| C-24 | 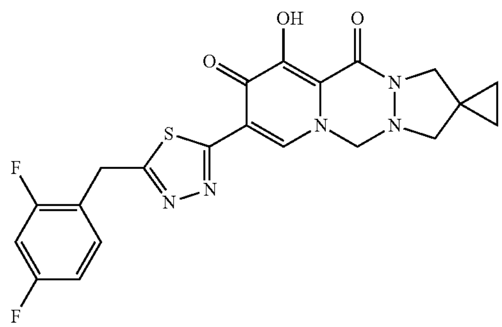 [SMILES: O=C1c2c(O)c(=O)c(-c3nnc(Cc4ccc(F)cc4F)s3)cn2CN2CC3(CC3)CN12] | 1.63 | 458.1 | A |

TABLE 28

| No. | Structure | RT (min) | [M + H]+ | Method |
|---|---|---|---|---|
| C-25 | 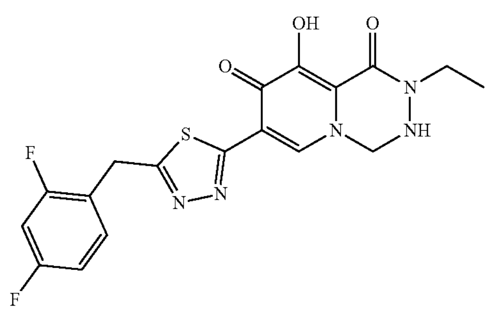 [SMILES: CCN1NCn2cc(-c3nnc(Cc4ccc(F)cc4F)s3)c(=O)c(O)c2C1=O] | 1.52 | 420.2 | A |
| C-26 | 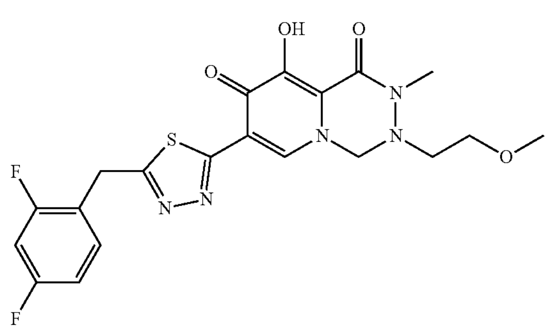 [SMILES: COCCN1Cn2cc(-c3nnc(Cc4ccc(F)cc4F)s3)c(=O)c(O)c2C(=O)N1C] | 1.59 | 464.2 | A |

TABLE 28-continued

| No. | Structure | RT (min) | [M + H]+ | Method |
|---|---|---|---|---|
| C-27 | 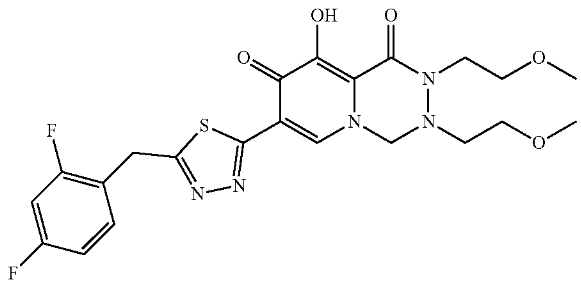 [SMILES: COCCN1Cn2cc(-c3nnc(Cc4ccc(F)cc4F)s3)c(=O)c(O)c2C(=O)N1CCOC] | 1.67 | 508.2 | A |
| C-28 | 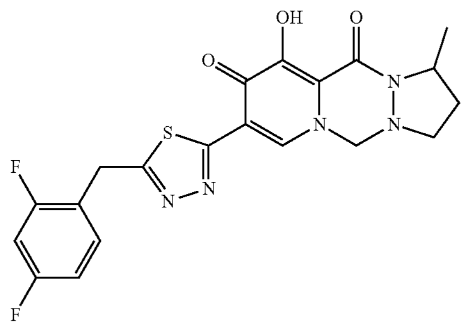 [SMILES: CC1CCN2Cn3cc(-c4nnc(Cc5ccc(F)cc5F)s4)c(=O)c(O)c3C(=O)N12] | 1.58 | 446.2 | A |

TABLE 29

| No. | Structure | RT (min) | [M + H]+ | Method |
|---|---|---|---|---|
| D-1 | 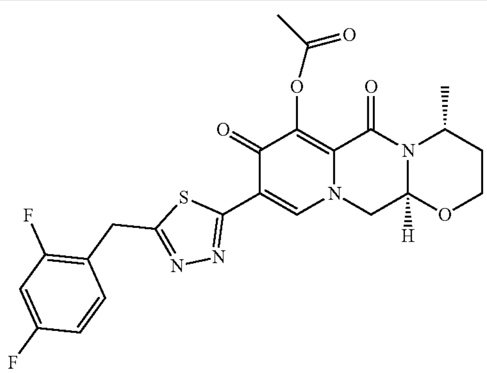 [SMILES: CC(=O)Oc1c2n(cc(-c3nnc(Cc4ccc(F)cc4F)s3)c1=O)C[C@@H]1OCC[C@@H](C)N1C2=O] | 1.71 | 503.2 | A |
| D-2 | 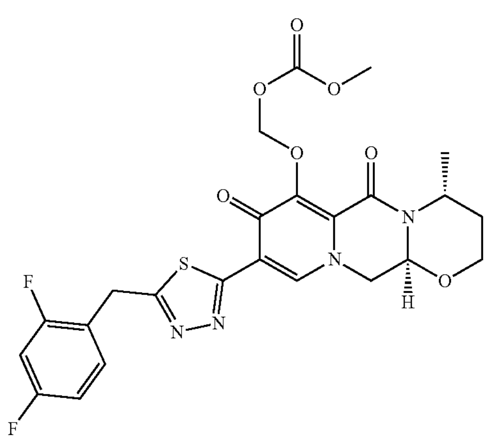 [SMILES: COC(=O)OCOc1c2n(cc(-c3nnc(Cc4ccc(F)cc4F)s3)c1=O)C[C@@H]1OCC[C@@H](C)N1C2=O] | 1.72 | 549.1 | B |

TABLE 29-continued

| No. | Structure | RT (min) | [M + H]+ | Method |
|---|---|---|---|---|
| D-3 | 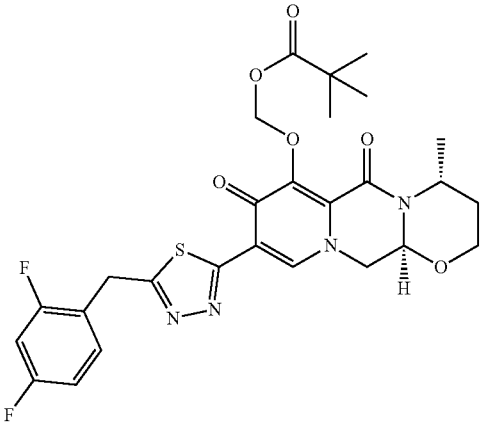 [SMILES: C[C@@H]1CCO[C@H]2Cn3cc(-c4nnc(Cc5ccc(F)cc5F)s4)c(=O)c(OCOC(=O)C(C)(C)C)c3C(=O)N12] | 2.10 | 575.2 | B |
| D-4 | 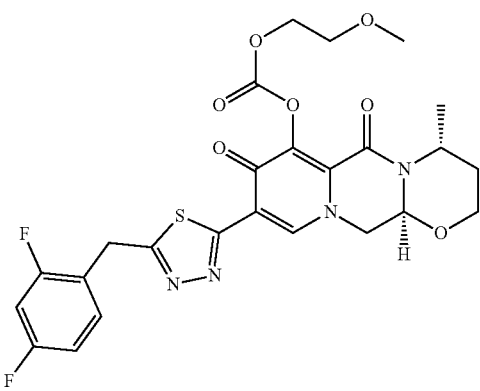 [SMILES: COCCOC(=O)Oc1c2n(cc(-c3nnc(Cc4ccc(F)cc4F)s3)c1=O)C[C@@H]1OCC[C@@H](C)N1C2=O] | 1.75 | 563.1 | B |

EXPERIMENTAL EXAMPLE 1 (Anti-HIV Activity)

(Test Method)

Previously, a series of two-fold dilution on test samples were carried out in a 96-well plate (50 μL/well). Two plates were made for measuring anti-HIV activity and measuring cytotoxicity. For each agent, measurement in duplicate was carried out. An MT-4 cell suspension of $2.5 \times 10^5$/mL was dispensed at 100 μL/well onto the 96-well plate containing the test samples. An HIV virus solution was dispensed at 50 μL/well onto the 96-well plate containing the test samples and the cell. To the plate for measuring cytotoxicity, a culture solution was dispensed at 50 μL/well. It was mixed by a plate mixer, and then incubated in a $CO_2$ incubator for 4 days. The 96-well plate incubated for 4 days was observed with the naked eye and under a microscope, and it was confirmed that there is no problem with virus proliferation and inhibition in the wells of the positive control and the negative control. Thirty microliters of a MTT (3-(4,5-dimethylthiazol-2-yl)-2,5-diphenyltetrazolium bromide) solution was dispensed to each well.

A reaction was allowed to occur in a $CO_2$ incubator for an hour. From each well, 150 μL of the supernatant was removed such that cells are not sucked. One-hundred and fifty microliters of a cell lysis solution was added thereto, and then it was mixed well by a plate mixer until the whole cells are lysed. The mixed 96-well plates were measured by a microplate reader at two wavelengths, 560 nm/690 nm.

Based on the following calculation formula, 50% HIV inhibition concentration (EC50) was calculated.

$$EC50 = 10Z$$

$$Z = (50\% - \text{Low }\%)/(\text{High }\% - \text{Low }\%) \times \{\log(\text{High conc.}) - \log(\text{Low conc.})\} + \log(\text{Low conc.})$$

Based on the following calculation formula, 50% cytotoxic concentration (CC50) was calculated.

$$CC50 = 10Z$$

$$Z = (50\% - \text{Low }\%)/(\text{High }\% - \text{Low }\%) \times \{\log(\text{High conc.}) - \log(\text{Low conc.})\} + \log(\text{Low conc.})$$

Based on the following calculation formula, selectivity index (ST) was calculated.

$$SI = CC50/EC50$$

(Result)

TABLE 30

| No. | EC50 (nM) |
|---|---|
| A-1 | 7.8 |
| A-2 | 2.5 |
| A-3 | 3.7 |
| A-4 | 7.4 |
| A-5 | 8 |
| A-6 | 1.9 |
| A-7 | 6.5 |
| A-8 | 3.5 |

TABLE 30-continued

| No. | EC50 (nM) |
|---|---|
| A-9 | 7.1 |
| A-10 | 4.4 |
| A-11 | 8.8 |
| A-12 | 4.9 |
| A-13 | 6.0 |
| A-14 | 1.2 |
| A-15 | 1.1 |
| A-16 | 2.1 |
| A-17 | 2.3 |
| A-18 | 2.3 |
| A-19 | 3.1 |
| A-20 | 3.0 |
| A-21 | 1.0 |
| A-22 | 1.7 |
| A-23 | 2.6 |
| A-24 | 4.2 |
| A-25 | 3.4 |
| A-26 | 3.8 |
| A-27 | 3.5 |
| A-28 | 3.3 |
| A-29 | 2.1 |
| A-31 | 2.3 |
| A-32 | 12 |
| A-33 | 2.5 |
| A-34 | 13 |
| A-35 | 2.8 |
| A-36 | 1.4 |
| A-37 | 2.3 |
| A-38 | 2.7 |
| A-39 | 1.6 |
| A-40 | 11 |
| A-42 | 10 |
| A-43 | 3.6 |
| A-44 | 5.1 |
| A-45 | 4.1 |
| A-46 | 3.9 |
| A-47 | 3.4 |
| A-48 | 14 |
| A-49 | 10 |
| A-50 | 12 |
| A-51 | 6.8 |
| A-52 | 18 |
| A-53 | 3.0 |
| A-54 | 1.6 |
| A-55 | 1.7 |
| A-56 | 4.0 |
| A-57 | 1.7 |
| A-58 | 10 |
| A-59 | 9.5 |
| A-60 | 2.0 |
| A-61 | 4.1 |
| A-62 | 1.6 |
| A-63 | 2.0 |
| A-64 | 1.6 |
| A-65 | 4.2 |
| A-66 | 7.2 |
| A-67 | 4.2 |
| A-68 | 4.6 |
| A-69 | 5.1 |
| A-70 | 8.0 |
| A-71 | 9.3 |
| A-72 | 8.5 |
| A-73 | 5.7 |
| A-74 | 12 |
| A-75 | 10 |
| A-76 | 4.7 |
| A-77 | 7.2 |
| A-78 | 4.6 |
| A-79 | 15 |
| A-80 | 6.3 |
| B-1 | 2.9 |
| B-2 | 3.9 |
| B-3 | 3.7 |
| B-4 | 5.5 |
| B-5 | 6.7 |
| B-6 | 7.5 |
| B-7 | 2.9 |
| B-8 | 3.8 |
| B-9 | 2.0 |
| B-10 | 10 |
| B-11 | 5.9 |
| B-12 | 11 |
| B-13 | 7.7 |
| B-14 | 10 |
| B-15 | 4.0 |
| B-16 | 7.7 |
| B-17 | 5.3 |
| B-18 | 14 |
| B-19 | 18 |
| B-21 | 4.0 |
| B-22 | 3.5 |

TABLE 31

| No. | EC50 (nM) |
|---|---|
| C-1 | 3.4 |
| C-2 | 1.4 |
| C-3 | 1.1 |
| C-4 | 2.1 |
| C-5 | 3.4 |
| C-6 | 5.7 |
| C-7 | 2.0 |
| C-8 | 2.4 |
| C-10 | 5.8 |
| C-12 | 8.7 |
| C-13 | 2.7 |
| C-14 | 2.2 |
| C-15 | 1.7 |
| C-16 | 8.5 |
| C-18 | 2.3 |
| C-19 | 4.2 |
| C-20 | 1.7 |
| C-21 | 1.5 |
| C-22 | 1.3 |
| C-23 | 1.2 |
| C-24 | 2.4 |
| C-25 | 2.2 |
| C-26 | 1.5 |
| C-27 | 2.0 |
| C-28 | 4.8 |
| D-1 | 3.8 |
| D-2 | 8.0 |
| D-3 | 4.8 |
| D-4 | 4.1 |

FORMULATION EXAMPLE

A term "active ingredient" means the present compound, a tautomer thereof, a pharmaceutically acceptable salt thereof, or a solvate thereof.

Formulation Example 1

A hard gelatin capsule is prepared using the following ingredients:

| | Dose (mg/capsule) |
|---|---|
| Active ingredient | 250 |
| Starch (dried) | 200 |
| Magnesium stearate | 10 |
| Total | 460 mg |

Formulation Example 2

A tablet is prepared using the following ingredients:

| | Dose (mg/capsule) |
|---|---|
| Active ingredient | 250 |
| Cellulose (microcrystalline) | 200 |
| Silicon dioxide (fumed) | 10 |
| Stearic acid | 5 |
| Total | 665 mg |

Ingredients are mixed, and compressed to obtain tablets, each weighing 665 mg.

INDUSTRIAL APPLICABILITY

The present compound has integrase inhibitory activity and/or cell proliferation inhibitory activity against viruses, in particular, HIV. Thus, the compound is useful in preventing or treating various diseases, viral infections (e.g., AIDS), and the like in which integrase participates.

The invention claimed is:
1. A compound represented by the following formula (I-3), or its pharmaceutically acceptable salt:

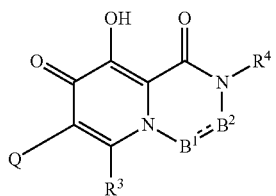

(I-3)

wherein Q is substituted or unsubstituted carbocyclyl or substituted or unsubstituted heterocyclyl;
the broken line represents the presence or absence of a bond;
(1) when either one of $B^1$ and $B^2$ is $CR^{20}R^{21}$ and the other is $NR^{22}$, the broken line represents the absence of a bond; and $R^{20}$ and $R^{22}$ are taken together with the neighboring atoms to form substituted or unsubstituted heterocycle;
(2) when $B^1$ is $CR^{20}R^{21}$ and $B^2$ is $NR^{22}$, $R^4$ and $R^{22}$ are taken together with the neighboring atoms to form substituted or unsubstituted heterocycle;
(3) when $B^1$ is $NR^{22}$ and $B^2$ is $CR^{20}R^{21}$, $R^4$ and $R^{21}$ are taken together with the neighboring atoms to form F ring;
F ring is represented by any one of the following rings:

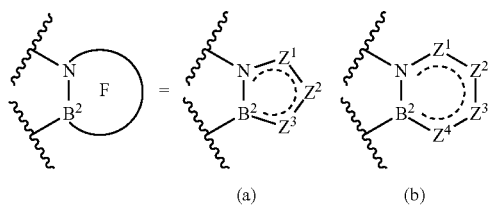

(a) (b)

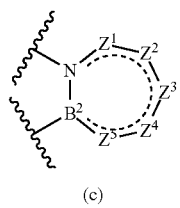

(c)

wherein $Z^1$, $Z^2$, $Z^3$, $Z^4$ and $Z^5$ are each independently $CR^1R^2$, $CR^1$, O, S, SO, $SO_2$, N or $NR^{19}$;
a) $Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ are taken together to form substituted or unsubstituted (C2-C4) bridge; or
b) $R^1$ and $R^2$ are taken together to form substituted or unsubstituted spiro ring;
$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is independently selected from the same substituent group as $R^4$), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido, or substituted or unsubstituted thioureido;
$R^{19}$ is hydrogen, substituted or unsubstituted lower alkyl, lower alkenyl, substituted or unsubstituted lower alkylcarbonyl, or substituted or unsubstituted lower alkylsulfonyl;
the broken line represents the presence or absence of a bond; or
F ring is represented by any one of the following rings:

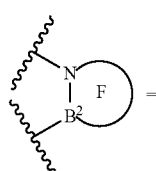

(a) 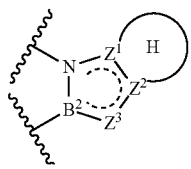

(b) 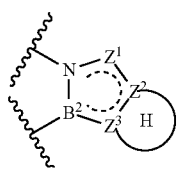

(c) 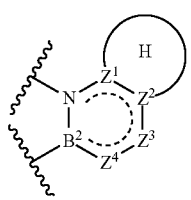

(d) 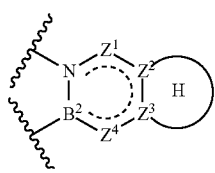

(e) 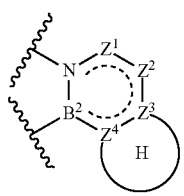

(f) 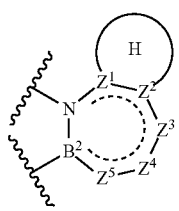

(g) 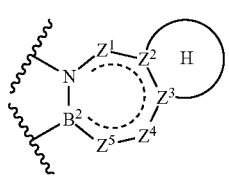

(h) 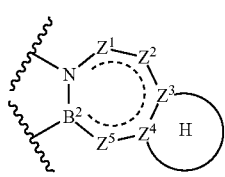

(i) 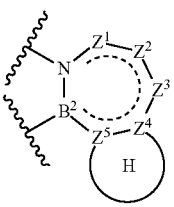

wherein H ring is substituted or unsubstituted carbocycle or substituted or unsubstituted heterocycle;

$Z^1$, $Z^2$, $Z^3$, $Z^4$ and $Z^5$ are each independently $CR^1R^2$, $CR^1$, C, O, S, SO, $SO_2$, N or $NR^{19}$ (when $Z^1$, $Z^2$, $Z^3$, $Z^4$ or $Z^5$ is/are constituent atom(s) of H ring, $Z^1$, $Z^2$, $Z^3$, $Z^4$ and $Z^5$ are each independently $CR^1$, C or N); or $Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ are taken together to form substituted or unsubstituted (C2-C4) bridge;

$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$ (wherein $R^5$ is independently selected from the same substituent group as $R^4$), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido, or substituted or unsubstituted thioureido; or $R^1$ and $R^2$ on the same carbon atom are taken together to form oxo, thioxo or substituted or unsubstituted spiro ring;

$R^{19}$ is hydrogen, substituted or unsubstituted lower alkyl, lower alkenyl, substituted or unsubstituted lower alkylcarbonyl, or substituted or unsubstituted lower alkyl sulfonyl; and the broken line represents the presence or absence of a bond; or (4) when either one of $B^1$ and $B^2$ is $CR^{23}$ and the other is N, the broken line represents the presence of a bond;

when B² is CR²³, R⁴ and R²³ are taken together with the neighboring atoms to form substituted or unsubstituted heterocycle;

R²⁰, R²¹, R²² and R²³ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, SO₂, NR⁵ (wherein R⁵ is independently selected from the same substituent group as R⁴), —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclyl carbonyl, substituted or unsubstituted heterocyclyl lower alkyl carbonyl, substituted or unsubstituted heterocyclyloxycarbonyl, substituted or unsubstituted aminocarbonyl, substituted or unsubstituted ureido, or substituted or unsubstituted thioureido;

R³ is hydrogen, halogen, hydroxy, substituted or unsubstituted lower alkyl, substituted or unsubstituted cycloalkyl, substituted or unsubstituted lower alkenyl, substituted or unsubstituted lower alkoxy, substituted or unsubstituted lower alkenyloxy, substituted or unsubstituted aryl, substituted or unsubstituted aryloxy, substituted or unsubstituted heterocyclyl, substituted or unsubstituted heterocyclyloxy, or substituted or unsubstituted amino; and R⁴ is hydrogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, hydroxy, substituted or unsubstituted amino, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, or lower alkyl substituted with substituted or unsubstituted phosphoric acid residue (wherein a heteroatom group selected from the group consisting of CO, O, S, SO, SO₂, NR$^a$ (R$^a$ is hydrogen or lower alkyl), —N= and =N— may intervene in the lower alkyl).

2. The compound or its pharmaceutically acceptable salt according to claim 1, having the following formula (I-3-1):

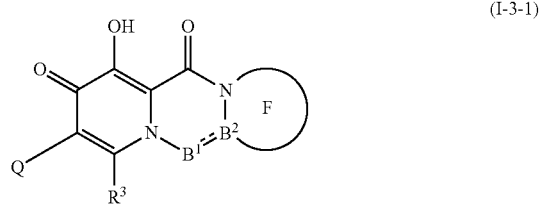

(I-3-1)

wherein F ring is substituted or unsubstituted heterocycle;
B¹ is CR²⁰R²¹, N or NR²²;
when B¹ is CR²⁰R²¹, the broken line represents the absence of a bond, and B² is N;
when B¹ is N, the broken line represents the presence of a bond, and B² is C; or
when B¹ is NR²², the broken line represents the absence of a bond, and B² is CR²⁰; and
Q and R³ are as defined in claim 1.

3. The compound or its pharmaceutically acceptable salt according to claim 2, wherein F ring is represented by any one of the following rings:

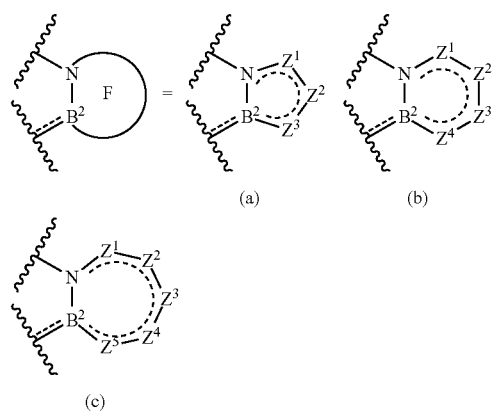

(a)   (b)

(c)

wherein Z¹, Z², Z³, Z⁴ and Z⁵ are each independently CR¹R², CR¹, O, S, SO, SO₂, N or NR¹⁹; or
Z¹ and Z³, Z¹ and Z⁴, Z¹ and Z⁵, Z² and Z⁴, Z² and Z⁵, or Z³ and Z⁵ may be taken together to form substituted or unsubstituted (C2-C4) bridge;
R¹ and R² are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$, —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido, or substituted or unsubstituted thioureido; or $R^1$ and $R^2$ may be taken together to form oxo, thioxo or substituted or unsubstituted spiro ring;

$R^{19}$ is hydrogen, substituted or unsubstituted lower alkyl, lower alkenyl, substituted or unsubstituted lower alkylcarbonyl or substituted or unsubstituted lower alkylsulfonyl; and the broken line represents the presence or absence of a bond.

4. The compound or its pharmaceutically acceptable salt according to claim 2, wherein F ring is represented by any one of the following rings:

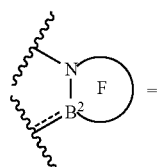
(a)

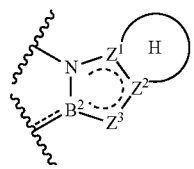
(b)

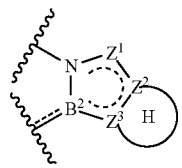
(c)

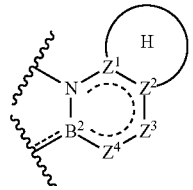
(d)

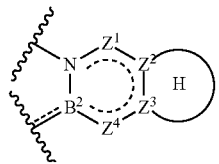
(e)

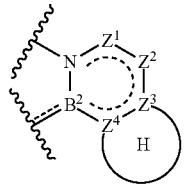
(f)

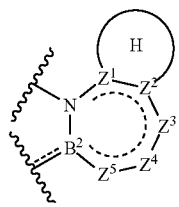
(g)

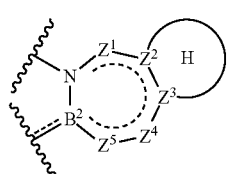
(h)

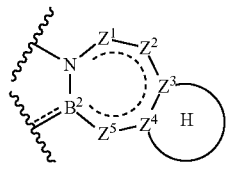
(i)

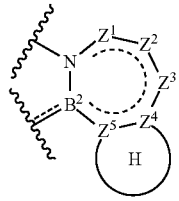

wherein H ring is substituted or unsubstituted carbocycle or substituted or unsubstituted heterocycle;

$Z^1$, $Z^2$, $Z^3$, $Z^4$ and $Z^5$ are each independently $CR^1R^2$, $CR^1$, C, O, S, SO, $SO_2$, N or $NR^{19}$ (when $Z^1$, $Z^2$, $Z^3$, $Z^4$ or $Z^5$ is/are constituent atom(s) of H ring, $Z^1$, $Z^2$, $Z^3$, $Z^4$ and $Z^5$ are each independently $CR^1$, C or N); or $Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ may be taken together to form substituted or unsubstituted (C2-C4) bridge;

$R^1$ and $R^2$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$, —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido, or substituted or unsubstituted thioureido; or $R^1$ and $R^2$ may be taken together to form oxo, thioxo or substituted or unsubstituted spiro ring;

$R^{19}$ is hydrogen, substituted or unsubstituted lower alkyl, lower alkenyl, substituted or unsubstituted lower alkylcarbonyl or substituted or unsubstituted lower alkylsulfonyl; and the broken line represents the presence or absence of a bond.

5. The compound or its pharmaceutically acceptable salt according to claim 4, wherein H ring is substituted or unsubstituted 4- to 7-membered carbocycle or substituted or unsubstituted 4- to 7-membered heterocycle.

6. The compound or its pharmaceutically acceptable salt according to claim 1 represented by the following formula (I-3-2):

(I-3-2)

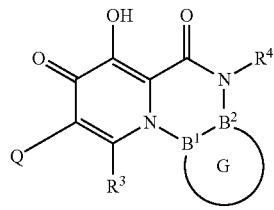

wherein G ring is substituted or unsubstituted carbocycle or substituted or unsubstituted heterocycle;

$B^1$ is $CR^{21}$ or N;

when $B^1$ is $CR^{21}$, $B^2$ is N; or when $B^1$ is N, $B^2$ is $CR^{21}$; and Q, $R^3$ and $R^4$ are as defined in claim 1.

7. The compound or its pharmaceutically acceptable salt according to claim 6, wherein G ring is represented by any one of the following rings:

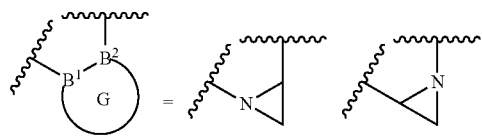

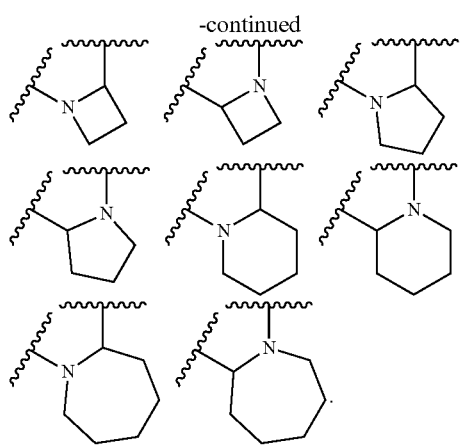

8. The compound or its pharmaceutically acceptable salt according to claim 1 represented by the following formula (I-3-5) or (I-3-6):

(I-3-5)

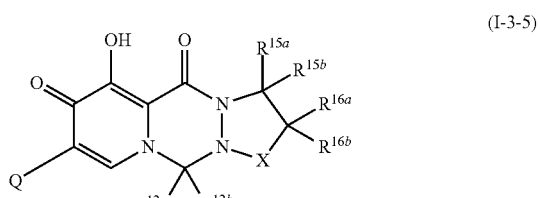

(I-3-6)

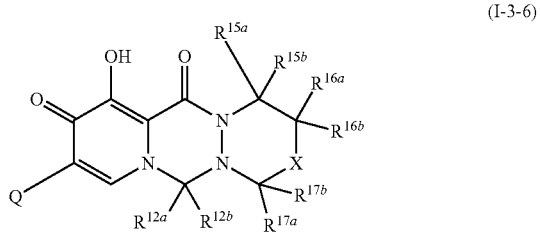

wherein

X is $CR^{18a}R^{18b}$, $NR^{24}$, O or S;

$R^{15a}$, $R^{15b}$, $R^{16a}$, $R^{16b}$, $R^{17a}$, $R^{17b}$, $R^{18a}$, $R^{18b}$, and $R^{24}$ are each independently, hydrogen, halogen, substituted or unsubstituted lower alkyl, substituted or unsubstituted cycloalkyl, substituted or unsubstituted cycloalkyl lower alkyl, substituted or unsubstituted lower alkenyl, substituted or unsubstituted lower alkoxy, substituted or unsubstituted lower alkenyloxy, substituted or unsubstituted aryl, substituted or unsubstituted aryl lower alkyl, substituted or unsubstituted aryloxy, substituted or unsubstituted heterocyclyl, substituted or unsubstituted heterocyclyl lower alkyl, substituted or unsubstituted heterocyclyloxy, substituted or unsubstituted phosphoric acid residue, aryl substituted with substituted or unsubstituted phosphoric acid residue, hydroxy substituted with substituted or unsubstituted phosphoric acid residue, amino substituted with substituted or unsubstituted phosphoric acid residue, lower alkyl substituted with substituted or unsubstituted phosphoric acid residue (wherein a heteroatom group selected from the group consisting of O, S, SO, $SO_2$, $NR^5$, —N= and =N— may intervene in the lower alkyl), hydroxy, substituted or unsubstituted amino, substituted or unsubstituted lower alkylcarbonyl, substituted or unsubstituted cycloalkylcarbonyl, substituted or unsubstituted cycloalkyl lower alkylcarbonyl, substituted or unsubstituted lower alkoxycarbonyl, substituted or unsubstituted arylcarbonyl, substituted or unsubstituted aryl lower alkylcarbonyl, substituted or unsubstituted aryloxycarbonyl, substituted or unsubstituted heterocyclylcarbonyl, substituted or unsubstituted heterocyclyl lower alkylcarbonyl, substituted or unsubstituted heterocyclyloxycarbonyl, substituted or unsubstituted aminocarbonyl, substituted or unsubstituted ureido, or substituted or unsubstituted thioureido; or $R^{15a}$ and $R^{15b}$, $R^{16a}$ and $R^{16b}$, $R^{17a}$ and $R^{17b}$, or $R^{18a}$ and $R^{18b}$ may be taken together to form oxo, thioxo or substituted or unsubstituted spiro ring; or $R^{15b}$ and $R^{16b}$, $R^{16b}$ and $R^{18b}$, and/or $R^{17b}$ and $R^{18b}$ may be taken together to form substituted or unsubstituted carbocycle or substituted or unsubstituted heterocycle; or $R^{15b}$ and $R^{17b}$, $R^{15b}$ and $R^{18b}$, or $R^{16b}$ and $R^{17b}$ may be taken together to form substituted or unsubstituted (C2-C4) bridge; or $R^{16b}$ and $R^{24}$, or $R^{17b}$ and $R^{24}$ may be taken together to form substituted or unsubstituted heterocycle; or $R^{15b}$ and $R^{24}$ may be taken together to form substituted or unsubstituted (C2-C4) bridge.

9. The compound or its pharmaceutically acceptable salt according to claim 8, wherein $R^{15a}$ is hydrogen or substituted or unsubstituted lower alkyl.

10. The compound or its pharmaceutically acceptable salt according to claim 8, wherein $R^{15b}$ is hydrogen.

11. The compound or its pharmaceutically acceptable salt according to claim 8, wherein $R^{16a}$ is hydrogen or substituted or unsubstituted lower alkyl.

12. The compound or its pharmaceutically acceptable salt according to claim 8, wherein $R^{16b}$ is hydrogen.

13. The compound or its pharmaceutically acceptable salt according to claim 8, wherein $R^{17a}$ is hydrogen or substituted or unsubstituted lower alkyl.

14. The compound or its pharmaceutically acceptable salt according to claim 8, wherein $R^{17b}$ is hydrogen.

15. The compound or its pharmaceutically acceptable salt according to claim 8, wherein $R^{18a}$ is hydrogen or substituted or unsubstituted lower alkyl.

16. The compound or its pharmaceutically acceptable salt according to claim 8, wherein $R^{18b}$ is hydrogen.

17. The compound or its pharmaceutically acceptable salt according to claim 8, wherein $R^{24}$ is hydrogen or substituted or unsubstituted lower alkyl.

18. The compound or its pharmaceutically acceptable salt according to claim 1, wherein Q is substituted or unsubstituted heterocyclyl.

19. The compound or its pharmaceutically acceptable salt according to claim 1, wherein Q is substituted or unsubstituted 5- to 7-membered monocyclic heterocyclyl.

20. The compound or its pharmaceutically acceptable salt according to claim 1, wherein Q is carbocyclyl or heterocyclyl substituted with the same or different, 1 to 4 substituent(s) selected from Substituent group A, wherein Substituent group A is selected from the group consisting of: lower alkyl, lower alkoxy, halogen, halogenated lower alkyl, halogenated lower alkoxy, and a group represented by the formula (B):

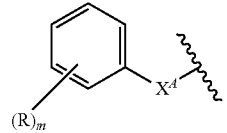

(B)

wherein
$X^A$ is a group selected from the group consisting of:
$X^{A1}$: a single bond;
$X^{A2}$: a group selected from the group consisting of C(=O) and C(=S);
$X^{A3}$: a heteroatom group selected from the group consisting of O, S, SO, SO$_2$, and N(R$^{1'}$) wherein R$^{1'}$ is hydrogen or lower alkyl;
$X^{A4}$: a group formed by linking the same or different, two or more groups selected from the group consisting of $X^{A2}$ and $X^{A3}$;
$X^{A5}$: a group selected from the group consisting of —N=N—, —C(R$^{1'}$)=N—, and —N=C(R$^{1'}$)— wherein R$^{1'}$ is hydrogen or lower alkyl;
$X^{A6}$: substituted or unsubstituted lower alkylene or substituted or unsubstituted lower alkenylene;
$X^{A7}$: $X^{A6}$ intervened by one or any two or more groups selected from the group consisting of $X^{A2}$, $X^{A3}$, $X^{A4}$, and $X^{A5}$;
$X^{A8}$: a group CR$^{1'}$R$^{2'}$ wherein R$^{1'}$ and R$^{2'}$ are taken together with neighboring atoms to form carbocycle or heterocycle; and
$X^{A9}$: a spacer consisting of any combination of $X^{A1}$ to $X^{A8}$;

R is a group independently selected from the group consisting of:
(1) lower alkyl,
(2) lower alkoxy,
(3) halogen,
(4) halogenated lower alkyl,
(5) halogenated lower alkoxy, and
(6) lower cycloalkyl;

m is an integer of 0 to 5.

21. The compound or its pharmaceutically acceptable salt according to claim 20, wherein Q is represented by the following formula (1) or (2):

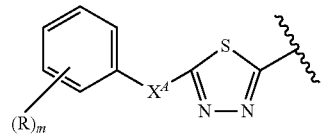

(1)

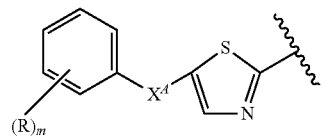

(2)

wherein R, m and $X^A$ are as defined in claim 20.

22. The compound or its pharmaceutically acceptable salt according to claim 20, wherein $X^A$ is lower alkylene; R is independently lower alkoxy, halogen or halogenated lower alkyl; and m is 1 or 2.

23. A pharmaceutical composition comprising the compound according to claim 1, or a pharmaceutically acceptable salt thereof, and a pharmaceutically acceptable carrier or diluent.

24. The pharmaceutical composition according to claim 23, which has anti-HIV activity.

25. The pharmaceutical composition according to claim 23, which has an HIV integrase inhibitory activity.

26. A method for treating AIDS comprising administering an effective amount of the compound of claim 1 or a pharmaceutically acceptable salt thereof to a human or animal in need thereof.

* * * * *